(12) United States Patent
Genovese et al.

(10) Patent No.: US 11,976,302 B2
(45) Date of Patent: May 7, 2024

(54) COMPOSITIONS AND METHODS FOR INCREASING THE CULTURE DENSITY OF A CELLULAR BIOMASS WITHIN A CULTIVATION INFRASTRUCTURE

(71) Applicant: Upside Foods, Inc., Berkeley, CA (US)

(72) Inventors: Nicholas J. Genovese, Hayward, CA (US); Meri Teresa Firpo, Oakland, CA (US); Daphné Dambournet, San Francisco, CA (US)

(73) Assignee: Upside Foods, Inc., Berkeley, CA (US)

( * ) Notice: Subject to any disclaimer, the term of this patent is extended or adjusted under 35 U.S.C. 154(b) by 658 days.

(21) Appl. No.: 16/610,873

(22) PCT Filed: May 5, 2018

(86) PCT No.: PCT/US2018/031276
§ 371 (c)(1),
(2) Date: Nov. 4, 2019

(87) PCT Pub. No.: WO2018/208628
PCT Pub. Date: Nov. 15, 2018

(65) Prior Publication Data
US 2020/0165569 A1 May 28, 2020

Related U.S. Application Data

(60) Provisional application No. 62/502,669, filed on May 6, 2017.

(51) Int. Cl.
*C12N 5/077* (2010.01)
*C07K 14/47* (2006.01)

(52) U.S. Cl.
CPC ........ *C12N 5/0658* (2013.01); *C07K 14/4703* (2013.01); *C12N 5/0656* (2013.01); *C12N 2501/998* (2013.01); *C12N 2511/00* (2013.01)

(58) Field of Classification Search
CPC ............... C12N 5/0658; C12N 5/0656; C12N 2501/998; C12N 2501/00; C07K 14/4703
See application file for complete search history.

(56) References Cited

U.S. PATENT DOCUMENTS

| | | | |
|---|---|---|---|
| 5,624,840 | A | 4/1997 | Naughton et al. |
| 6,593,275 | B1 | 7/2003 | Unkefer et al. |
| 6,767,719 | B1 | 7/2004 | Morin et al. |
| 6,835,390 | B1 | 12/2004 | Vein |
| 7,033,744 | B2 | 4/2006 | Kobayashi et al. |
| 7,147,871 | B2 | 12/2006 | Harbin et al. |
| 7,270,829 | B2 | 9/2007 | Van Eelen |
| 8,105,575 | B2 | 1/2012 | Kim et al. |
| 8,703,216 | B2 | 4/2014 | Forgacs et al. |
| 8,883,502 | B2 | 11/2014 | Zhang et al. |
| 9,102,739 | B2 | 8/2015 | Lazar et al. |
| 11,479,792 | B2 | 10/2022 | Genovese et al. |
| 2002/0068706 | A1 | 6/2002 | Gyuris et al. |
| 2005/0260748 | A1 | 11/2005 | Chang et al. |
| 2006/0121006 | A1 | 6/2006 | Chancellor et al. |
| 2007/0248716 | A1 | 10/2007 | Kruse et al. |
| 2010/0319079 | A1 | 12/2010 | Kruse et al. |
| 2011/0091604 | A1 | 4/2011 | Miller |
| 2011/0191871 | A1 | 8/2011 | Walsh et al. |
| 2011/0225664 | A1 | 9/2011 | Smith |
| 2011/0301249 | A1 | 12/2011 | Challakere |
| 2013/0004466 | A1 | 1/2013 | Tremblay et al. |
| 2013/0029008 | A1 | 1/2013 | Forgacs et al. |
| 2013/0171731 | A1 | 7/2013 | Ivashchenko et al. |
| 2013/0224855 | A1 | 8/2013 | Gupta et al. |
| 2013/0255003 | A1 | 10/2013 | Forgacs et al. |
| 2014/0093618 | A1 | 4/2014 | Forgacs et al. |
| 2014/0242155 | A1 | 8/2014 | Ramunas et al. |
| 2014/0370537 | A1 | 12/2014 | Sakurai et al. |
| 2015/0025128 | A1 | 1/2015 | Cain et al. |

(Continued)

FOREIGN PATENT DOCUMENTS

| | | |
|---|---|---|
| CA | 2333966 C | 12/1999 |
| CA | 2780087 A1 | 12/2012 |

(Continued)

OTHER PUBLICATIONS

Mannaerts et al. The Hippo pathway effector YAP controls mouse hepatic stellate cell activation, Journal of Hepatology, 63: 679-688 (Year: 2015).*
Chen, et al., Homeostatic control of Hippo signaling activity revealed by an endogenous activating mutation in YAP, Genes & Development, 29: 1285-1297. (Year: 2015).*
Lei, et al., TAZ promotes cell proliferation and epithelial-mesenchymal transition and is inhibited by the hippo pathway, Molecular and Cellular Biology, 28(7): 2426-2436. (Year: 2008).*
Benjaminson, et al., In vitro edible muscle protein production system (MPPS) stage 1, fish, Acta Astronautica, 51(12): 879-889. (Year: 2002).*
Poon et al., The sterile 20-like kinase Tao-1 controls tissue growth by regulating the Salvador-Warts-Hippo pathway, Developmental Cell, 21: 896-906. (Year: 2011).*

(Continued)

*Primary Examiner* — Laura Schuberg
*Assistant Examiner* — Joseph Paul Miano
(74) *Attorney, Agent, or Firm* — Ballard Spahr LLP

(57) ABSTRACT

Provided herein are methods to increase the culture density and/or thickness of a cellular biomass in a cultivation infrastructure, to improve the culture of cells in the absence of serum in a cultivation infrastructure, and to promote anchorage-independent growth of a cellular biomass in a cultivation infrastructure. The methods comprise inhibiting the HIPPO signaling pathway, for example, by activating YAP1, activating TAZ, and/or inhibiting MOB1, LATS1 kinase, LATS2 kinase, WW45, MST1 kinase, and/or MST2 kinase in the cellular biomass. In some embodiments, the cellular biomass is harvested from the cultivation infrastructure for the formulation of cell-based food products or ingredients, such as animal meat manufactured from cells in an ex vivo process or for therapeutic applications such as organ or tissue transplantation or grafting.

16 Claims, 18 Drawing Sheets
Specification includes a Sequence Listing.

(56) References Cited

U.S. PATENT DOCUMENTS

| | | |
|---|---|---|
| 2015/0079238 A1 | 3/2015 | Marga et al. |
| 2015/0087532 A1 | 3/2015 | Brown et al. |
| 2015/0133520 A1 | 5/2015 | Czech et al. |
| 2015/0216216 A1 | 8/2015 | Marga |
| 2015/0231209 A1 | 8/2015 | Hsueh et al. |
| 2015/0289541 A1 | 10/2015 | Brown et al. |
| 2015/0296834 A1 | 10/2015 | Geistlinger |
| 2015/0296835 A1 | 10/2015 | Anderson et al. |
| 2015/0305361 A1 | 10/2015 | Holz-Schietinger et al. |
| 2015/0305390 A1 | 10/2015 | Vrljic et al. |
| 2016/0227830 A1 | 8/2016 | Genovese et al. |
| 2016/0251625 A1 | 9/2016 | Genovese et al. |
| 2017/0101629 A1 | 4/2017 | Minshull et al. |
| 2017/0114382 A1 | 4/2017 | Follit et al. |
| 2017/0369849 A1 | 12/2017 | Hanson et al. |
| 2019/0024079 A1 | 1/2019 | Genovese et al. |
| 2020/0190524 A1 | 6/2020 | Minshull et al. |
| 2021/0106032 A1 | 4/2021 | Leung et al. |
| 2021/0145031 A1 | 5/2021 | Leung et al. |

FOREIGN PATENT DOCUMENTS

| | | | |
|---|---|---|---|
| CN | 1942576 A | 4/2007 | |
| CN | 101624570 A | 1/2010 | |
| EP | 0435617 A1 | 7/1991 | |
| EP | 1037966 B1 | 5/2003 | |
| JP | 2013-81783 | 5/2013 | |
| JP | WO2016052472 A1 * | 4/2016 | ......... A61L 27/3895 |
| WO | WO 1993/009236 A1 | 5/1993 | |
| WO | WO 1999/031222 A1 | 6/1999 | |
| WO | WO 1999/031223 A1 | 6/1999 | |
| WO | WO 2006/041429 A2 | 4/2006 | |
| WO | WO 2007/071339 A1 | 6/2007 | |
| WO | WO 2010/068897 A2 | 6/2010 | |
| WO | WO 2012/095514 A1 | 7/2012 | |
| WO | WO 2012/170995 A2 | 12/2012 | |
| WO | WO 2012/176023 A1 | 12/2012 | |
| WO | WO 2013/007656 A1 | 1/2013 | |
| WO | WO 2013/016547 A2 | 1/2013 | |
| WO | WO 2013/073246 A1 | 5/2013 | |
| WO | WO 2015/038988 A1 | 3/2015 | |
| WO | WO-2015/066377 A1 | 5/2015 | |
| WO | WO 2015/120174 A1 | 8/2015 | |
| WO | WO 2015/167959 A1 | 11/2015 | |
| WO | WO 2017/019125 A1 | 2/2017 | |
| WO | WO-2017/120089 A1 | 7/2017 | |
| WO | WO-2017/124100 A1 | 7/2017 | |
| WO | WO-2018/208628 A1 | 11/2018 | |
| WO | WO-2019/014652 A1 | 1/2019 | |

OTHER PUBLICATIONS

Metzen et al., Pericellular PO2 and O2 consumption in monolayer cell cultures, Respiration Physiology, 100: 101-106. (Year: 1995).*
Broedel et al., The case for serum-free media, BioProcess International, p. 56-58. (Year: 2003).*
Kuang et al., Asymmetric self-renewal and commitment of satellite stem cells in muscle, Cell, 129: 999-1010 (Year: 2007).*
Powers et al., Accurate control of oxygen level in cells during culture on silicone rubber membranes with application to stem cell differentiation, Biotechnology Progress, 26(3): 805-818. (Year: 2009).*
Bian et al., Engineered skeletal muscle tissue networks with controllable architecture, Biomaterials, 30, 1401-1412. (Year: 2009).*
Judson et al., The HIPPO pathway member YAP plays a key role in influencing fate decisions in muscle satellite cells, Journal of Cell Science, 125: 6009-6019. (Year: 2012).*
Mohamed et al., The HIPPO effector TAZ (WWTR1) transforms myoblasts and TAZ abundance is associated with reduced survival in embryonal rhabdomyosarcoma, Journal of Pathology, 240: 3-14. (Year: 2016).*
Merriam-Webster, "Livestock" definition, retrieved from internet Aug. 19, 2022. (Year: 2022).*

Merriam-Webster, "Game" definition, retrieved from internet Aug. 19, 2022. (Year: 2022).*
Dictionary.com, "myogenic" definition, retrieved from internet Aug. 19, 2022. (Year: 2022).*
Post et al., Cultured beef: medical technology to produce food, J Sci Food Agric. (Year: 2013).*
European Patent Office, Extended European Search Report and Opinion, EP Patent Application No. 18797874.7, dated May 21, 2021, 15 pages.
Kucharczak, J. et al., "R-Cadherin Expression Inhibits Myogenesis and Induces Myoblast Transformation via Rac1 GTPase," Cancer Research, vol. 68, No. 16, Aug. 15, 2008, pp. 6559-6568.
McKinnon, T. et al., "Kras activation in p53-deficient myoblasts results in high-grade sarcoma formation with impaired myogenic differentiation," Oncotarget, vol. 6, No. 16, Jun. 10, 2015, pp. 14220-14232.
Minniti, C.P. et al., "Insulin-like growth factor II overexpression in myoblasts induces phenotypic changes typical of the malignant phenotype," Cell Growth & Differentiation, vol. 6, Mar. 1995, pp. 263-269.
Miranda, A.F.et al., "Transformation of human skeletal muscle cells by simian virus 40," PNAS, vol. 80, Nov. 1983, pp. 6581-6585.
Nguyen, H.T. et al., "Viral Small T Oncoproteins Transform Cells by Alleviating Hippo-Pathway-Mediated Inhibition of the YAP Proto-oncogene," Cell Reports, vol. 8, No. 3, Aug. 7, 2014, pp. 707-713.
Overholtzer, M. et al., "Transforming properties of YAP, a candidate oncogene on the chromosome 11q22 amplicon," PNAS, vol. 103, No. 33, Aug. 15, 2006, pp. 12405-12410.
Pandurangan, M. et al., "A novel approach for in vitro meat production," Applied Microbiology and Biotechnology, vol. 99, May 14, 2015, pp. 5391-5395.
Schütte, U. et al., "Hippo Signaling Mediates Proliferation, Invasiveness, and Metastatic Potential of Clear Cell Renal Cell Carcinoma," Translational Oncology, vol. 7, Iss. 2, Apr. 2014, pp. 309-321.
Zeng, Q. et al., "The Emerging Role of the Hippo Pathway in Cell Contact Inhibition, Organ Size Control, and Cancer Development in Mammals," Cancer Cell, vol. 13, Mar. 2008, pp. 188-192.
Zhao, B. et al., "Cell detachment activates the Hippo pathway via cytoskeleton reorganization to induce anoikis," Genes & Development, vol. 26, Jan. 2012, pp. 54-68.
Dong et al. "Elucidation of a Universal Size-Control Mechanism in *Drosophila* and Mammals," Cell 130, 1120-1133, Sep. 21, 2007.
International Search Report and Written Opinion issued by The International Searching Authority for Application No. PCT/US2018/031276, dated Sep. 10, 2018, 10 pages.
George et al. "Exploiting Expression of Hippo Effector, Yap, for Expansion of Functional Islet Mass," Molecular Endocrinology. Sep. 17, 2015 (Sep. 17, 2015), vol. 29, Iss. 11, pp. 1594-1607. entire document.
Watt et al. "Regulation of Tissue Growth by the Mammalian Hippo Signaling Pathway," Frontiers in Physiology. Nov. 24, 2017 (Nov. 24, 2017), vol. B, Article 942, pp. 1-12. entire document.
Addgene. "pBABE-hygro-hTERT." Plasmid #1773, Dec. 1998, 6 pages, [Online] [Retrieved Dec. 3, 2020], Retrieved from the Internet <UR: https://www.addgene.org/1773/>.
Addgene. "pBABE-neo-hTERT." Plasmid #1774, Dec. 1998, 5 pages, [Online] [Retrieved Dec. 4, 2020], Retrieved from the Internet <URL: https://www.addgene.org/1774/>.
Albini, S. et al., "Epigenetic Reprogramming of Human Embryonic Stem Cells into Skeletal Muscle Cells and Generation of Contractile Mvospheres," Cell Reports 3:661-670 (2013).
Animal Sake Farm Animals List. downloaded May 24, 2022; on the web at animalsake.com/farm-animals-list. pp. 1-10.
Baquero-Perez et al., "A Simplified but Robust Method for the Isolation of Avian and Mammalian Satellite cells," BMC Cell Biology 13(16): 1/11-11/11, (2012).
Barberi, T., et al., "Derivation of engraftable skeletal myoblasts from human embryonic stem cells," Nature Medicine 13(5):642-648(2007).
Barnes, et al., Advances in animal cell recombinant protein production: GS-NSO expression system, Cytotechnology 2000, vol. 32, pp. 109-123.

(56) References Cited

OTHER PUBLICATIONS

Bartholet, J., "Inside the Meat Lab a Handful of Scientists Aim to Satisfy the World's Growing Appetite for Steak Without Wrecking the Planet. The First Step: Grab a Petri Dish," Scientific American, pp. 65-69 (2011).
Bell et al., "Understanding TERT Promoter Mutations: A Common Path to Immortality," Mol Cancer Res 14:315-323 (2016). Published Online First Mar. 3, 2016, retrieved Jul. 6, 2017, from mcr.aacrjournals.org, 10 pages.
Bentzinger, C., et al., "Building Muscle: Molecular Regulation of Myogenesism," Cold Spring Harb Perspect Biol 4(2): 1-16 (2012).
Bernardes De Jesus et al., "The telomerase activator TA-65 elongates short telomeres and increases health span of adult/old mice without increasing cancer incidence," Aging Cell 10:604-621 (2011).
Bhagavati and Xu., "Generation Of Skeletal Muscle from Transplanted Embryonic Stem Cells in Dvstrophic Mice," Biochemical and Biophysical Research Communications 333:644-649 (2005).
Bhat and Bhat, "Animal-Free Meat Biofabrication," American Journal of Food Technology 6(6):441-459, (2011 ).
Bhat, Z.F. et al., "Prospectus of cultured meat—Advancing meat alternatives," Journal of Food Science and Technology 48(2), Apr. 2010, pp. 125-140.
Black, Brian L., and Eric N. Olson. "Transcriptional control of muscle development by myocyte enhancer factor-2 (MEF2) proteins" Annual review of cell and developmental biology 14.1 (1998): 167-196.
Blomberg et al. Twenty years of embryonic stem cell research in farm animals. Reproduction in Domestic Animals, vol. 47, Suppl. 4, pp. 80-85, Aug. 2012.
Boonen and Post, "The Muscle Stem Cell Niche: Regulation of Satellite Cells During Regeneration," Tissue Engineering—Part B: Reviews 14(4):419-431 (2008).
Canizo et al., "Exogenous human OKSM factors maintain pluripotency gene expression of bovine and porcine iPS-like cells obtained with STEMCCA delivery system," BMC Research Notes vol. 11, Article No. 509, Jul. 2018, 8 pages.
Cenciarelli et al., "Critical Role Played by Cyclin D3 in the Myod-Mediated Arrest of Cell Cycle During Myoblast Differentiation," Molecular and Cellular Biology 19(7):5203-5217 (1999).
Chang, et al., "Generation of Transplantable, Functional Satellite-Like Cells from Mouse Embryonic Stem Cells," FASEB J. 23, 1907-1919 (2009).
Chen et al. DNA methyltransferase inhibitor CDA-11 inhibits myogenic differentiation. Biochemical and Biophysical Research Communications, vol. 422, pp. 522-526, May 22, 2012.
Chen et al., "Potentiation of MyoD1 Activity By 5-Aza-2'-Deoxycytidine," Cell Growth & Differentiation, 1:383-392 (1990).
Chiu and Blau, "5-5Azacytidine Permits Gene Activation in a Previously Noninducible Cell Type," Cell, vol. 40, 417-424 (1985).
Choi, Sang-Woon, and Simonetta Friso. "Epigenetics: a new bridge between nutrition and health" Advances in nutrition 1.1 (2010): 8-16.
Cox et al., "Yap reprograms glutamine metabolism to increase nucleotide biosynthesis and enable liver growth," Nat. Cell. Biol. 18(8), Jan. 18, 2017, pp. 886-896.
Darabi, R., et al., "Perspective Lineage-Specific Reprogramming as a Strategy for Cell Therapy," Cell Cycle 7(12):1732-1737 (2008).
Darabi, R., et al., "Assessment of the Myogenic Stem Cell Compartment Following Transplantation of Pax3/Pax7-Induced Embryonic Stem Cell-Derived Progenitors," Lillehei Heart Institute, Department of Medicine, University of Minnesota, Minneapolis, MN, USA, 27 pages (2011).
Darabi, R., et al., Functional Skeletal Muscle Regeneration from Differentiating Embryonic Stem Cells, Nature and Medicine 14(2):134-143 (2008).
Datar and Betti, "Possibilities for an In Vitro Meat Production System," Innovative Food Science & Emerging Technologies 11(1):13-22(2010).
Davis, R., et al., " Expression of a Single Transfected cDNA Converts Fibmblasts to Myoblasts," Cell, vol. 51. 987-1000 (1987).

Dekel, I., et al., "Conditional Conversion of ES Cells to Skeletal Muscle by an Exogenous MyoDI Gene," (1992).
Delany, M. E. et al. "Telomeres in the Chicken: Genome Stability and Chromosome Ends." Poultry Science, vol. 82, No. 6, Jun. 1, 2003, pp. 917-926.
Desbois-Mouthon, Christele, et al. "Insulin and IGF-1 stimulate the.beta.- catenin pathway through two signalling cascades involving GSK-3.beta. inhibition and Ras activation" Oncogene 20.2 (2001): 252-259.
Ding, Vanessa MY, et al. "FGF-2 modulates Wnt signaling in undifferentiated hESC and iPS cells through activated PI3-K/GSK3. beta. signaling" Journal of cellular physiology 225.2 (2010): 417-428.
Dominguez et al., "Beyond editing: repurposing CRISPR-Cas9 for precision genome regulation and interrogation," Nature Reviews Molecular Cell Biology 17:5-15, Dec. 16, 2015.
Edelman, P., et al., "In Vitro-Cultured Meat Production," Tissue Engineering 11(5/6):659-662 (2005).
European Patent Office, Extended European Search Report and Opinion, EP Patent Application No. 18832585.6, dated Apr. 9, 2021, nine pages.
Extended European Search Report dated May 19, 2017, from the European patent Office for Application No. 14858383.4, filed Oct. 30, 2014, 10 pages.
Fan, L. et al., "The use of glutamine synthetase as a selection marker: recent advances in Chinese hamster ovary cell line generation processes," Pharmaceutical Bioprocessing 1(15), 2013, pp. 487-502.
Garrels et al. Ectopic expression of human telomerase KNA component results In increased telomerase activity and elongated telomeres in bovine blastocysts. Biol Reprod. 2012, 87(4):95, 1-7.
Genbank. "Bos Taurus Cyclin-Dependent Kinase 4, mRNA (cDNA Clone MGC: 133903 IMAGE:8041087), Complete CDS." NCBI, GenBank: BC109858.1, Nov. 2005, 2 pages, [Online] [Retrieved Dec. 7, 2020], Retrieved from the Internet <URL:https://www.ncbi.nlm.nih.gov/nuccore/BC109858>.
Genbank. "Gallus Gallus Gallus Telomerase Reverse Transcriptase (TERT) mRNA, Complete CDS." GenBank: NCBI, AY502592.1, 2004, 3 pages, [Online] [Retrieved Dec. 7, 2020], Retrieved from the Internet <URL:https://www.ncbi.nlm.nih.gov/nuccore/AY502592>.
Genovese et al., "Enhanced Development of Skeletal Myotubes from Porcine Induced Pluripotent Stem Cells," Scientific Reports, vol. 7, Feb. 6, 2017, 12 pages.
Gianakopoulos, P., et al., "MyoD Directly Up-regulates Premyogenic Mesoderm Factors during Induction of Skeletal Myogenesis in Stem Cells," The Journal of Biological Chemistry 286(4):2517-2525 (2011).
Good Food Institute, "Deep Dive: Cultivated Meat Cell Lines," Feb. 25, 2021, 13 pages, [Online] [Retrieved on Oct. 25, 2022] Retrieved from the Internet <URL: https://gfi.org/science/the-science-of-cultivated-meat/deep-dive-cultivated-meat-cell-lines/>.
Goudenege, S., et al., "Myoblasts Derived From Normal hESCs and Dystrophic hiPSCs Efficiently Fuse With Existing Muscle Fibers Following Transplantation," Molecular Therapy 20(11):2153-2167 Nov. 2012 (2012).
Hanas et al. Potentiation of myogenesis by 5-azacytidine. Journal of Cell Biology, vol. 91, No. 2, p. 27, Abstract 1051, Nov. 1981.
Harley, "Telomerase is not an oncogene," Oncogene 2002, 21(4):494-502.
He Rong et al., "Expression and clinical significance of p15 protein, mRNA in nasopharyngeal carcinoma," Chinese Journal of Laboratory Diagnosis, vol. 13, No. 5, Jun. 19, 2009, pp. 618-622, (with English abstract).
Hollenberg, S., et al., "Use of a conditional MyoD transcription factor in studies of MyoD trans-activation and muscle determination," Proc. Natl. Acad. Sci. USA vol. 90, pp. 8028-8032 (1993).
Hopkins and Dacey, "Vegetarian meat: Could Technology Save Animals and Satisfy Meat Eaters?" Journal of Agricultural and Environmental Ethics 21(6):579-596 (2008).
Hu, Yang "Exercise molecule biology," Beijing Sport University press, pp. 152-157 (2013) (with the English translation of paragraph 2 on p. 152 to paragraph 1 on p. 157).

(56) References Cited

OTHER PUBLICATIONS

Huang et al. "Zfp423 Promotes Adipogenic Differentiation of Bovine Stromal Vascular Cells," Plos One, Oct. 2012, vol. 7, Issue 10, 10 pages.

Hupkes et al. Epigenetics: DNA demethylation promotes skeletal myyotube maturation. The FASEB Journal, vol. 25, No. 11, pp. 3861-3872, Nov. 2011.

Hupkes, Marlinda, et al. "DNA methylation restricts spontaneous multi-lineage differentiation of mesenchymal progenitor cells, but is stable during growth factor-induced terminal differentiation" Biochimica et Biophysica Acta (BBA)-Molecular Cell Research 1813.5 (2011): 839-849.

Hwang, Y., et al., "Directed In Vitro Myogenesis of Human Embryonic Stem Cells and Their In Vivo Engraftment, " Plos One e72023 8(8):1-10 (2013).

Iacovino, M., et al., "Inducible Cassette Exchange: A Rapid and Efficient System Enabling Conditional Gene Expression in Embryonic Stem and Primary Cells," Stem Cells 2011;29:1580-1587 (2011).

Iemata, M., et al., "Suppression by Glutamate of Proliferative Activity Through Glutathione Depletion Mediated by the Cystine/Glutamate Anti porter in Mesenchymal C3H10T1/2 Stem Cells," Journal of Cellular Physiology 213:721-729 (2007).

International Preliminary Report on Patentability in corresponding PCT Application No. PCT/US2014/063250, dated May 3, 2016.

International Search Report and Written Opinion issued by The International Searching Authority for Application No. PCT/US14/63250, dated Jan. 21, 2015, 9 pages.

International Search Report and Written Opinion issued by the International Searching Authority for Application No. PCT/US2017/13782, dated Apr. 10, 2017, 7 pages.

International Search Report and Written Opinion issued by the International Searching Authority for Application No. PCT/US2018/042187, dated Nov. 1, 2018, 16 pages.

Jones, N., "A Taste of Things to Come?" Nature 468:752-753 (2010).

Kadim, I.T et al., "Cultured meat from muscle stem cells: A review of challenges and prospects," Journal of Integrative Agriculture 14(2), Feb. 2015, pp. 222-233.

Kanzaki et al. 2002; Telomerase rescues the expression levels of keratinocyte growth factor and insulin-like growth factor-II in senescent human fibroblasts. Environmental Cell Research. 279: 321-329.

Knox et al., "A streamlined implementation of the glutamine synthetase-based protein expression system," BMC Biotechnol. Sep. 2, 20134;13:74, 10 pages.

Langelaan, et al., "Meet the New Meat: Tissue Engineered Skeletal Muscle," Trends in Food Science & Technology 21(2):59-66 (2010).

Lassar, A., et al., "Transfection of a DNA Locus That Mediates the Conversion of IOTV2 Fibroblasts to Myoblasts," Cell 47:649-656 (1986).

Lavial et al., "Chicken Embryonic Stem Cells as a Non-Mammalian Embryonic Stem Cell Model," Development, Growth & Differentiation 52:101-1114 (2010).

Lee et al. "Establishment of an immortal chicken embryo liver-derived cell line," 2013 Poultry Science, vol. 92, No. 6, 9 pages.

Leung, M., et al., "Nanofiber-Based in Vitro System for High Myogenic Differentiation of Human Embryonic Stem Cells," Biomacromolecules 14:4207-4216 (2013).

Li et al., "Short-Term Serum-Free Culture Reveals That Inhibition of Gsk3beta Induces the Tumor-Like Growth of Mouse Embryonic Stem Cells," 6(6):1/10-10/10 (2011).

Li, J., "Cultured Meat: Growing Meat in the Lab," Berkeley Scientific Journal, vol. 26, Issue 1, Fall 2021, pp. 67-70.

Lian et al., Directed Cardiomyocyte Differentiation From Human Pluripotent Stem Cells by Modulating WnVBeta-Catenin Signaling Under Fully Defined Conditions. Nature Protocols, 8(1 ): 162-175 (2013).

Liu et al., "Linking Telomere Regulation to Stem Cell Pluripotency," Trends in Genetics 33(1), Jan. 2017, 16-33.

Maak et al., "Identification and Analysis of Putative Regulatory Sequences for the MYF5/MYF6 Locus in Different Vertebrate Species," Gene, 379: 141-147 (2006).

Mahmood, A., Enhanced Differentiation of Human Embryonic Stem Cells to Mesenchymal Progenitors by Inhibition ofTGF-beta/Activin/Nodal Signaling Using SB-431542 Journal of Bone and Mineral Research 25(6):1216-1233 (2010).

McFarlane et al., "Myostatin Signals Through Pax? To Regulate Satellite Cell Self-Renewal," Experimental Cell Research 314:317-329 (2008), available online Sep. 2007.

Minzuno, Y., et al., "Generation of Skeletal Muscle Stem/Progenitor Cells from Murine Induced Pluripotent Stem Cells," The FASEB Journal 24:2245-2243 (2010).

Molkentin et al. Cooperative activation of muscle gene expression by MEF2 and myogenic bHLH proteins. Cell, vol. 83, pp. 1125--1136, Dec. 1995.

Munro, et al. Histone deacetylase inhibitors induce a senescence-like state in human cells by a p16-dependent mechanism that is independent of a mitotic clock. Exp Cell Res. 2004 295(2):525-538.

Nagashima et al., "The Hippo Pathway as Drug Targets in Cancer Therapy and Regenerative Medicine," Current Drug Targets, vol. 18, Mar. 2017, pp. 447-454.

Noh et al., "Reduction of ammonia and lactate through the coupling of glutamine synthetase selection and downregulation of lactate dehydrogenase-A in CHO cells," Appl Microbial Biotechnol. Feb. 2017; 101(3): 1035-1045.

Nowak-Lmialek et al. Pluripotent cells in farm animals: state of the art and future perspectives. Reproduction, Fertility and Development, vol. 25, No. 1, pp. 103-108, 2012. (Year: 2012).

Ozasa et al., "Efficient Conversion of ES Cells into Myogenic Lineage Using the Gene-Inducible System," Biochemical and Biophysical Research Communications 357: 957-963 (2007).

Paredes, C. et al., "Modification of glucose and glutamine metabolism in hybrid om a cells through metabolic engineering," Cytotechnology, vol. 30, Jul. 1999, pp. 85-93.

Park et al. "Generation of porcine induced pluripotent stem cells and evaluation of their major histocompatibility complex protein expression in vitro." Veterinary Research Communications, vol. 37, No. 4, pp. 293-301, Dec. 2013, published online Aug. 23, 2013. (Year: 2013).

Post, M., "Cultured beef: Medical Technology to Produce Food," Journal of the Science of Food and Agriculture 94(6), Apr. 2014, pp. 1039-1041.

Post, M., "Cultured Meat from Stem Cells: Challenges and Prospects," Meat Sci. 92(3), Nov. 2012, pp. 297-301.

Rao, L., et al., "Highly Efficient Derivation of Skeletal Myotubes from Human Embryonic Stem Cells," Stem Cell Rev and Rep 8:1109-1119 (2012).

Rezanejad et al., Induced pluripotent stem cells: Progress and future perspectives in the stem cell world. Cellular Reprogramming 14(6), Dec. 2012, pp. 459-470.

Rinkevich, B. Cell cultures from marine invertebrates: New insights for capturing endless sternness. Marine Biotechnology (New York, N.Y.), vol. 13, No. 3, pp. 345-354, Jun. 2011, Epub Jan. 7, 2011.

Rohwedel, J., et al., "Muscle Cell Differentiation of Embryonic Stem Cells Reflects Myogenesis In Vivo: Developmentally Regulated Expression of Myogenic Determination Genes and Functional Expression of Ionic Currents.," Dev Biol. 164(1):87-101 (1994). (Abstract).

Rommel, C., "Mediation of IGF-1-Induced Skeletal Myotube Hypertrophy by PI(3)K/AkVmTOR and PI(3)K/AkVGSK3 Pathways," Nature Cell Biology 3:1009-1013 (2001).

Ryan, T., "Retinoic Acid Enhances Skeletal Myogenesis in Human Embryonic Stem Cells by Expanding the Premyogenic Progenitor Population," Stem Cell Rev and Rep 8, Jun. 2012, pp. 482-493.

Sakurai, H., et al., "Bidirectional Induction Toward Paraxial Mesodermal Derivatives from Mouse ES Cells In Chemically Defined Medium," Stem Cell Research 3:157-169 (2009).

Sakurai, H., et al., "Paraxial Mesodermal Progenitors Derived from Mouse Embryonic Stem Cells Contribute to Muscle Regeneration via Differentiation into Muscle Satellite Cells," Stem Cells 26:1865-1873 (2008).

(56) References Cited

OTHER PUBLICATIONS

Salani, S., et al., "Generation of Skeletal Muscle Cells from Embryonic and Induced Pluripotent Stem Cells as an In Vitro Model and for Therapy of Muscular Dystrophies," J. Cell. Mol. Med. 16(7), Jul. 2012, pp. 1353-1364.
Sasaki, T., et al., "Generation of a Multi-Layer Muscle Fiber Sheet from Mouse ES Cells by the Spermine Action at Specific Timing and Concentration," Differentiation 76, Dec. 2008, pp. 1023-1030.
Schnapp, Esther, et al. "Induced early expression of mrf4 but not myog rescues myogenesis in the myod/myf5 double-morphant zebrafish embryo" Journal of Cell Science 122.4, Feb. 15, 2009, pp. 481-488.
Sharpless, et al. Forging a signature of in vivo senescence. Nature Reviews Cancer, Jul. 2015, 15(7):397-408.
Stadler, G. et al. "Establishment of Clonal Myogenic Cell Lines from Severely Affected Dystrophic Muscles—CDK4 Maintains the Myogenic Population." Skeletal Muscle, vol. 1, Article 12, Mar. 2011, pp. 1-10.
Tako, E. et al. "Using the Domestic Chicken (*Gallus gallus*) as an In Vivo Model for Iron Bioavailability." Poultry Science, vol. 89, No. 3, Mar. 1, 2010, pp. 514-521.
Tan et al., "Efficient Derivation of Lateral Plate and Paraxial Mseoderm Subtypes From Human Embryonic Stem Cells Through GS Kimediated Differentiation," Stem Cells and Development 22(13), Jul. 2013, pp. 1893-1906.
Tanaka, et al., "Efficient and Reproducible Myogenic Differentiation from Human iPS Cells: Prospects for Modeling Miyoshi Myopathy In Vitro," Plos One e61540 8(4), Apr. 23, 2013, pp. 1-14.
Taylor et al. "Multiple new phenotypes induced in 10T 1 /2 and 3T3 cells treated with 5-azacytidine," Cell 17:771-779 (1979).
Telugu, B., et al., "Leukemia Inhibitory Factor (LIF)-dependent, Pluripotent Stem Cells Established from Inner Cell Mass of Porcine Embryos," Journal of Biological Chemistry, Aug. 2011, 286(33):28948-28953.
Telugu, B., et al., "Lif-Dependent, Pluripotent Stem Cells Established from Inner Cell Mass of Porcine Embryos," The American Society for Biochemistry and Molecular Biology, Inc., Downloaded from www.jbc.org at University of Missouri-Columbia, on Jul. 15, 2011.
Tseng et al. The GSK-3 inhibitor BIO promotes proliferation in mammalian cardiomyocytes. Chemistry & Biology, vol. 13, pp. 957-963, Sep. 2006.
Tuomisto, et al., "Environmental Impacts of Cultured Meat Production," Environ. Sci. Technol. 45(14):6117-6123 (2011).
Van Der Schaft, D., et al., "Engineering Skeletal Muscle Tissues from Murine Myoblast Progenitor Cells and Application of Electrical Stimulation," J. Vis. Exp. 73:1-6 (Mar. 2013).
Van Der Velden, J., et al., "Inhibition of Glycogen Synthase Kinase-3beta-activity is Sufficient to Stimulate Myogenic Differentiation," Am J Physiol Cell Physiol 290: C453-C462, (2006).
Van Der Weele et al. Cultured meat: every village its own factory?, Trends in Biotechnology, Jun. 2014, vol. 32, No. 6, 3 pages.
Van Der Weele, C., "In Vitro Meat," Encyclopedia of Food and Agricultural Ethics, Oct. 2014, pp. 1-8.
Van Der Weele, C., "In Vitro Meat: Promises and Responses: Cooperation Between Science, Social Research and Ethics," Global Food Security: Ethical and Legal Challenges: EurSafe 2010 Bilbao, Spain Sep. 16-18, 2010, pp. 507-512.
Vyas, D., et al., "GSK-3 Negatively Regulates Skeletal Myotube Hypertrophy," Am J Physiol Cell Physiol 283: C545-C551 (2002).
Wagers, A., "Want Not, Waste Not," Cell Stem Cell 2:6-7 (2008).
Wang et al., "Immortalization of chicken preadipocytes by retroviral transduction of chicken TERT and TR," (2017), Plos One 12(5): e0177348. retrieved May 9, 2017 at https://doi.org/10.1371/journal.pone.0177348.
Weintraub et al. Activation of muscle-specific genes in pigment, nerve, fat, liver and fibroblast cell lines by forced expression of MyoD. Proceedings of the National Academy of Sciences, USA, 86:5434-5438 (1989).
West et al. Porcine induced pluripotent stem cells produce chimeric offspring. Stem Cells and Development, vol. 19, No. 8, 2010, pp. 1211-1220, 2010. (Year: 2010).
Wilschut, K., et al., "Alpha 6 Integrin is Important for Myogenic Stem Cell Differentiation," Stem Cell Research 7: 112-123 (2011).
Wilschut, K., et al., "Extracellular Matrix Components Direct Porcine Muscle Stem Cell Behavior," Experimental Cell Research 316:341-352 (2010).
Wilschut, K., et al., "Isolation and Characterization of Porcine Adult Muscle-Derived Progenitor Cells," Journal of Cellular Biochemistry 105: 1228-1239 (2008).
Wootton et al. "Telomerase Alone Extends the Replicative Life Span of Human Skeletal Muscle Cells Without Compromising Genomic Stability," Human Gene Therapy, vol. 14, No. 15, Oct. 10, 2003, 15 pages.
Wu, G., et al., "Production and Supply of High-Quality Food Protein for Human Consumption: Sustainability, Challenges, and Innovations," Annals of the New York Academy of Sciences 1321 (1), Aug. 2014, pp. 1-19.
Xu et al., "Effects of glutamine and asparagine on recombinant antibody production using CHO-GS cell lines," Biotechnol Prog. Nov.-Dec. 2014;30(6):1457-68.
Yokoyama et al., "The Myogenic Transcriptional Network," Cellular and Molecular Life Sciences 68: 1843-1849 (2011).
Yu et al., "Chinese Disease Signal Pathway and Targeted Therapy," Anhui Science and Technology Press, p. 372 (2013) (with the English translation of paragraphs 4-8 on p. 372).
Zheng, J., K., et al., "Skeletal Myogenesis by Human Embryonic Stem Cells," Cell Research 713-722 (2006).
Zhu, C-H. et al. "Cellular Senescence in Human Myoblasts is Overcome by Human Telomerase Reverse Transcriptase and Cyclin-Dependent Kinase 4: Consequences in Aging Muscle and Therapeutic Strategies for Muscular Dystrophies." Aging Cell, vol. 6, No. 4, Aug. 2007, pp. 515-523.

\* cited by examiner

A

B

A

B ized growth of a cellular biomass within a cultivation infrastructure

COMPOSITIONS AND METHODS FOR INCREASING THE CULTURE DENSITY OF A CELLULAR BIOMASS WITHIN A CULTIVATION INFRASTRUCTURE

CROSS-REFERENCE TO RELATED APPLICATIONS

This application is a U.S. National Stage Application under 35 U.S.C. § 371 of International Application No. PCT/US2018/031276, filed May 5, 2018, which claims the benefit of U.S. Provisional Application No. 62/502,669, filed May 6, 2017, the disclosures of each of which are hereby incorporated by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MPHM-002-01US-seqlisting.txt, date recorded: Oct. 31, 2019, file size ~67,289 bytes).

BACKGROUND OF THE INVENTION

The mass production of cells remains limited by several factors, thus limiting final yields. Such mass production finds several downstream applications.

For example, foods formulated from metazoan cells, cultured in vitro, have prospective advantages over potential advantages over their corporal-derived animal counterparts, including improved nutrition and safety. Production of these products have been projected to require fewer resources, convert biomass a higher caloric efficiency and result in reduced environmental impacts relative to conventional in vivo methods. Together, metazoan cells, and their extracellular products, constitute a biomass that can potentially be harvested from a cultivation infrastructure for formulation of cell-based food products, such as cultured meat. Cellular biomass produced by cell culture method can also be used in medical applications such as organ or tissue transplant and grafts.

However, mass production of a cellular biomass originating from cultured metazoan cells remains limited by several factors, for example the maximum culture density that can be conventionally achieved, thus limiting final yields. Provided herein are compositions and methods that address this and other related needs.

BRIEF SUMMARY OF THE INVENTION

Provided are compositions and methods for increasing the culture density and thickness of a metazoan cellular biomass (also referred to herein as simply "biomass") in a cultivation infrastructure. These methods comprise inhibiting the HIPPO signaling pathway, for example, by activating Yes-Associated Protein 1 (YAP1) and/or Transcriptional Co-Activator with PDZ-binding motif (TAZ or WWTR1) or homologs thereof, or by inhibiting Mps One Binder kinase activator 1 (MOB1), Large Tumor Suppressor 1 (LATS1) kinase, LATS2 kinase, WW45, Macrophage Stimulating 1 (MST1) kinase, and/or MST2 kinase or homologs thereof in the cellular biomass.

Provided are compositions and methods for increasing the culture density of a cellular biomass in a cultivation infrastructure, for increasing the thickness of a cellular biomass in a cultivation infrastructure, and/or for promoting/increasing anchorage-independent growth of a cellular biomass in a cultivation infrastructure, and/or for promoting/increasing growth of a cellular biomass in a cultivation infrastructure in the absence of serum.

In some embodiments, provided are compositions and methods for increasing cell proliferation, for increasing the culture density of a cellular biomass in a cultivation infrastructure, for increasing the thickness of a cellular biomass in a cultivation infrastructure, and/or for promoting/increasing anchorage-independent growth of a cellular biomass in a cultivation infrastructure in the absence of serum.

In one aspect, provided herein is a method for increasing the thickness of a cellular biomass comprising: (a) culturing a metazoan cellular biomass in a cultivation infrastructure; and (b) inhibiting the HIPPO signaling pathway in the cellular biomass. In another aspect, provided herein is a method for increasing the density of a metazoan cellular biomass comprising: (a) culturing a metazoan cellular biomass in a cultivation infrastructure; and (b) inhibiting the HIPPO signaling pathway in the cellular biomass. In another aspect, provided herein is a method for anchorage-independent cell growth comprising: (a) culturing a metazoan cellular biomass in a cultivation infrastructure; and (b) inhibiting the HIPPO signaling pathway in the cellular biomass.

In some embodiments, inhibiting the HIPPO signaling pathway comprises activating Yes-Associated Protein 1 (YAP1) and/or Transcriptional co-Activator with PDZ-binding motif (TAZ) or homologs thereof in the cellular biomass. In some embodiments, inhibiting the HIPPO signaling pathway comprises inhibiting MOB1, LATS1 kinase, LATS2 kinase, WW45, MST1 kinase, and/or MST2 kinase or homologs thereof in the cellular biomass.

In some embodiments, the inhibiting a HIPPO signaling pathway comprises contacting the cellular biomass with one or more of serum, lysophosphatidic acid, sphingosine-1-phosphate, and thrombin.

In one aspect, the HIPPO signaling pathway is inhibited to provide a culture density of about $10^5$ cells/mL to about $10^{10}$ cells/mL in the cultivation infrastructure. In another aspect, the HIPPO signaling pathway is inhibited to provide a culture density of about 1.0 g/L to about 1000 g/L in the cultivation infrastructure.

In one aspect, the HIPPO signaling pathway is inhibited to provide a thickness of about 10 μm to about 2 mm to cellular biomass in the cultivation infrastructure.

In one aspect, provided herein is a method for increasing the thickness of a cellular biomass comprising: (a) culturing a metazoan cellular biomass in a cultivation infrastructure; and (b) activating Yes-Associated Protein 1 (YAP1) and/or Transcriptional co-Activator with PDZ-binding motif (TAZ) or homologs thereof in the cellular biomass. In another aspect, provided herein is a method for increasing the density of a metazoan cellular biomass comprising: (a) culturing a metazoan cellular biomass in a cultivation infrastructure; and (b) activating Yes-Associated Protein 1 (YAP1) and/or Transcriptional co-Activator with PDZ-binding motif (TAZ) or homologs thereof in the cellular biomass. In another aspect, provided herein is a method for anchorage-independent cell growth comprising: (a) culturing a metazoan cellular biomass in a cultivation infrastructure; and (b) activating Yes-Associated Protein 1 (YAP1) and/or Transcriptional co-Activator with PDZ-binding motif (TAZ) or homologs thereof in the cellular biomass.

In some embodiments, activating YAP1 and/or TAZ comprises contacting the cellular biomass with one or more of serum, lysophosphatidic acid, sphingosine-1-phosphate, and thrombin. In some embodiments, YAP1 and/or TAZ are activated in serum-free conditions. In some embodiments, activating YAP1 and/or TAZ comprises modifying one or more mechanical factors selected from substrate elasticity, substrate rigidity, confinement, stretching, and shear stress.

In some embodiments, activating YAP1 comprises increasing cellular expression of YAP1. In some embodiments, activating TAZ comprises increasing cellular expression of TAZ. In some embodiments, activating YAP1 and TAZ comprises increasing cellular expression of YAP1 and TAZ. In some embodiments, the YAP1 is wild-type YAP1. In some embodiments, the YAP1 comprises one or more mutations in the region targeted by LATS1 and/or LATS2 kinase activity. In some embodiments, the YAP1 comprises one or more mutations at residues corresponding to S5, S61, S109, S127, S163, S164, and S318 in the human YAP1 protein. In some embodiments, the YAP1 comprises one or more of S5A, S61A, S109A, S127A, S163A, S164A, and S318A mutations, residue numbers corresponding to the human YAP1 protein. In some embodiments, the TAZ is wild-type TAZ. In some embodiments, the TAZ comprises one more mutations in the region targeted by LATS1 and/or LATS2 kinase activity. In some embodiments, the TAZ comprises a mutation at a residue corresponding to S89 in the human TAZ protein. In some embodiments, the TAZ comprises a S89A mutation, the residue number corresponding to the human TAZ protein.

In one aspect, provided herein is a method for increasing the thickness of a cellular biomass comprising: (a) culturing a metazoan cellular biomass in a cultivation infrastructure; and (b) inhibiting MOB1, LATS1 kinase, LATS2 kinase, WW45, MST1 kinase, and/or MST2 kinase or homologs thereof in the cellular biomass. In another aspect, provided herein is a method for increasing the density of a metazoan cellular biomass comprising: (a) culturing a metazoan cellular biomass in a cultivation infrastructure; and (b) inhibiting MOB1, LATS1 kinase, LATS2 kinase, WW45, MST1 kinase, and/or MST2 kinase or homologs thereof in the cellular biomass. In another aspect, provided herein is a method for anchorage-independent cell growth comprising: (a) culturing a metazoan cellular biomass in a cultivation infrastructure; and (b) inhibiting MOB1, LATS1 kinase, LATS2 kinase, WW45, MST1 kinase, and/or MST2 kinase or homologs thereof in the cellular biomass.

In some embodiments, inhibiting MOB1, LATS1 kinase, LATS2 kinase, WW45, MST1 kinase, and/or MST2 kinase or homologs thereof comprises manipulating cells of the cellular biomass to introduce insertion or deletion mutations in the genes encoding these proteins. In some embodiments, inhibiting MOB1, LATS1 kinase, LATS2 kinase, WW45, MST1 kinase, and/or MST2 kinase or homologs thereof comprises over-expressing dominant negative mutants of these proteins in the cells of the cellular biomass.

In some embodiments, the cellular biomass is adherent to a substrate. In some embodiments, the substrate is impermeable. In such embodiments, the biomass thickness is measured as a minimum distance between a basal plane of the cellular biomass and an apical plane of the cellular biomass, e.g. at the region of interest. In some embodiments, the substrate is permeable. In such embodiments, the biomass thickness is measured as half of a minimum distance between a basal plane of the cellular biomass and an apical plane of the cellular biomass, e.g. at the region of interest.

In some embodiments, the cellular biomass is cultured in a suspension culture, and forms a self-adherent aggregate. In such embodiments, the biomass thickness is measured as half a minimum distance between opposing apical planes of the cellular biomass, e.g. at the region of interest. In some embodiments, the cellular biomass is cultured in a suspension culture as a single cell suspension that may remain as a single cell suspension even after increasing the culture density by inhibiting HIPPO signaling or the cellular biomass may start as a single cell suspension and form self-adherent aggregates after increasing the culture density by inhibiting the HIPPO signaling.

In some embodiments, the cellular biomass comprises cells from a livestock, poultry, game, or aquatic species. In some embodiments, the cellular biomass comprises myogenic cells.

In some embodiments, cell proliferation within the cellular biomass is increased through inhibition of HIPPO signaling. In some embodiments, cell survival within the cellular biomass is increased through inhibition of HIPPO signaling. In some embodiments, growth of the cellular biomass (for example, cell number) is increased by inhibiting HIPPO signaling. In some embodiments, cell proliferation, survival and growth are increased within the cellular biomass without addition of serum.

DETAILED DESCRIPTION OF THE INVENTION

Figure 1:
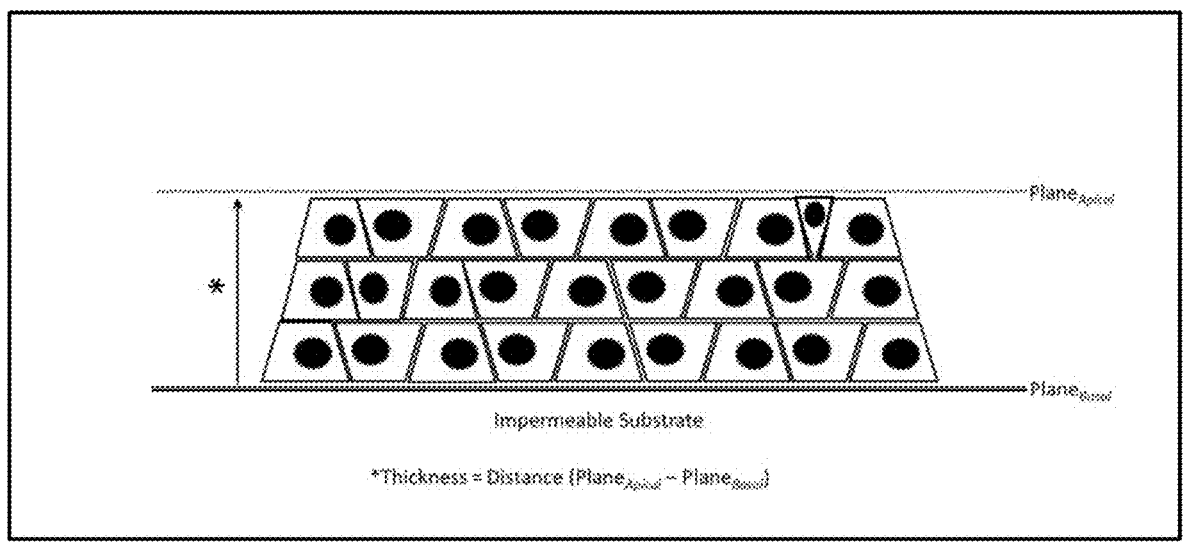
FIG. 1 depicts an exemplary embodiment where a cellular biomass is cultivated on a substrate impermeable to physiological solutions.

Provided are compositions and methods for increasing the density of a metazoan cellular biomass in a cultivation infrastructure; for increasing the thickness of a cellular biomass in a cultivation infrastructure; and for promoting anchorage-independent growth of a cellular biomass in a cultivation infrastructure. These methods comprise inhibiting the HIPPO signaling pathway, e.g. by (a) activating Yes-Associated Protein 1 (YAP1) and/or Transcriptional Co-Activator with PDZ-binding motif (TAZ or WWTR1) or homologs thereof and/or (b) by inhibiting MOB1, LATS1 kinase, LATS2 kinase, WW45, MST1 kinase, and/or MST2 kinase or homologs thereof in the cellular biomass.

Also provided are compositions and methods for increasing proliferation of cells; for increasing the density of a metazoan cellular biomass in a cultivation infrastructure; for increasing the thickness of a cellular biomass in a cultivation infrastructure; and for promoting anchorage-independent growth of a cellular biomass in a cultivation infrastructure without the use of serum.

Also provided are compositions and methods for increasing proliferation of cells; for increasing the density of a metazoan cellular biomass in a cultivation infrastructure; for increasing the thickness of a cellular biomass in a cultivation infrastructure; and for promoting anchorage-independent growth of a cellular biomass in a cultivation infrastructure in the presence of serum.

Also provided are compositions and methods for producing edible metazoan cellular biomass or therapeutic metazoan cellular biomass comprising: (a) culturing a metazoan cellular biomass in a cultivation infrastructure and (b) increasing the density or the thickness of the metazoan cellular biomass in the cultivation infrastructure by inhibiting the HIPPO signaling pathway. The term "edible" cellular biomass as used herein encompasses raw or uncooked metazoan meat as well as partially or fully cooked metazoan meat. The term "therapeutic cellular biomass" or "cellular biomass for therapeutic purposes" as used herein encompasses cells, partial or whole tissue of a metazoan species, cells, partial or whole organ of a metazoan species, or a graft, prepared for and used in therapeutic, medical or cosmetic applications.

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery.

Cellular Biomass

As referred to herein, a cellular biomass is comprised of metazoan cells and their extracellular products. The cells can be primary cells, or cell lines. The methods provided herein are applicable to any metazoan cell in culture.

In some embodiments, the cellular biomass is harvested for the formulation of cell-based food products, such as cultured animal meat. The term "cultured meat" as used herein refers to uncooked or cooked meat produced using cell culture methods. In some embodiments, the methods utilize cells with the potential to differentiate into skeletal muscle.

In some embodiments, the cellular biomass is harvested for the formulation of cell-based therapeutic products, such as cultured cells, tissue, graft, or whole or part of an organ. Thus in some embodiments, the methods utilize cells with various lineages or sources. For example, the methods may utilize cells from heart, liver, kidney, pancreas, spleen, bladder, intestine, skin, embryo etc.

In certain embodiments, the cellular biomass comprises cells that are from livestock such as domestic cattle, pigs, sheep, goats, camels, water buffalo, rabbits and the like. In certain embodiments, the cellular biomass comprises cells that are from poultry, e.g. domesticated poultry, such as chicken, turkeys, ducks, geese, pigeons and the like. In certain embodiments, the cellular biomass comprises cells that are from game species such as wild deer, gallinaceous fowl, waterfowl, hare and the like. In certain embodiments, the cellular biomass comprises cells that are from aquatic species or semi-aquatic species, including certain fish, crustaceans, mollusks, cephalopods, cetaceans, crocodilians, turtles, frogs and the like. In certain embodiments, the cellular biomass comprises cells that are from exotic, endangered, conserved or extinct animal species. In certain embodiments, the cellular biomass comprises cells that are from any metazoan species demonstrating the capacity for skeletal muscle tissue specification. In certain embodiments, the cellular biomass comprises cells that are modifiable by a genetic switch to induce rapid and efficient conversion of the cells to skeletal muscle for cultured meat production. In certain embodiments, the cellular biomass comprises cells that are from any metazoan species whose tissues are suitable for dietary consumption.

In specific embodiments, the cellular biomass comprises cells from *Gallus gallus, Bos taurus, Sous scrofa, Meleagris gallopavo, Anas platyrynchos, Salmo salar, Thunnus thynnus, Ovis aries, Coturnix coturnix, Capra aegagrus hircus*, or *Homarus americanus*.

In an exemplary embodiment, the cellular biomass comprises cells from livestock, poultry, game, or aquatic species.

In other embodiments, the cellular biomass comprises cells from humans, primates, rodents, including rats and mice, and companion animals such as dogs, cats, horses, and the like.

It is noted that the cellular biomass can be cultivated for any downstream application, not just limited to food production. For example, the cellular biomass can be cultivated for generating cells, a tissue or graft for therapeutic applications.

In some embodiments, the cells of the cellular biomass are primary stem cells or self-renewing stem cell lines.

In some embodiments, the cells of the cellular biomass are myoblasts, myocytes, fibroblasts, induced pluripotent stem cells, hepatocytes, mesenchymal stem cells, adipocytes, embryonic stem cells or chondrocytes.

In some embodiments, the cells of the cellular biomass are myogenic cells. In some embodiments, the cells are natively myogenic (e.g. are myogenic cells such as myoblasts, myocytes, satellite cells, side population cells, muscle derived stem cells, mesenchymal stem cells, myogenic pericytes, and mesoangioblasts that are cultured in the cultivation infrastructure). In other embodiments, the cells are not natively myogenic (e.g. are non-myogenic cells such as fibroblasts or non-myogenic stem cells that are cultured to become myogenic cells in the cultivation infrastructure).

In some embodiments, the cells of the cellular biomass are somatic cells. In some embodiments, the cells of the cellular biomass are not somatic cells.

In some embodiments, the cellular biomass comprises cells of the skeletal muscle lineage. Cells of the skeletal muscle lineage include myoblasts, myocytes, and skeletal muscle progenitor cells, also called myogenic progenitors, that include satellite cells, side population cells, muscle derived stem cells, mesenchymal stem cells, myogenic pericytes, and mesoangioblasts.

In some embodiments, the cellular biomass is cultivated in a suspension culture and forms a self-adherent aggregate. A self-adherent aggregate refers to masses of viable cells suspended in a physiological liquid medium (e.g. suspension culture) aggregated due to, for example, their (1) adherence to each other (e.g. cadherin cell adhesion) (2) adherence to a basement membrane or other extracellular matrix secreted by the cells (e.g. integrin cell adhesion) or (3) a combination of both.

Cultivation Infrastructure

As referred to herein, a cultivation infrastructure refers to the environment in which metazoan cells are cultured, i.e. the environment in which the cellular biomass is cultivated.

A cultivation infrastructure may be a tube, a cylinder, a flask, a petri-dish, a multi-well plate, a dish, a vat, an incubator, a bioreactor, an industrial fermenter and the like.

A cultivation infrastructure can be of any scale, and support any volume of cellular biomass and culturing reagents. In some embodiments, the cultivation infrastructure ranges from about 10 µL to about 100,000 L. In exemplary embodiments, the cultivation infrastructure is about 10 µL, about 100 µL, about 1 mL, about 10 mL, about 100 mL, about 1 L, about 10 L, about 100 L, about 1000 L, about 10,000 L, or even about 100,000 L.

In some embodiments, the cultivation infrastructure comprises a substrate. A cultivation infrastructure may comprise a permeable substrate (e.g. permeable to physiological solutions) or an impermeable substrate (e.g. impermeable to physiological solutions).

In some embodiments, the cultivation infrastructure comprises a primary substrate, which can be a flat, concave, or convex substrate. In some embodiments, the cultivation infrastructure further comprises a secondary substrate, either introduced, or autologous, to direct cellular growth between the substrates, e.g. to direct attachment, proliferation and hypertrophy of cells on a plane perpendicular to the primary substrate.

In some embodiments, the cultivation infrastructure comprises a hydrogel, a liquid cell culture media, or soft agar.

In some embodiments, the cultivation infrastructure does not comprise a substrate to which cells can adhere. In some embodiments, the cultivation infrastructure comprises a suspension culture, e.g. supporting the growth of a self-adhering biomass, or single-cell suspension in a liquid medium.

In some embodiments, the cultivation infrastructure comprises adherent cells (i.e. those cells that adhere to a substrate). In some embodiments, the cultivation infrastructure comprises non-adherent cells (i.e. those cells that do not adhere to a substrate). In some embodiments, the cultivation infrastructure comprises both adherent and non-adherent cells.

Culture Density

Mass production of cells remains limited by several factors. One such factor is the culture density, described here as the ratio of the amount of biomass harvestable to the volume of the cultivation infrastructure. Increasing the culture density of the biomass may result in increased yields per unit of infrastructure volume, thereby decreasing the infrastructure volume required to cultivate the desired product and the overall efficiency of the cultivation process.

A primary factor limiting the culture density is the maximum thickness of the cultivated biomass attainable by cells in culture, for example for reasons of contact inhibition. In some embodiments, the culture density is increased by increasing the thickness of the cultivated cellular biomass. The thickness of a cellular biomass is determined by the cultivation infrastructure in which it is grown. Planes of a cultivation infrastructure can be described as apical and basal. The apical plane is the interface of the biomass surface with an extracellular medium. The basal plane is the interface of the biomass with a primary substrate.

Due to cell-to-cell contact inhibition, metazoan cells, when cultured on a substrate in a cultivation infrastructure, generally form a monolayer and stop proliferating once they reach confluence. In some embodiments, methods of increasing the culture density or the thickness of a metazoan cellular biomass comprise culturing a metazoan cellular biomass on a substrate in a cultivation infrastructure; and forming stratified layers of cells by inhibiting the HIPPO signaling pathway, for example, by activating YAP1 and/or TAZ in the cellular biomass or by inhibiting MOB1, LATS1 kinase, LATS2 kinase, WW45, MST1 kinase, and/or MST2 kinase. For example, see FIGS. 1 and 2. Inhibition of the HIPPO signaling pathway and formation of stratified layers of cells of the cellular biomass may suppress cell death (i.e. apoptosis, anoikis) and lead to detachment of the cellular biomass from the substrate thereby promoting anchorage-independent growth.

Metazoan cells, when cultured in suspension in a cultivation infrastructure, may adhere to the top, bottom or sidewalls of the cultivation infrastructure. Provided herein are methods that support anchorage-independent growth in suspension, for example, by inhibiting cell death and/or inducing proliferation of single cells of a metazoan cellular biomass suspended in a suspension culture to induce, support or maintain anchorage-independent growth. For example, see FIG. 3 that shows an exemplary embodiment where a cellular biomass is cultivated in a suspension culture, as a self-adherent aggregate. Alternately, in cellular biomass is cultivated in suspension culture, as a single-cell suspension. Accordingly, in some embodiments, methods of increasing the culture density or the thickness of a metazoan cellular biomass comprise culturing a metazoan cellular biomass in suspension in a cultivation infrastructure; and forming multiple layers of cells of the cellular biomass on top of each other by inhibiting the HIPPO signaling pathway, for example, by activating YAP1 and/or TAZ or by inhibiting MOB1, LATS1 kinase, LATS2 kinase, WW45, MST1 kinase, and/or MST2 kinase in the cellular biomass.

Figure 2:
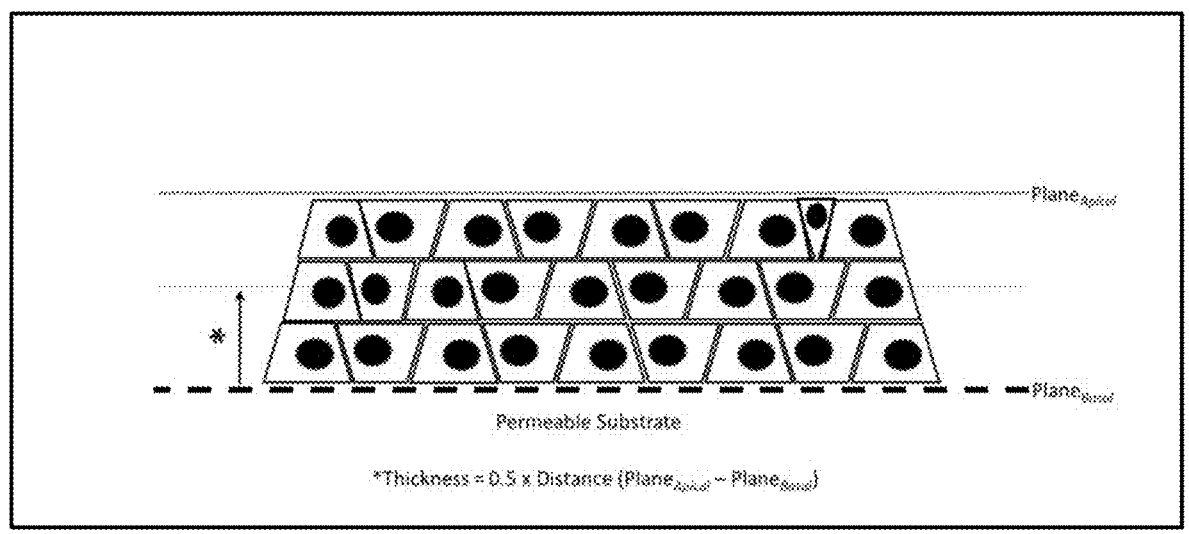
FIG. 2 depicts an exemplary embodiment where a cellular biomass is cultivated on a substrate permeable to physiological solutions.
Figure 3:
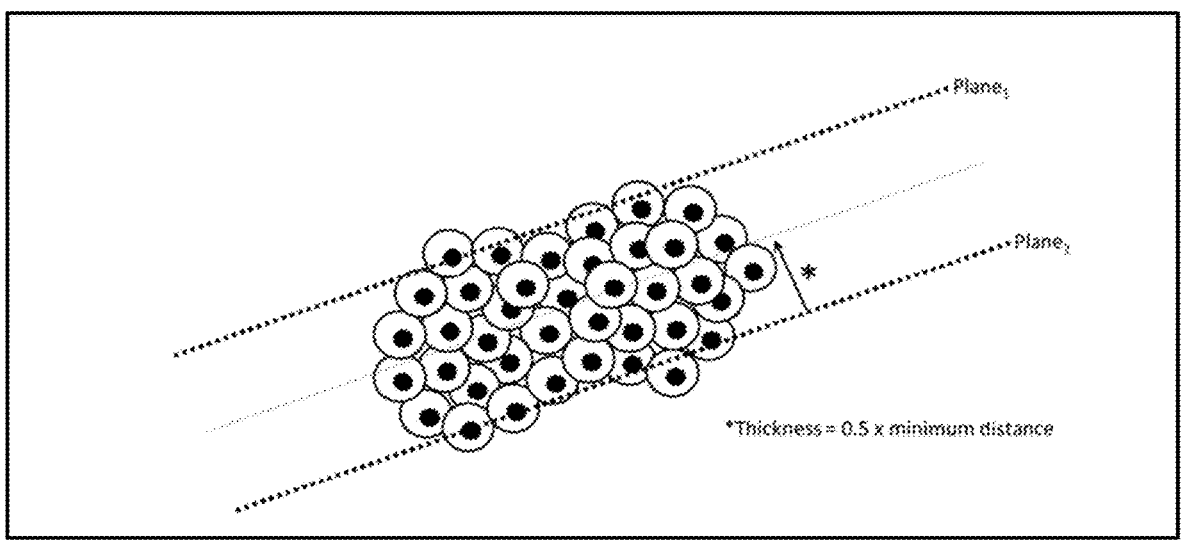
FIG. 3 depicts an exemplary embodiment where a cellular biomass is cultivated in a suspension culture, as a self-adherent aggregate.

In one embodiment, the methods described herein lead to the loss of contact inhibition of adherent cells. In various aspects, the methods can decrease contact inhibition by about 10%, 20%, 30%, 40%, 50%, 60%, 70%, 80%, 90%, or 100%, including values and ranges therebetween, compared to the methods where the HIPPO signaling is not inhibited.

Where a biomass is cultivated on a substrate impermeable to physiological solutions, the thickness of the cellular biomass is the distance between the basal and apical plane of the cultivated biomass (depicted in FIG. 1).

Where the biomass is cultivated on a permeable substrate, the thickness is a fraction (e.g. about half) of the distance between the basal and apical plane of the cultivated biomass (depicted in FIG. 2).

Where the biomass is cultivated in a suspension culture, as a self-adherent aggregate, the thickness is a fraction (e.g. about half) of the minimum distance between opposing apical planes (depicted in FIG. 3).

Accordingly, provided herein are compositions and methods to increase the culture density and thickness of a cellular biomass in a cultivation infrastructure. In some embodiments, increasing the culture density of the cellular biomass in the cultivation infrastructure results in an increased yield harvestable per unit volume of the cultivation infrastructure. For example, in some embodiments, increasing the culture density of the cellular biomass in the cultivation infrastructure results in an increased cell mass per unit volume of the cultivation infrastructure. In some embodiments, the method results in volumetric expansion of the biomass between the lower threshold, delimited by contact inhibition of cell growth at or near the basal plane, and the upper threshold, delimited by the maximal thickness attainable given the rate of diffusion of wastes and nutrients across the biomass. This volumetric expansion between the upper and lower threshold can be further promoted by the inclusion of a secondary substrate, either introduced, or autologous, to direct cellular growth between the substrates.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase in the cellular biomass as described in greater detail below), the culture density of the cellular biomass may reach about $10^5$ cells/mL, about $10^6$ cells/mL, about $10^7$ cells/mL, about $10^8$ cells/mL, about $10^9$ cells/mL, or about $10^{10}$ cells/mL (cells in the cellular biomass/mL of cultivation infrastructure), including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase in the cellular biomass as described in greater detail below), the culture density of the cellular biomass may reach about 1 g/L, 5 g/L, 10 g/L, 25 g/L, 50 g/L, 75 g/L, 100 g/L, 150 g/L, 200 g/L, 250 g/L, 300 g/L, 350 g/L, 400 g/L, 450 g/L, 500 g/L, 550 g/L, 600 g/L, 650 g/L, 700 g/L, 750 g/L, 800 g/L, 850 g/L, 900 g/L, or 1000 g/L (g of cellular biomass/L of cultivation infrastructure), including values and ranges therebetween. In some embodiments, the culture density of the cellular biomass may range from about 1 g/L to about 5 g/L, about 1 g/L to about 750 g/L, about 1 g/L to about 500 g/L, about 1 g/L to about 250 g/L, about 1 g/L to about 100 g/L, about 1 g/L to about 50 g/L, about 5 g/L to about 1000 g/L, about 5 g/L to about 750 g/L, about 5 g/L to about 500 g/L, about 5 g/L to about 250 g/L, about 5 g/L to about 100 g/L, about 5 g/L to about 50 g/L, about 25 g/L to about 1000 g/L, about 25 g/L to about 750 g/L, about 25 g/L to about 500 g/L, about 25 g/L to about 300 g/L, about 25 g/L to about 250 g/L, about 25 g/L to about 100 g/L, about 50 g/L to about 1000 g/L, about 50 g/L to about 750 g/L, about 50 g/L to about 500 g/L, about 50 g/L to about 300 g/L, about 50 g/L to about 250 g/L, about 100 g/L to about 1000 g/L, about 100 g/L to about 750 g/L, about 100 g/L to about 500 g/L, about 200 g/L to about 1000 g/L, about 200 g/L to about 750 g/L, about 200 g/L to about 500 g/L, about 300 g/L to about 1000 g/L, about 300 g/L to about 800 g/L, about 400 g/L to about 1000 g/L, or about 500 g/L to about 1000 g/L including values and ranges therebetween.

As provided herein, the culture density of the biomass in the cultivation infrastructure is determined by calculating the cell number per unit volume of the cultivation infrastructure, by determining the biomass per unit volume of the cultivation infrastructure, by determining the biomass DNA content per unit volume of the cultivation infrastructure, by determining the biomass RNA content per unit volume of the cultivation infrastructure, by determining the biomass protein content per unit volume of the cultivation infrastructure, or by visual, electronic, metabolic, spectroscopic, or microscopic, measurement of the biomass density.

In some embodiments, the culture density of the biomass in the cultivation infrastructure is calculated as the ratio of the amount of biomass harvestable to the volume of the cultivation infrastructure. In some embodiments, the culture density of the biomass in the cultivation infrastructure is calculated as the ratio of the amount of biomass harvestable to the volume of the culture medium used within the cultivation infrastructure. In some embodiments, by inhibiting the HIPPO signaling pathway in the cellular biomass, the ratio of the amount of biomass harvestable to the volume of the cultivation infrastructure is increased about 2 to 30 times, 2 to 25 times, 2 to 20 times, 2 to 15 times, 2 to 10 times, 5 to 30 times, 5 to 25 times, 5 to 20 times, 5 to 15 times, 5 to 50 times, 10 to 50 times, 10 to 40 times, 10 to 30 times, 10 to 20 times, including values and ranges therebetween, compared to the ratio obtained when the HIPPO signaling pathway is not inhibited. In some embodiments, the ratio is increased by about 2, 3, 4, 5, 6, 7, 8, 9, 10, 12, 15, 20, 25, 30, 35, 40, 45, or about 50 times, including values and ranges therebetween, compared to the ratio obtained when the HIPPO signaling pathway is not inhibited.

In some embodiments, the culture density and/or thickness of a cellular biomass where HIPPO signaling is inhibited is about 1.025 fold, 1.05 fold, 1.10-fold, 1.15-fold, 1.20-fold, 1.25-fold, 1.30 fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where HIPPO signaling is not inhibited.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, the thickness of the cellular biomass may reach from about 5 µm to about 400 µm, about 5 µm to about 350 µm, about 5 µm to about 300 µm, about 5 µm to about 250 µm, about 5 µm to about 200 µm, about 5 µm to about 150 µm, about 5 µm to about 100 µm, about 10 µm to about 400 µm, about 10 µm to about 350 µm, about 10 µm to about 300 µm, about 10 µm to about 250 µm, about 10 µm to about 200 µm, about 10 µm to about 150 µm, about 10 µm to about 100 µm, about 20 µm to about 400 µm, about 20 µm to about 350 µm, about 20 µm to about 300 µm, about 20 µm to about 250 µm, about 20 µm to about 200 µm, about 20 µm to about 150 µm, about 20 µm to about 100 µm, about 50 µm to about 500 µm, about 50 µm to about 450 µm, about 50 µm to about 400 µm, about 50 µm to about 350 µm, about 50 µm to about 300 µm, about 50 µm to about 250 µm, about 100 µm to about 500 µm about 100 µm to about 400 µm, about 100 µm to about 300 µm, or about 100 µm to about 250 µm. including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, the thickness of the cellular biomass may reach from about 10 µm to about 2 mm, about 10 µm to about 1.5 mm, about 10 µm to about 1 mm, about 10 µm to about 500 µm, about 50 µm to about 2 mm, about 50 µm to about 1.5 mm, about 50 µm to about 1 mm, about 50 µm to about 500 µm, about 100 µm to about 2 mm, about 100 µm to about 1.5 mm, about 100 µm to about 1 mm, about 100 µm to about 500 µm, about 150 µm to about 2 mm, about 150 µm to about 1.5 mm, about 150 µm to about 1 mm, or about 150 µm to about 500 µm, including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, the thickness of the cellular biomass may reach from 100 µm to about 20 mm, about 100 µm to about 15 mm, about 100 µm to about 10 mm, about 100 µm to about 5 mm, about 1 mm to about 20 mm, about 1 mm to about 15 mm, about 1 mm to about 10 mm, about 5 mm to about 20 mm, or about 5 mm to about 15 mm, including values and ranges therebetween. For example, in some embodiments, by inhibiting the HIPPO signaling pathway in the cellular biomass, the thickness of the cellular biomass may reach about 100 µm, 250 µm, 500 µm, 1 mm, 1.5 mm, 2 mm, 2.5 mm, 3 mm, 3.5 mm, 4 mm, 4.5 mm, or 5 mm, including values and ranges therebetween. In some embodiments, by inhibiting the HIPPO signaling pathway in the cellular biomass, the thickness of the cellular biomass may reach about 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, or 20 mm, including values and ranges therebetween.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, there is an increased yield of cellular biomass harvestable per unit volume of the cultivation infrastructure. In some embodiments, the increase is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000% compared to when there is no inhibition of the HIPPO signaling pathway in the cellular biomass.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, there is an increased yield of cellular biomass harvestable per unit volume of the cultivation infrastructure. In some embodiments, the increase is at least about 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold compared to when there is no inhibition of the HIPPO signaling pathway in the cellular biomass.

In some embodiments, inhibition of the HIPPO signaling pathway in the cellular biomass increases the culture density and/or thickness of the cellular biomass by increasing the rate of proliferation of cells of the cellular biomass. In some embodiments, the increase in the rate of cell proliferation is at least at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, including values and ranges therebetween, compared to when there is no inhibition of the HIPPO signaling pathway in the cellular biomass. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to when there is no induced inhibition of the HIPPO signaling pathway in the cellular biomass. In some embodiments, the cellular biomass is not adherent.

In some embodiments, inhibition of the HIPPO signaling pathway in the cellular biomass decreases cell death within the cellular biomass. In some embodiments, the decrease of cell death is at least at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, including values and ranges therebetween, compared to when there is no induced inhibition of the HIPPO signaling pathway in the cellular biomass. In some embodiments, decreased cell death within the cellular biomass is about 2.5-10%, about 2.5-75%, about 2.5-50%, about 5.0-100%, about 5.0-75%, about 5.0-50%, about 10-100%, about 10-75%, or about 10-50%, including values and ranges therebetween, compared to when there is no induced inhibition of the HIPPO signaling pathway in the cellular biomass. In some embodiments, the cellular biomass is not adherent.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase in the cellular biomass), there is an increase in density and thickness, with little or no contact inhibition of the proliferating cells in the biomass.

In some embodiments, by inhibiting the HIPPO signaling pathway (e.g., by activating YAP1, activating TAZ, or activating YAP1 and TAZ, or by inhibiting MOB1, LATS1 kinase, LATS2 kinase, WW45, MST1 kinase, and/or MST2 kinase) in the cellular biomass, there is an increase in density and thickness, with minimal impact on the rate of diffusion of wastes and nutrients across the biomass.

In some embodiments, methods for increasing the culture density of a metazoan cellular biomass in a cultivation infrastructure comprise: (a) culturing a metazoan cellular biomass in a cultivation infrastructure, and (b) inhibiting the HIPPO signaling pathway (e.g., by activating YAP1 and/or TAZ or homologs thereof, or by inhibiting MOB1, LATS1 kinase, LATS2 kinase, WW45, MST1 kinase, and/or MST2 kinase or homologs thereof) in the cellular biomass to provide a culture density of about $10^5$ cells/mL to about $10^{10}$ cells/mL in the cultivation infrastructure. In some embodiments, the step of inhibiting the HIPPO signaling pathway is carried out to provide a culture density of about 5 g/L to about 1000 g/L in the cultivation infrastructure. Ranges and values of culture densities that may be provided by the methods of the invention are described throughout this disclosure. Accordingly, in various embodiments, the step of inhibiting the HIPPO signaling pathway may be carried out to provide the ranges or values of culture densities described throughout this disclosure.

In some embodiments, methods for increasing the thickness of a metazoan cellular biomass in a cultivation infrastructure comprise: (a) culturing a metazoan cellular biomass in a cultivation infrastructure, and (b) inhibiting the HIPPO signaling pathway (e.g., by activating YAP1 and/or TAZ or homologs thereof, or by inhibiting MOB1, LATS1 kinase, LATS2 kinase, WW45, MST1 kinase, and/or MST2 kinase or homologs thereof) in the cellular biomass to provide a thickness of about 10 μm to about 2 mm in the cellular biomass in the cultivation infrastructure. Ranges and values of the thickness of cellular biomass that may be provided by the methods of the invention are described throughout this disclosure. Accordingly, in various embodiments, the step of inhibiting the HIPPO signaling pathway may be carried out to provide the ranges or values of thickness described throughout this disclosure.

Anchorage-Independent Growth

Provided herein are compositions and methods to promote/enhance anchorage-independent growth of a cellular biomass in a cultivation infrastructure. More specifically the methods promote/enhance the growth of cells that are typically anchorage-dependent in a suspension culture in an anchorage independent manner. These methods comprise inhibition of the HIPPO signaling pathway in the cellular biomass. FIG. 3 depicts the growth of a cellular biomass in an anchorage-independent context, in a suspension culture.

In some embodiments, methods to promote anchorage-independent growth of a cellular biomass in a cultivation infrastructure comprises: (a) culturing metazoan cells in a cultivation infrastructure; (b) antagonizing the HIPPO signaling pathway in the cells to increase the rate of cell proliferation (c) antagonizing the HIPPO signaling pathway to repress cell death. The rate of cell proliferation can be assessed, for example, by counting the number of cells in the S-phase. In some embodiments, an increase in the rate of cell proliferation and decrease in cell death promotes adherentt cells to transition to a non-adherent form. In some embodiments, an increase in the rate of cell proliferation and decrease in cell death promotes transition of anchorage-independent growth cells in cells from anchorage-dependent growth.

In one embodiment, inhibition of the HIPPO signaling pathway promotes anchorage-independent growth by increasing the rate of cell proliferation. In some embodiments, increase in the rate of cell proliferation is at least 2.5%, at least 5%, 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, including values and ranges therebetween, compared to when there is no inhibition of the HIPPO signaling pathway in the cellular biomass. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to when there is no inhibition of the HIPPO signaling pathway in the cellular biomass.

In one embodiment, the methods described herein promote anchorage-independent growth by decreasing cell-to-cell contact inhibition. In some embodiments, the decrease in contact inhibition provided by the present methods is about 10%, 20%, 30%, 40%, 50%, 60%, 70%, 80%, 90%, or 100%, including values and ranges therebetween, compared to the methods where the HIPPO signaling is not inhibited.

In one embodiment, the methods described herein promote anchorage-independent growth by decreasing cell death. In some embodiments, the decrease in contact inhibition provided by the present methods is about 2.5%, 5%, 10%, 20%, 30%, 40%, 50%, 60%, 70%, 80%, 90%, or 100%, including values and ranges therebetween, compared to the methods where the HIPPO signaling is not inhibited.

Methods

Provided herein are methods to increase the culture density in a cultivation infrastructure, to increase the thickness of a cellular biomass in a cultivation infrastructure, and/or to promote anchorage-independent growth of a cellular biomass. Also provided are methods of making edible or therapeutic cellular biomass comprising increasing the culture density or the thickness of a cellular biomass in a cultivation infrastructure.

In some embodiments, at least one step of the methods described herein can be carried out in the absence of serum. For example, by using serum-free media for culturing of the cells of a cellular biomass, for inhibiting the HIPPO signaling pathway, for differentiation of the cellular biomass, and/or for harvesting of the cellular biomass. In some embodiments, the entire method can be performed in serum-free conditions. In other embodiments, some steps are carried out in the absence of serum while some steps are carried out in the presence of serum. In some embodiments, provided herein are methods of increasing cell proliferation in the absence of serum.

In various embodiments, the methods of the present disclosure comprise inhibiting the HIPPO signaling pathway.

Inhibiting the HIPPO Signaling Pathway

In some embodiments, inhibiting the HIPPO signaling pathway comprises activating Yes-Associated Protein 1 (YAP1) or homologs thereof in the cellular biomass, activating Transcriptional Co-Activator with PDZ-binding motif (TAZ, WWTR1) or homologs thereof in the cellular biomass, or activating both YAP1 and TAZ or homologs thereof in the cellular biomass. In some embodiments, inhibiting the HIPPO signaling pathway comprises inhibiting a regulatory protein, Mps One Binder kinase activator 1 (MOB1) or homologs thereof, in the cellular biomass, inhibiting Large Tumor Suppressor kinase 1 (LATS1) or LATS2 kinase or homologs thereof in the cellular biomass, inhibiting MOB1 and either the LATS1 or LATS2 kinase or homologs thereof in the cellular biomass or inhibiting MOB1 and both LATS1 and LATS2 kinases or homologs thereof in the cellular biomass. In some embodiments, inhibiting the HIPPO signaling pathway comprises inhibiting a regulatory protein, WW45 or homologs thereof, in the cellular biomass, inhibiting Macrophage Stimulating 1 (MST1) kinase or MST2 kinase or homologs thereof in the cellular biomass, inhibiting WW45 and either the MST1 or MST2 kinase or homologs thereof in the cellular biomass or inhibiting WW45 and both MST1 and MST2 kinases or homologs thereof in the cellular biomass.

As contemplated herein, in some embodiments, the activation of YAP1 and TAZ or homologs thereof or the inhibition of MOB1, LATS1/2 kinases, WW45, and MST1/2 kinases or homologs thereof is at the gene level or the protein level. Accordingly, in the methods described herein, the YAP1, TAZ, MOB1, LATS1/2 kinases, WW45, and MST1/2 kinases or homologs thereof may be in the wild-type or mutant form.

In some embodiments, the HIPPO signaling pathway may be inhibited by adding a HIPPO signaling inhibitor to culture media. In some embodiments, HIPPO signaling inhibitors include animal serum, sphingosine-1-phosphate, thrombin, and lysophosphatidic acid. In some embodiments, HIPPO signaling may be inhibited by adding YAP1 and/or TAZ proteins (purified, synthetic, or recombinantly produced), recombinantly produced dominant negative mutants of MOB1, LATS1/2 kinases, WW45, and/or MST1/2 kinases, or combinations thereof.

Figure 14:
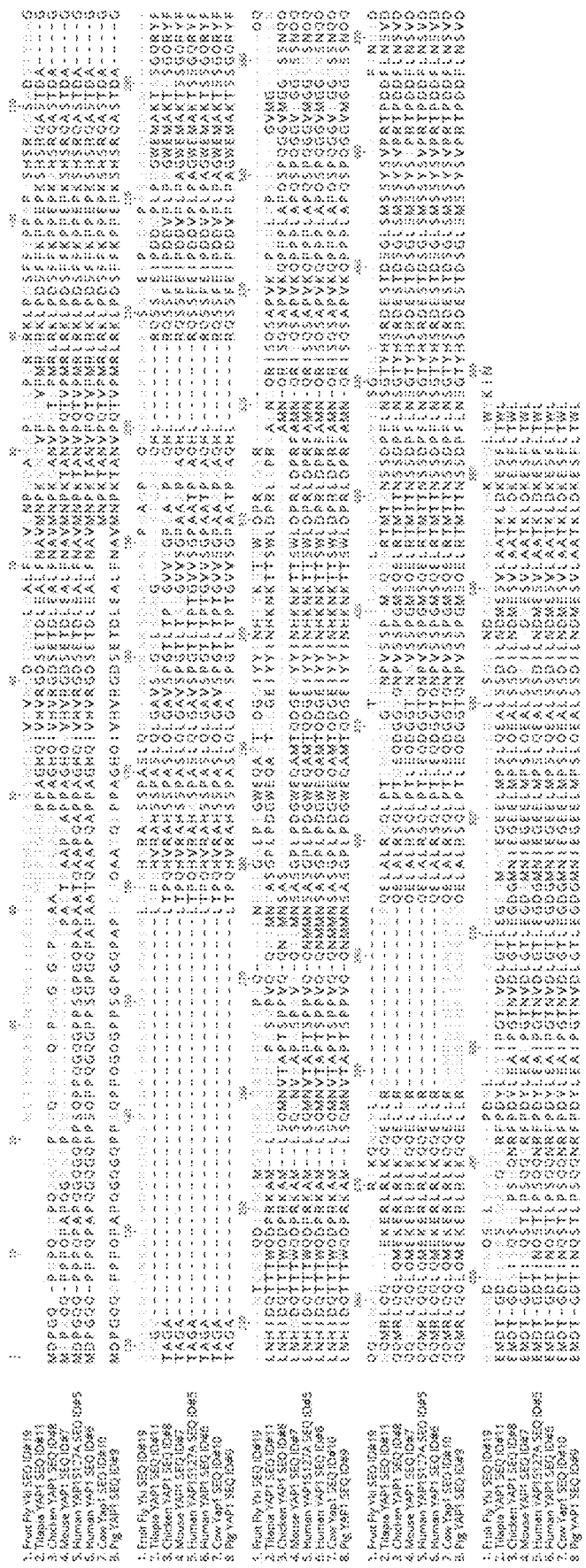
FIG. 14 shows amino acid residues that are conserved between YAP1 and its homologs from various species.
Figure 15:
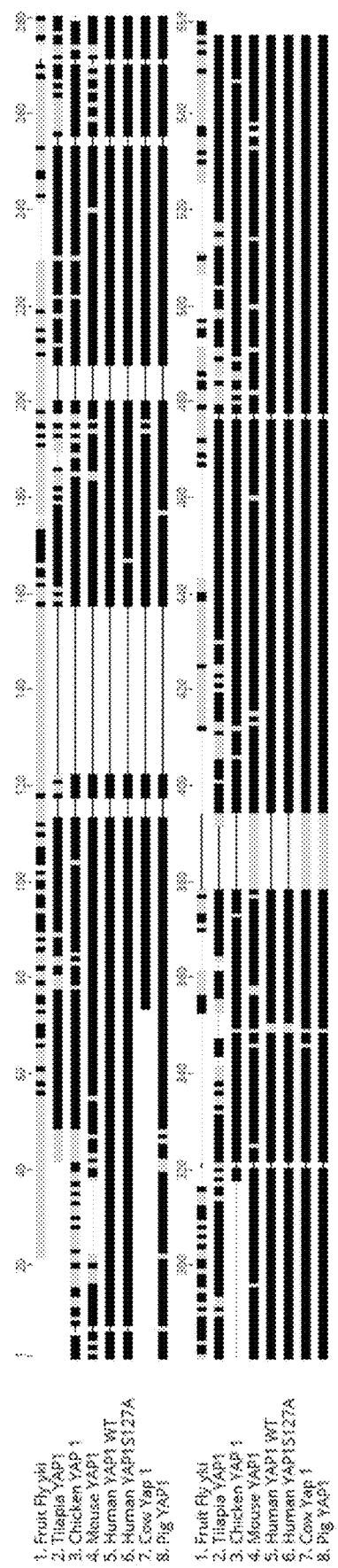
FIG. 15 shows the homology between YAP1 and its homologs from various species.
Figure 16:
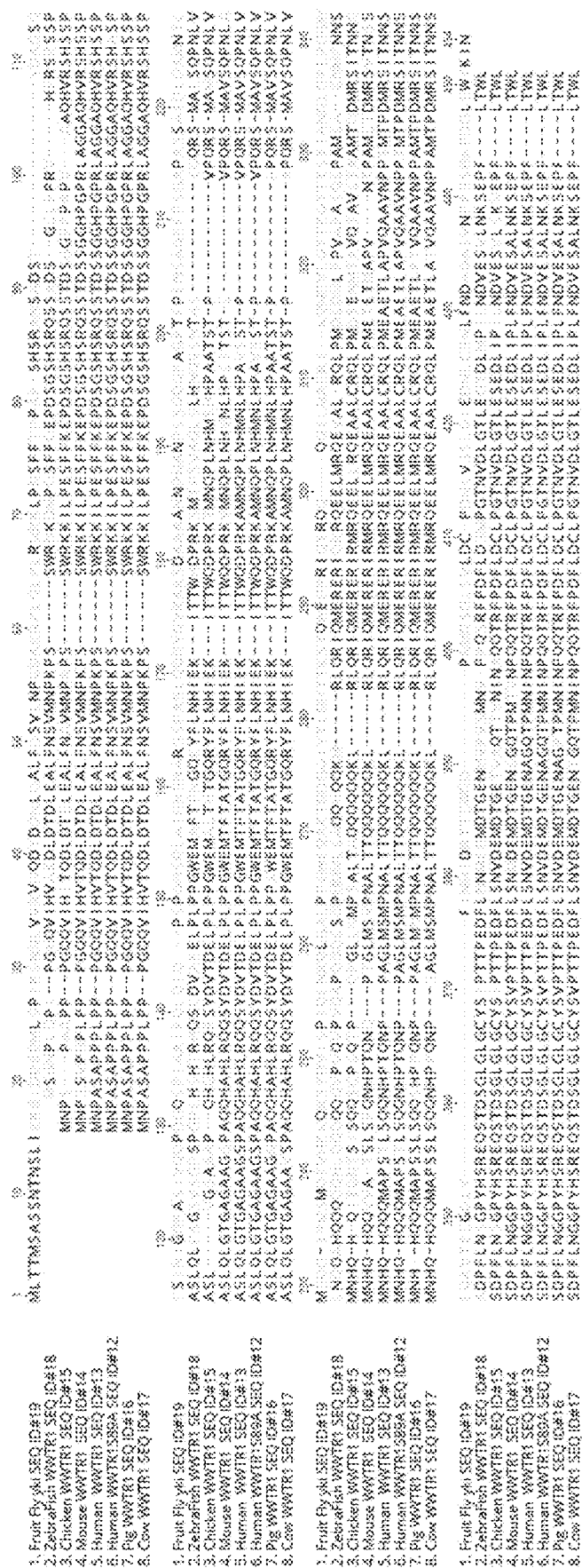
FIG. 16 shows amino acid residues that are conserved between WWTR1 and its homologs from various species.

In some embodiments, the HIPPO signaling may be inhibited by using or targeting homologs of YAP1, TAZ, MOB1, LATS1/2 kinases, WW45, and MST1/2 kinases. The term "homolog" as used herein encompasses orthologs (from different species) and paralogs (from the same species). In mammals, the YAP1 and TAZ proteins are expressed from the YAP1 and WWRT1 genes, respectively, and constitute paralogs of one another. Certain metazoan species, however, may not express proteins identified as YAP1 or TAZ, and instead express homologs of YAP1 and/or TAZ whose functions are conserved, in whole or in part, by YAP1 or TAZ. For instance, *Drosophila melanogaster* expresses a single homolog of YAP1 and WWTR1 genes, identified as the Yki gene, which encodes the transcriptional co-activator Yorkie protein. FIGS. 14 and 15 show conserved amino acid residues and protein domains of YAP1 and its homologs from various species. FIG. 16 shows conserved amino acid residues of WWTR1 and its homologs from various species. Although the homologs of YAP1 and/or TAZ are phylogenetically diverse, they show a high degree of conserved activity that is similar to YAP1 and TAZ. Therefore, many of these homolog proteins not identified as YAP1 or TAZ may be used to functionally substitute YAP1 or TAZ in the methods described herein. Accordingly, in some embodiments, methods disclosed herein may comprise activating one or more homologs of YAP1 and TAZ. Methods of activating YAP1 and/or TAZ are described in greater detail below. Similar methods can be used for activation of one or more homologs of YAP1 and TAZ.

Many metazoan species may not express MOB1, LATS1/2 kinases, WW45, and MST1/2 kinases; but instead express homologs of these proteins. For example, in *Drosophila melanogaster*, a single protein, Warts, is a homolog of the mammalian LATS1/2 proteins; a single protein, Mats, is a homolog of the mammalian MOB1 proteins; a single protein, Hippo, is a homolog for the mammalian MST1/2 proteins; and a single protein, Salvador, is a homolog of the mammalian WW45 protein. Accordingly, in certain embodiments, methods of the present disclosure may comprises inhibition of homologs of MOB1, LATS1/2 kinases, WW45, and MST1/2 kinases, such as Mats/Warts or Hippo/Salvador. For example, in embodiments, where the metazoan cellular biomass comprises cells with a genotype more closely akin to *Drosophila melanogaster*, the methods of increasing the culture density or the thickness of cellular biomass may comprise inhibiting Mats/Warts and/or Hippo/Salvador. Methods of inhibiting MOB1, LATS1/2 kinases, WW45, and MST1/2 kinases are described in greater detail below. Similar methods can be used for inhibiting one or more homologs of MOB1, LATS1/2 kinases, WW45, and MST1/2 kinases.

In some embodiments, inhibiting the HIPPO signaling pathway in the cellular biomass comprises inhibiting, at the gene or protein level, one or more non-canonical HIPPO signaling agonists such as aPKC, Tao1, Msn and/or PRP4k that are expressed, for example, in *Drosophila melanogaster*, or homologs thereof.

In embodiments, where the HIPPO signaling is inhibited by introducing into the cells of the cellular biomass an exogenous nucleic acid (e.g., a vector comprising a gene expressing constitutively active YAP1) or an exogenous protein (e.g. a wild-type or mutant YAP1 protein), the exogenous nucleic acid or the protein can be heterologous to the metazoan species or it can be species-matched. For example, the culture density and/or thickness of a cellular biomass comprising chicken skeletal muscle cells can be increased by introducing into the cells of the cellular biomass an exogenous nucleic acid that expresses constitutively active form of chicken YAP1 (species-matched) or human YAP1 (heterologous).

It is understood that the methods described throughout this disclosure for inhibiting the HIPPO signaling can be used alone or in combination. For example, methods of inhibiting the HIPPO signaling such as activating YAP1 and/or homologs thereof in the cellular biomass; activating TAZ and/or homologs thereof in the cellular biomass; activating both YAP1 and TAZ and/or homologs thereof in the cellular biomass; inhibiting MOB1, LATS1/2 kinases, WW45, and/or MST1/2 kinases and/or homologs thereof in the cellular biomass; inhibiting non-canonical HIPPO signaling agonists such as aPKC, Tao1, Msn and/or PRP4k and/or homologs thereof in the cellular biomass; contacting the cellular biomass with one or more of serum, lysophosphatidic acid, sphingosine-1-phosphate and/or thrombine, etc. can be used alone or in combinations.

Activating YAP1

In some embodiments, the methods of activating comprise increasing the amount of YAP1 in the cellular biomass by delivering a YAP1 protein directly, e.g. a purified protein, a synthetic protein, or a recombinantly expressed protein, to the cellular biomass (e.g. contacting the cultured cellular biomass with such a protein).

In some embodiments, the methods of activating comprise increasing the cellular expression of YAP1, by expressing a polynucleotide that encodes YAP1. In some embodiments, the polynucleotide is ectopically expressed from a construct that is introduced into the cells of the biomass, for example expressed from a plasmid, or other vector. In some embodiments, the construct is integrated into the cell's host genome, and the expression is driven in that manner (e.g. introduction mediated by CRISPR-based technology). In some embodiments, the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the YAP1 protein that is delivered or expressed comprises a mutation. In some embodiments, the YAP1 comprises a mutation in one or more motifs that allow for phosphorylation of YAP1 by the Large Tumor Suppressor Kinase 1 paralogs, LATS1 kinase and/or LATS2 kinase. In some embodiments the mutated YAP1 comprises a mutation at one or more of S5, S61, S109, S127, S163, S164, and S318 ("S" serine residue number corresponds to the human YAP1 protein). In some embodiments the mutation is an S to A (serine to alanine) mutation. In exemplary embodiments, the mutated YAP1 comprises one or more of S5A, S61A, S109A, S127A, S163A, S164A, and S318A mutations. It is noted that the residue positions recited above refer to the human YAP1 protein. It is understood that the corresponding serine residues in other organisms contributing to the motif for phosphorylation may differ.

In some embodiments, the methods of activating comprise increasing the transcriptional activation of the endogenous YAP1 gene in the cellular biomass. This can be accomplished, for example, by adding a purified, synthetic, or recombinantly produced transcriptional activator of the YAP1 gene to the cellular biomass. In one embodiment, the transcriptional activator of the YAP1 gene added to the culture medium could be a constitutively active form that would drive a continuous expression of the YAP1 gene. In another embodiment, transcriptional activation of the YAP1 gene can be accomplished using nucleic acid sequence-directed transcriptional activators. For example, clustered regularly interspaced short palindromic repeats (CRISPR) and the CRISPR associated protein 9 (Cas9) system can provide effective gene modification (activation and repression) through RNA-guided DNA targeting. The Cas9 protein can be altered to create an endonuclease-defective Cas9 (dCas9). In one embodiment, the dCas9 protein can be fused to a transactivation domain of a transcription factor or a transcriptional activator and the fusion protein can be used to drive transcriptional activation of the endogenous YAP1 gene.

In some embodiments, the methods of activating YAP1 comprise regulating one or more mechanical factors, including modulating substrate elasticity/rigidity, confinement, stretching, and shear stress, in the cellular biomass. Such methods may result in mechanotransduction of YAP1 signaling.

In some embodiments, the activating methods comprise agonizing YAP1, e.g. by contacting the cellular biomass with serum; or by inhibiting a Hippo signaling pathway, by contacting the cellular biomass with one or more of unfractionated animal serum, lysophosphatididic acid, sphingosine-1-phosphate and thrombin. In some embodiments, the activation of YAP1 can be downregulated, as needed by Hippo pathway inhibitors such as epinephrine and glucagon, which repress co-activation by YAP1.

In some embodiments, the culture density of a cellular biomass where YAP1 is activated is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where YAP1 is not activated.

Activating TAZ

In some embodiments, the methods of activating comprise increasing the amount of TAZ in the cellular biomass by delivering a TAZ protein directly, e.g. a purified protein, a synthetic protein, or a recombinantly expressed protein to the cellular biomass (e.g. contacting the cultured cellular biomass with such a protein).

In some embodiments, the methods of activating comprise increasing the cellular expression of TAZ, by expressing a polynucleotide that encodes TAZ. In some embodiments, the polynucleotide is ectopically expressed from a construct that is introduced into the cells of the biomass, for example expressed from a plasmid, or other vector. In some embodiments, the construct is integrated into the cell's host genome, and the expression is expression is driven in that manner (e.g. introduction mediated by CRISPR-based technology). In some embodiments the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the TAZ protein that is delivered or expressed comprises a mutation. In some embodiments, the TAZ comprises a mutation in one or more motifs that allow for phosphorylation of TAZ by the Large Tumor Suppressor Kinase 1 paralogs, LATS1 kinase and/or LATS2 kinase. In some embodiments the mutated TAZ comprises a mutation at S89 ("S" serine residue number corresponds to the human TAZ protein). In some embodiments the mutation is an S to A (serine to alanine) mutation. In an exemplary embodiment, the mutated TAZ comprises a S89A mutation. It is noted that the residue positions recited above refer to the human TAZ protein. It is understood that the corresponding serine residues in other organisms contributing to the motif for phosphorylation may differ.

In some embodiments, the methods of activating comprise increasing the transcriptional activation of the endogenous WWTR1 gene that encodes the TAZ protein in the cellular biomass. This can be accomplished, for example, by adding a purified, synthetic, or recombinantly produced transcriptional activator of the WWTR1 gene to the cellular biomass. In one embodiment, the transcriptional activator of the WWTR1 gene added to the culture medium could be a constitutively active form that would drive a continuous expression of the WWTR1 gene. In another embodiment, transcriptional activation of the WWTR1 gene can be accomplished using nucleic acid sequence-directed transcriptional activators. For example, the endonuclease-defective dCas9 protein can be fused to a transactivation domain of a transcription factor or a transcriptional activator and the fusion protein can be used to drive transcriptional activation of the endogenous WWTR1 gene.

In some embodiments, the methods of activating TAZ comprise regulating one or more mechanical factors, including modulating substrate elasticity/rigidity, confinement, stretching, and shear stress, in the cellular biomass. Such methods may result in mechanotransduction of TAZ signaling.

In some embodiments, the activating methods comprise agonizing TAZ, e.g. by contacting the cellular biomass with serum; or by inhibiting a Hippo signaling pathway, by contacting the cellular biomass with one or more of unfractionated animal serum, lysophosphatididic acid, sphingosine-1-phosphate and thrombin. In some embodiments, the activation of TAZ can be downregulated, as needed by Hippo pathway inhibitors such as epinephrine and glucagon, which repress co-activation by TAZ.

In some embodiments, the culture density and/or thickness of a cellular biomass where TAZ is activated is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where TAZ is not activated.

Activating YAP1 and TAZ

In some embodiments, the methods of activating comprise increasing the amount of both YAP1 and TAZ in the cellular biomass by delivering YAP1 and TAZ proteins directly, e.g. purified proteins, synthetic proteins, or recombinantly expressed proteins, or combinations thereof, to the cellular biomass.

In some embodiments, the methods of activating comprise increasing the cellular expression of YAP1 and TAZ, by expressing polynucleotides that encode YAP1 and TAZ. In some embodiments, the polynucleotides are ectopically expressed from constructs that are introduced into the cells of the biomass, for example expressed from a plasmid, or other vector. In some embodiments, the constructs are integrated into the cell's host genome, and the expression is driven in that manner (e.g. introduction mediated by CRISPR-based technology). In some embodiments the expression of the polynucleotides involve injecting a naked DNA, delivering a DNA complexed with a liposome, using a viral vector (e.g. retrovirus, lentivirus, adenovirus, adeno-associated virus, herpes-simplex virus) to deliver an expression vector, and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of one of YAP1 or TAZ is constitutive, whereas the expression of the other of YAP1 or TAZ is inducible.

In some embodiments, the YAP1 and/or TAZ protein that is delivered or expressed comprises a mutation. In some embodiments, the YAP1 and/or TAZ comprise a mutation in one or more motifs that allow for phosphorylation of YAP1 by the Large Tumor Suppressor Kinase 1 paralogs, LATS1 kinase and/or LATS2 kinase. In some embodiments the mutated YAP1 comprises a mutation at one or more of S5, S61, S109, S127, S163, S164, and S318 ("S" serine residue number corresponds to the human YAP1 protein). In some embodiments the mutation is an S to A (serine to alanine) mutation. In exemplary embodiments, the mutated YAP1 comprises one or more of S5A, S61A, S109A, S127A, S163A, S164A, and S318A mutations. In some embodiments the mutated TAZ comprises a mutation at S89 ("S" serine residue number corresponds to the human TAZ protein). In some embodiments, the mutation is an S to A (serine to alanine) mutation. In an exemplary embodiment, the mutated TAZ comprises a S89A mutation. It is noted that the residue positions recited above refer to the human YAP1 an TAZ proteins. It is understood that the corresponding serine residues in other organisms contributing to the motif for phosphorylation may differ. In some embodiments, the TAZ is wild type, and the YAP1 is mutated. In some embodiments, the YAP1 is wild type and the TAZ is mutated. In some embodiments both the YAP1 and TAZ are mutated.

In some embodiments, the methods of activating comprise increasing the transcriptional activation of the endogenous YAP1 and WWTR1 genes in the cellular biomass. This can be accomplished, for example, by adding purified, synthetic, or recombinantly produced transcriptional activators of the YAP1 and WWTR1 genes to the cellular biomass. In one embodiment, the transcriptional activators of the YAP1 and WWTR1 genes added to the culture medium could be constitutively active and drive a continuous expression of the two genes. In another embodiment, transcriptional activation of the YAP1 and WWTR1 genes can be accomplished using nucleic acid sequence-directed transcriptional activators. For example, the endonuclease-defective dCas9 protein can be fused to a transactivation domain of a transcription factor or a transcriptional activator and the fusion protein can be used to drive transcriptional activation of the endogenous YAP1 and WWTR1 gene.

In some embodiments, the methods of activating YAP1 and TAZ comprise regulating one or more mechanical factors, including modulating substrate elasticity/rigidity, confinement, stretching, and shear stress, in the cellular biomass. Such methods may result in mechanotransduction of YAP1 and TAZ signaling.

In some embodiments, the activating methods comprise agonizing YAP1 and TAZ, e.g. by contacting the cellular biomass with serum; or by inhibiting a Hippo signaling pathway, by contacting the cellular biomass with one or more of unfractionated animal serum, lysophosphatididic acid, sphingosine-1-phosphate and thrombin. In some embodiments, the activation of YAP1 and TAZ can be downregulated, as needed by Hippo pathway inhibitors such as epinephrine and glucagon, which repress co-activation by YAP1 and TAZ.

In some embodiments the culture density and/or thickness of a cellular biomass where YAP1 and TAZ is activated is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where YAP1 and TAZ are not activated.

Inhibiting MOB1 and/or LATS1/2 Kinases

In some embodiments, the methods of inhibiting comprise introducing INDEL (insertion or deletion) mutations into a gene encoding MOB1, gene encoding LATS1 kinase, and/or gene encoding LATS2 kinase into the cells of the cellular biomass. This can be accomplished using any gene based technologies, for example, using CRISPR-Cas (Clustered Regularly Interspersed Short Palindromic Repeats) based technology or TALEN based technology.

In some embodiments, the methods of inhibiting comprise introducing into the cells of the cellular biomass a vector expressing a polynucleotide that encodes a dominant negative mutant of MOB1, LATS1 kinase, and/or LATS2 kinase. In some embodiments, the polynucleotide is ectopically expressed from a construct that is introduced into the cells of the biomass, for example expressed from a plasmid, or other vector. In some embodiments, the construct is integrated into the cell's host genome, and the expression is driven in that manner (e.g. introduction mediated by CRISPR-based technology). In some embodiments, the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the methods of inhibiting comprise delivering dominant negative mutants of MOB1, LATS1 kinase, and/or LATS2 kinase directly, e.g. purified proteins, synthetic proteins, or recombinantly expressed proteins, or combinations thereof, to the cellular biomass.

In some embodiments, the methods of inhibiting comprise transcriptional repression of the endogenous genes encoding MOB1, LATS1 kinase, and/or LATS2 kinase in cells of the cellular biomass. This can be accomplished, for example, by using nucleic acid sequence-directed transcriptional repressors. For example, an endonuclease-defective Cas9, dCas9, can be combined with a guide RNA that targets the promoter region of the genes encoding MOB1, LATS1 kinase, and/or LATS2 kinase and reduces the transcriptional activation and concomitant gene expression.

In some embodiments, the methods of inhibiting comprise inhibiting Hippo signaling, by contacting the cellular biomass with one or more of unfractionated animal serum, lysophosphatididic acid, sphingosine-1-phosphate and thrombin.

In some embodiments the culture density and/or thickness of a cellular biomass where MOB1, LATS1 kinase, and/or LATS2 kinase are inhibited is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where MOB1, LATS1 kinase, and/or LATS2 kinase are not inhibited.

Inhibiting WW45 and/or MST1/2 Kinases

In some embodiments, the methods of inhibiting comprise introducing INDEL (insertion or deletion) mutations into a gene encoding WW45, gene encoding MST1 kinase, and/or gene encoding MST2 kinase into the cells of the cellular biomass. This can be accomplished by using any gene based technologies, for example, using CRISPR-Cas (Clustered Regularly Interspersed Short Palindromic Repeats) based technology or TALEN based technology.

In some embodiments, the methods of inhibiting comprise introducing into the cellular biomass a vector expressing a polynucleotide that encodes a dominant negative mutant of WW45, MST1 kinase, and/or MST2 kinase. In some embodiments, the polynucleotide is ectopically expressed from a construct that is introduced into the cells of the biomass, for example expressed from a plasmid, or other vector. In some embodiments, the construct is integrated into the cell's host genome, and the expression is driven in that manner (e.g. introduction mediated by CRISPR-based technology). In some embodiments, the expression of the polynucleotide involves injecting a naked DNA, delivering a DNA complexed with a liposome, using a viral vector (e.g. retrovirus, lentivirus, adenovirus, adeno-associated virus, herpes-simplex virus) to deliver an expression vector, and the like. In some embodiments, the expression is constitutive. In some embodiments, the expression is conditional, e.g. inducible, e.g. under the control of an inducible promoter, e.g. an inducible Tet construct.

In some embodiments, the methods of inhibiting comprise delivering to the cells of the cellular biomass dominant negative mutants of WW45, MST1 kinase, and/or MST2 kinase directly, e.g. purified proteins, synthetic proteins, or recombinantly expressed proteins, or combinations thereof.

In some embodiments, the methods of inhibiting comprise transcriptional repression of the endogenous genes encoding WW45, MST1 kinase, and/or MST2 kinase in the cells of the biomass. This can be accomplished, for example, by using nucleic acid sequence-directed transcriptional repressors. For example, an endonuclease-defective Cas9, dCas9, can be combined with a guide RNA that targets the promoter region of the genes encoding WW45, MST1 kinase, and/or MST2 kinase and reduces the transcriptional activation and concomitant gene expression.

In some embodiments, the methods of inhibiting comprise inhibiting Hippo signaling, by contacting the cellular biomass with one or more of unfractionated animal serum, lysophosphatididic acid, sphingosine-1-phosphate and thrombin.

In some embodiments, the culture density and/or thickness of a cellular biomass where WW45, MST1 kinase, and/or MST2 kinase are inhibited is about 1.010-fold, 1.025-fold, 1.05 fold, 1.10 fold, 1.15-fold, 1.20 fold, 1.25-fold, 1.30-fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold greater than the culture density of a cellular biomass where WW45, MST1 kinase, and/or MST2 kinase are not inhibited.

Serum Free Conditions

Unfractionated animal serum (UAS), for e.g., fetal bovine serum (FBS), is commonly used as a mitogenic supplement for cell cultures. However, there are certain drawbacks and/or concerns associated with the use of serum such as high cost, batch-to-batch variations, its derivation from an animal source and the like. Accordingly, in one embodiment, provided herein are compositions and methods for increasing cell proliferation, cell viability, and reducing cell death without adding serum to culture medium. In some embodiments, provided are compositions and methods for increasing the culture density and/or thickness of a cellular biomass and for promoting anchorage-independent growth comprising inhibiting the HIPPO signaling pathway without added serum.

The term "serum" as used herein refers to the liquid fraction of whole blood that is collected after the blood is allowed to clot. The clot can be removed by for e.g., centrifugation, and the resulting supernatant is designated serum.

Figure 4:
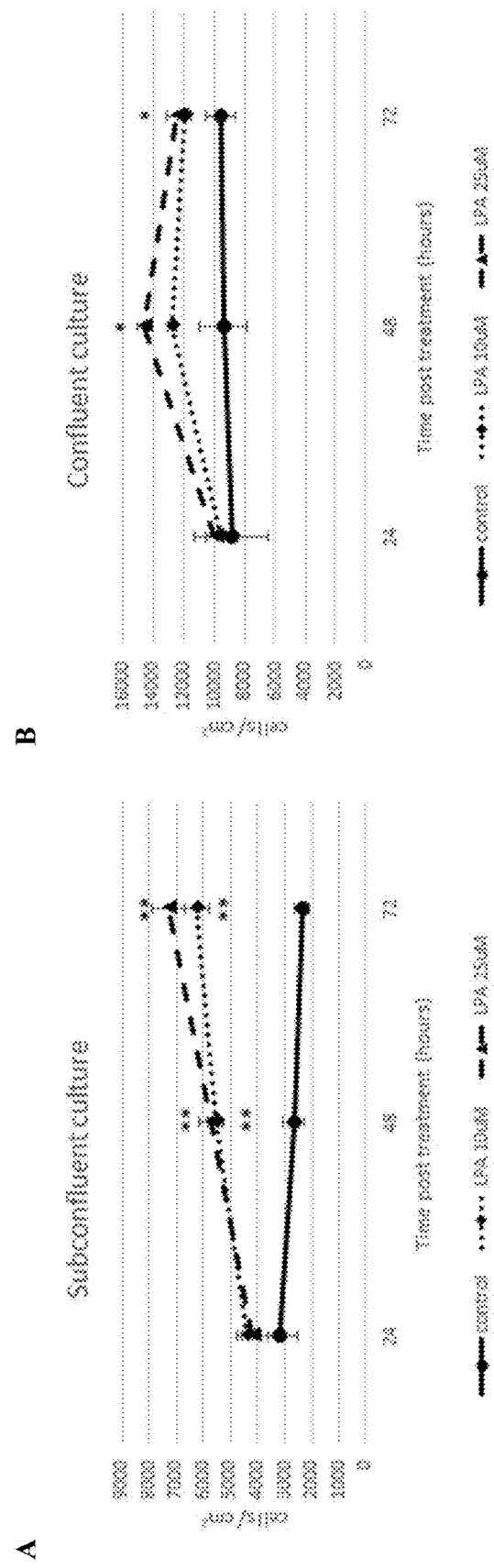
FIG. 4 shows the effect of lysophosphatidic acid on proliferation of primary bovine myoblasts in subconfluent (A) and confluent (B) cultures.

The inventors have found that it is possible to increase cell proliferation, cell viability, reduce cell death, and increase the culture density and/or thickness of a cellular biomass without adding serum to the culture medium (FIG. 4). For example, compositions and methods such as ectopic expression of YAP1 and/or TAZ; addition of YAP1 and/or TAZ proteins to the culture medium; activation of the endogenous YAP1 and/or TAZ genes using, for example, nucleic acid sequence-directed transcriptional activators; addition of HIPPO inhibitors such as lysophosphatidic acid, sphingosine-1-phosphate, and thrombin; and/or ectopic expression of dominant negative mutants of MOB1, LATS1 kinase, LATS2 kinase, WW45, MST1 kinase, and/or MST2 kinase can induce cell proliferation and increase the culture density and/or thickness of a cellular biomass without addition of serum.

Post Expansion Treatment of Cellular Biomass

Methods for increasing the culture density and thickness of cellular biomass and methods for anchorage-independent cell growth described above provide an expanded cellular biomass. Once the desired level of expansion (e.g. a specific range or value of culture density and/or thickness) of the cellular biomass is achieved, inhibition of the HIPPO signaling pathway can be partially or fully terminated and the expanded biomass may be differentiated and harvested.

In some embodiments, inhibition of the HIPPO signaling pathway can be partially or fully terminated by partial or complete removal of the HIPPO inhibitors. For example, in some embodiments, inhibition of the HIPPO signaling pathway can be partially or fully terminated by partial or complete removal of externally added HIPPO inhibitors such as serum, lysophosphatidic acid, YAP1 and TAZ proteins, dominant negative mutants of MOB1, LATS1/2 kinases, WW45, and/or MST1/2 kinases, and the like. In embodiments where the HIPPO signaling is inhibited by expression of YAP1 and/or TAZ proteins through a vector or expression of dominant negative mutants of MOB1, LATS1/2 kinases, WW45, and/or MST1/2 kinases through a vector, inhibition can be partially or fully terminated by activating a silencing switch included in the vector. For example, a silencing switch can be a transcriptional repressor that is included in the vector, which upon activation can repress the transcription of the desired gene.

After partial or complete termination of inhibition of HIPPO signaling, the expanded cellular biomass may be differentiated. In some embodiments, cells of the expanded biomass can be differentiated into a phenotype of interest by contacting the cells with a differentiation agent. For example, if the phenotype of interest for the expanded cellular biomass is skeletal muscle and the cellular biomass comprises cells of a non-muscle lineage (e.g., non-myogenic stem cells or fibroblasts), the expanded cellular biomass can be contacted with a differentiation agent that would induce the skeletal muscle phenotype into the cells of the biomass. Exemplary differentiation agents that may induce skeletal muscle phenotype include myogenic transcription factors such as MYOD1, MYOG, MYF5, MYF6, PAX3, PAX7, paralogs, orthologs, and genetic variants thereof. A PCT publication, WO/2015/066377, discloses exemplary methods for differentiating cells into a skeletal muscle phenotype and is incorporated by reference herein in its entirety. Accordingly, in some embodiments, the expanded cellular biomass may be differentiated into the skeletal muscle phenotype using the methods described in WO/2015/066377.

In some embodiments, cells of the expanded biomass can be differentiated into a phenotype of interest without a differentiation agent. For example, if the phenotype of interest for the expanded biomass is a skeletal muscle and the cellular biomass comprises cells of the skeletal muscle lineage, then these cells may differentiate into the skeletal muscle phenotype on their own without a need for an external differentiation agent. In these embodiments, a partial or complete removal of the antagonism of the HIPPO signaling pathway may be sufficient to induce differentiation of cells of to the skeletal muscle lineage and into the skeletal muscle phenotype. However, in some embodiments, an external differentiation agent such as one or more myogenic transcription factors can be used to differentiate cells of the skeletal muscle lineage into the skeletal muscle phenotype.

The expanded and/or differentiated cellular biomass can be processed as a raw, uncooked food product (cultured meat) or as a cooked food product or as a cooked/uncooked food ingredient. In some embodiments, processing comprises withdrawal of the culture medium that supports the viability, survival, growth or expansion (e.g., increase in the culture density and/or thickness of the biomass, anchorage-independent growth) and differentiation of the cellular biomass. Withdrawal may comprise physical removal of the culture medium or altering the composition of the culture medium, for example, by addition of components that would reduce or prevent further expansion and/or differentiation of the biomass or by depletion of components that support expansion and/or differentiation of the biomass.

In some embodiments, processing comprises exposing the biomass to sub-physiological temperatures that would not support the expansion and/or differentiation of the biomass. Sub-physiological temperatures include a temperature of about 15° C. (about 59° F.) or lower, about 10° C. (about 50° F.) or lower, about 0° C. to about 15° C. (about 32° F. to about 59° F.), about 0° C. to −15° C. (about 32° F. to about 5° F.), about −15° C. to about 15° C. (about 5° F. to about 59° F.), about 0° C. to −213° C. (about 32° F. to about −350° F.), about −30° C. to about −100° C. (about −22° F. to about −148° F.), about −50° C. to about −90° C. (about −58° F. to about −130° F.), or about −170° C. to about −190° C. (about −274° F. to about −310° F.). For example, in one embodiment, the expanded and/or differentiated biomass can be cooled to a temperature of about 2° C. to about 8° C. (about 35° F. to about 46.5° F.). In another embodiment, the expanded and/or differentiated biomass can be frozen, for example, by cooling to a temperature of about 32° F. or lower, e.g. about 32° F. to about 0° F., about 32° F. to about −10° F., about 32° F. to about −20° F., about 32° F. to about −30° F., about 32° F. to about −40° F., about 32° F. to about −50° F., about 32° F. to about −60° F., about 32° F. to about −70° F., about 32° F. to about −80° F., and the like. In some embodiments, the expanded and/or differentiated biomass can be exposed to sub-physiological temperatures as low as about −300° F. to about −350° F., such as the liquid nitrogen temperature of about −321° F.

In some embodiments, processing comprises exposing the biomass to superphysological temperatures that would not support the viability, survival, expansion and/or differentiation of the biomass. In one embodiment, exposing the biomass to superphysiological temperatures comprises fully or partially cooking the biomass, for example, by heating the biomass to a temperature of about 100° F. to about 600° F., about 100° F. to about 550° F., about 100° F. to about 500° F., about 100° F. to about 450° F., about 100° F. to about 400° F., about 100° F. to about 350° F., about 100° F. to about 300° F., about 100° F. to about 250° F., about 100° F. to about 200° F. or about 100° F. to about 150° F.

In some embodiments, provided herein are methods of producing edible cellular biomass (also referred to herein as "cultured meat") or therapeutic cellular biomass comprising, (a) culturing a metazoan cellular biomass in a cultivation infrastructure; (b) inhibiting the HIPPO signaling pathway in the cellular biomass, for example, by activating YAP1 and/or TAZ or by inhibiting MOB1, LATS1 kinase, LATS2 kinase, WW45, MST1 kinase, and/or MST2 kinase in the cellular biomass, to increase the culture density or the thickness of the cellular biomass; (c) optionally differentiating the cellular biomass into a phenotype of interest (e.g. skeletal muscle); (d) harvesting the cellular biomass to provide an edible or therapeutic cellular biomass.

In some embodiments, methods of producing edible cellular biomass or therapeutic cellular biomass comprise: (a) culturing a metazoan cellular biomass in a cultivation infrastructure; (b) inhibiting the HIPPO signaling pathway in the cellular biomass to provide a culture density of about $10^5$ cell/mL to about $10^{10}$ cells/mL or about 1 g/L to about 1000 g/L (or other values and ranges of the culture density described throughout this disclosure) in the cultivation infrastructure; (c) optionally differentiating the cellular biomass into a phenotype of interest (e.g. skeletal muscle); (d) harvesting and processing the cellular biomass to provide an edible or therapeutic cellular biomass.

In some embodiments, methods of producing edible cellular biomass or therapeutic cellular biomass comprise: (a) culturing a metazoan cellular biomass in a cultivation infrastructure; (b) inhibiting the HIPPO signaling pathway in the cellular biomass to provide a thickness of the cellular biomass of about 10 μm to about 2 mm (or other values and ranges of the thickness of the cellular biomass described throughout this disclosure) in the cultivation infrastructure; (c) optionally differentiating the cellular biomass into a phenotype of interest (e.g. skeletal muscle); (d) harvesting and processing the cellular biomass to provide an edible or therapeutic cellular biomass; (e) improve cell proliferation without added serum; (f) improve anchorage-independent cell proliferation.

Kits and Articles of Manufacture

The present application also provides kits for increasing the culture density in a cultivation infrastructure, for increasing the thickness of a cellular biomass in a cultivation infrastructure, and/or for promoting/increasing anchorage-independent growth of a cellular biomass in a cultivation infrastructure. For example, the kits may comprise the cells of interest, a cultivation infrastructure, and the HIPPO signaling pathway inhibitors such as YAP1 or TAZ vectors or protein; compositions for enhancing the activation of endogenous YAP1 and/or TAZ gene; compositions for the inhibition of MOB1, LATS1 kinase, LATS2 kinase, WW45, MST1 kinase, and/or MST2 kinase; vectors expressing dominant negative mutants of MOB1, LATS1 kinase, LATS2 kinase, WW45, MST1 kinase and/or MST2 kinase; and the like.

The present application also provides articles of manufacture comprising any one of the compositions or kits described herein.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Example 1: Increasing the Thickness of Biomass Cultivated on a Substrate

One protocol for increasing the thickness of a biomass cultivated on a substrate comprises 7 steps: (1) transfect an anchorage-dependent, bovine myoblasts with a construct expressing YAP1 or TAZ under the control of a doxycycline-inducible eukaryotic promoter and containing an antibiotic-resistance gene; (2) select and enrich the transfected cells with a dosage of antibiotic lethal to the non-transfected cells; (3) passage the cells to a cultivation substrate supporting cell adhesion, and cultivating the cells to super-confluence in a proliferation medium, and for four additional days after the cells become super confluent, with daily culture media changes; in the presence of doxycycline; (4) aspirate the liquid proliferation medium from the cell biomass; (5) add liquid differentiation medium to the cell biomass, omitting doxycycline and differentiate the biomass into skeletal muscle over the course of four days, with daily media changes; (6) mechanically dissociate the cells from the substrate, and measure the weight of the bovine skeletal muscle biomass; and (7) prepare bovine skeletal muscle biomass as a food product by rinsing in an isotonic buffer and frying in an oiled pan until evenly brown. The expected yield limit of the cells population expressing the ectopic YAP1 or TAZ is expected to be at least 4-fold greater than the wild-type cells, due to the ability of the cells overexpressing the YAP1 or TAZ to bypass contact inhibition of cellular proliferation.

Example 2: Adapting Anchorage-Dependent Cells for Cultivation in Suspension

Anchorage-dependent cells can be adapted for cultivation in suspension, and can include at least the following steps: (1) transfect an anchorage-dependent, chicken myoblasts with a construct expressing YAP1 or TAZ under the control of a doxycycline-inducible eukaryotic promoter and containing an antibiotic-resistance gene; (2) select and enrich the transfected cells with a dosage of antibiotic lethal to the non-transfected cells; (3) passage the cells in a single-cell suspension to a shaker flask in proliferation medium supplemented with doxycycline, and shake flask in a slow, orbital motion sufficient to prevent the cells from sedimentation within the flask and keep cells in suspension; (4) clonally isolate proliferating cells from the suspension culture and passage to another suspension culture, as described in step no. 3 for scaling the cultivation of biomass, or into an anchorage-dependent culture, as described in Example 1, for cultivation of skeletal muscle biomass to be formulated as food.

Example 3: Isolation of Primary Cells from a Metazoan Source

Protocol #1: Prior to isolation of cells, a 150 cm$^2$ flask (T-150 flask) was prepared for cell attachment by dispersal of a 10 mL of a peptide solution (e.g. 0.1% gelatin) into the flask and incubating the flask for at least 1 hour at 37° C. The aqueous peptide solution was aspirated from the T-150 flask and the flask was rinsed with phosphate-buffered saline. 25 mL of growth medium was formulated to support proliferation of the cell type isolated. For example, a growth medium comprising Dulbecco's Modified Eagle Medium+10% bovine serum, was added to the flask and the flask was incubated and equilibrated under standard culture conditions, such as about 37° C. in 5% atmospheric $CO_2$.

Under aseptic conditions, a bovine skeletal muscle tissue was excised with dissection instruments. Viable metazoan tissues were harvested and minced into approximately 2 mm×2 mm sections. 150 mg tissue sections were weighed and then transferred to a sterile 50 mL centrifuge tube containing 8 mL of enzymatic cell dissociation solution (e.g. 0.17% trypsin and 0.085% collagenase in Hank's Balanced Salt Solution, pH 7.4). The centrifuge tube was closed tightly and incubated on ice. Following overnight incubation on ice, the tube was incubated at 37° C. for 15 minutes. The enzymatic tissue digest was triturated with a sterile 5 mL serological pipet for 1 minute. Cell suspension was passed through a sterile 70 µm strainer into a sterile 50 mL centrifuge tube. 20 mL of cold Dulbecco's Modified Eagle Medium was added to the strainer. The strainer was discarded, and the tube capped. The tube was centrifuged at 300×g for 5 minutes. The supernatant was aspirated, and the cell pellet was resuspended using the growth medium equilibrated in the 150 cm$^2$ flask. The cell suspension was transferred to the 150 cm$^2$ flask and the flask was returned to incubator for incubation under standard culture conditions.

The cells were checked daily for growth and contamination. The culture medium was changed every two to three days. After the cell cultures reached a confluence of 70% to 90%, the cells were dissociated and either cryopreserved or passaged using standard cell culture technique.

Protocol #2: Prior to isolation of cells, a T-150 flask was prepared as described in Protocol #1. In this protocol, a commercially available tissue dissociation instrument (e.g., from Miltenyi Biotech, Inc.) was used to dissociate tissues in conjunction with a commercially available skeletal muscle dissociation kit (e.g. from Miltenyi Biotech, Inc.). Skeletal muscle dissociation kit enzymes were mixed with Dulbecco's Modified Eagle Medium according to the manufacturer's instructions. ~5 mL of the enzymatic mixture was transferred into a gentleMACS C tube (Miltenyi Biotech, Inc.) according to the manufacturer's instructions.

Under aseptic conditions, a metazoan tissue of interest (e.g. a skeletal muscle tissue) was excised with dissection instruments. Viable tissues were minced into 2-4 mm pieces. Approximately one gram of the minced tissue was added to the gentleMACS C tube containing the enzymatic mixture. The gentleMACS C tube was closed tightly, loaded onto the tissue dissociation instrument, and an appropriate program cycle on the instrument was run according to the manufacturer's instructions. Once the program cycle ended, the gentleMACS C tube was unloaded and centrifuged at 300×g for 5 minutes to sediment isolated cells to the tube bottom.

The cell isolate was resuspended in Dulbecco's Modified Eagle Medium and the cell suspension was applied to a 70 µM cell strainer placed on a 50 mL centrifuge tube. The cell strainer was washed with 20 mL of cold Dulbecco's Modified Eagle Medium and the cell strainer was discarded. The cell suspension was centrifuged at 300×g for 20 minutes, and the supernatant was aspirated completely. The cell suspension was resuspended using equilibrated cell growth medium from the T-150 flask and the flask was returned to the incubator for incubation under physiological conditions.

The isolated cells were checked daily for growth and contamination. The culture medium was changed every two to three days. After the cultures reached a confluence of 70% to 90%, the cells were dissociated and either cryopreserved or passaged using standard cell culture technique.

Example 4: Inhibition of the HIPPO Signaling Pathway Using Lysophosphatidic Acid (LPA) Increases the Culture Density/Thickness of Cellular Biomass Bovine myoblasts were isolated from a bovine skeletal muscle tissue using the protocol described above. Isolated myoblasts were plated at a culture density of 2000 (subconfluent) or 10,000 (confluent) cells per well in a 96 well plate in triplicate wells. The cells were allowed to adhere for 24 hours, at which time LPA was added at a concentration of 0, 10 or 25 µM in the medium. Cells were subsequently harvested and counted by bright field cell imaging (Cytation 5 live cell imaging, analyzed with Lionheart software). FIG. 4A shows that the cells in the subconfluent culture increased by 309% and the cells in the confluent culture (FIG. 4B) increased by 130%. Data shown are mean +/−SD. Significance was determined by the Student's T test.

Figure 5:
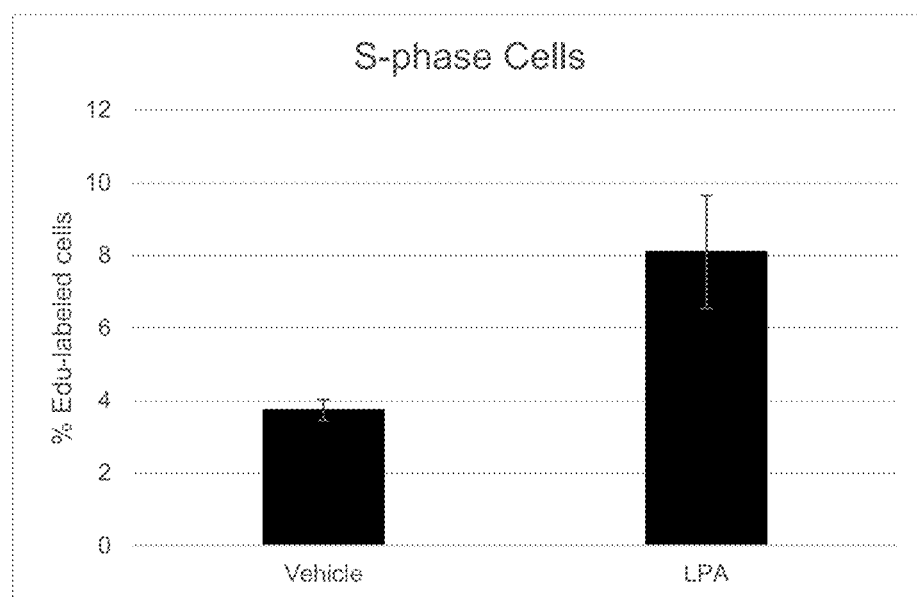
FIG. 5 shows that the treatment of primary bovine myoblasts with lysophosphatidic acid induces cell proliferation.
Figure 6:
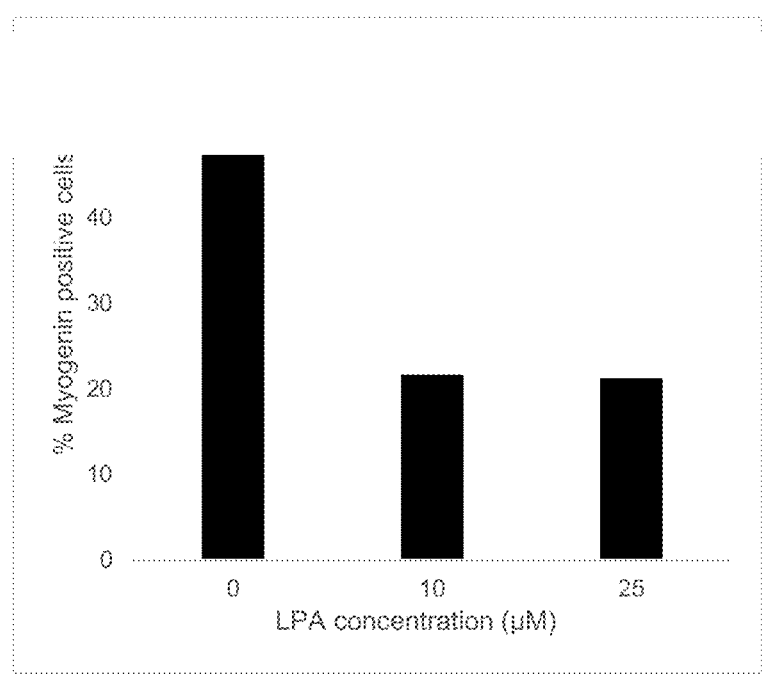
FIG. 6 shows that the treatment of primary bovine myoblasts with lysophosphatidic acid decreases differentiation of myoblasts to mature muscle cells.

In another experiment, bovine myoblasts were plated at a culture density of 10,000 cells per well in a 96 well plate in triplicate wells. The cells were allowed to adhere for 24 hours, when 10 µM LPA was added in the medium. Cells were subsequently harvested. After 24 hours, the proliferation rate was measured by EdU incorporation using a commercially available nucleoside pulse labeling kit such as the Click-iT-EdU kit (Thermaisher). Briefly, cells were treated with 3 µM EdU, incubated at room temperature for 6 hours and detected according to the manufacturer's instructions. Cells were labeled with Alexa Fluor® 647 azide and analyzed using Fluorescence-Activated Cell Sorting (FACS) using 633 nm excitation and a 660/20 nm emission filter. FIG. 5 shows that the LPA treated cells had increased percentage (216% increase) of cells in the S-phase, which is indicative of increased proliferation, compared to vehicle-treated (culture medium alone without LPA) cells.

Example 5: Treatment of Cells with LPA Decreases Differentiation of the Cells

Isolated bovine myoblasts were plated in a culture medium without adding serum at a culture density of 10,000 cells per well in a 96 well plate in triplicate wells. The cells were allowed to adhere for 24 hours, when LPA was added at a concentration of 0, 10 or 25 µM in serum-free medium. LPA was added daily until harvesting. Myogenin was used as a marker of differentiation to mature muscle cells. To determine the degree of differentiation to mature muscle cells, cultures were fixed in 4% paraformaldehyde for 10 min and then washed with PBS. Cells were incubated with PBS/0.2% BSA/0.1% Triton-X100 for 20 min followed by incubation with an anti-myogenin antibody (Abcam, mouse, 1/150) for 1 h at room temperature. After 3 washes with PBS/0.2% BSA, cells were incubated with secondary antibodies (goat anti-rabbit Alexa488, 1/800; goat anti-mouse Alexa555, 1/800, Invitrogen) for 30 min at room temperature. Nucleus was stained with DAPI. LPA treated cells show reduced expression of myogenin.

Example 6: Generation of Plasmids Expressing YAP1-RFP, TAZ-GFP and Control Vectors Reporter vectors containing GFP and RFP reporter sequences, namely, pDd669-AD+RFP and pD663-ARc+GFP were obtained from ATUM Bio and used as control vectors. Human YAP1 polynucleotide sequence containing a constitutively active mutation S127A (SEQ ID NO: 1) was assembled into pD663-ARc vector, and human TAZ polynucleotide sequence containing a constitutively active mutation S89A (SEQ ID NO: 3) was assembled into pD669-AD for enforced expression of these genes. Vectors were introduced into cultured cells using Lipofectamine reagent (ThermoFisher) according to manufacturer's instructions, and selected using G418 (Sigma, pDd669 vectors) or puromycin (Sigma, pD663 vectors) for 14 days.

Figure 7:
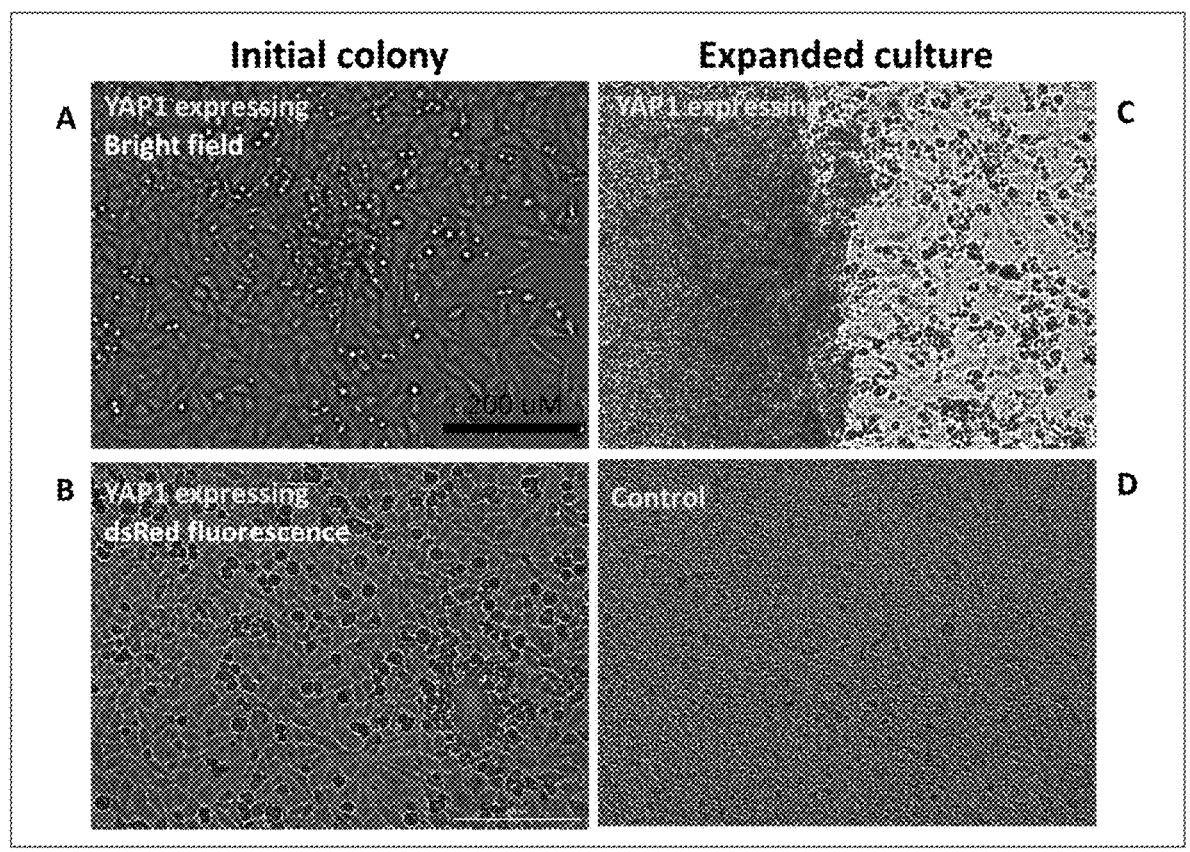
FIG. 7 shows images of chicken fibroblasts (DF1) transduced with a plasmid expressing constitutively active YAP1 and dsRed and untransfected fibroblasts (control). Panels A and B show the initial colonies (prior to expansion) of the cells transduced with the plasmid (A—under bright field setting, B—under fluorescent setting). Panels C and D show images of expanded colonies of fibroblasts transduced with the YAP1-dsRed plasmid (C) and untransfected fibroblasts (D).

Example 7: Expression of Constitutively Active YAP1 Increases the Culture Density and the Thickness of the Cellular Biomass Cells originating from a chicken fibroblast cell line, (DF1), were transduced with a plasmid expressing hYAP1, dsRed, and a neomycin resistance gene. Cells were selected for 8 days in the presence of G418, when dsRed positive colonies appeared in culture. Selected cells were plated in a 6 well plate and cultured for 3 weeks. As shown in FIG. 7, YAP1-expressing cells proliferated, showed loss of contact inhibition, and formed stratified multiple cell layers thereby increasing the culture density and the thickness of the initial cellular biomass when allowed to proliferate for 2 weeks after formation of a confluent monolayer. For example, in FIG. 7C, a large colony of stratified cells, as seen on the left side of image, boarders a monolayer of cells, as seen on the right side of the image. This characteristic colony-formation and cell stratification was observed only in DF1 cultures expressing ectopic YAP1. The initial thickness of the YAP1 expressing cultures was less than 20 μm and the thickness after expansion was 80 μm. In contrast, control cultures (untransfected cells) remained in a uniform monolayer. These results indicate that overexpression of YAP1 leads to loss of contact inhibition and increases the culture density and the thickness of cellular biomass.

Figure 17:
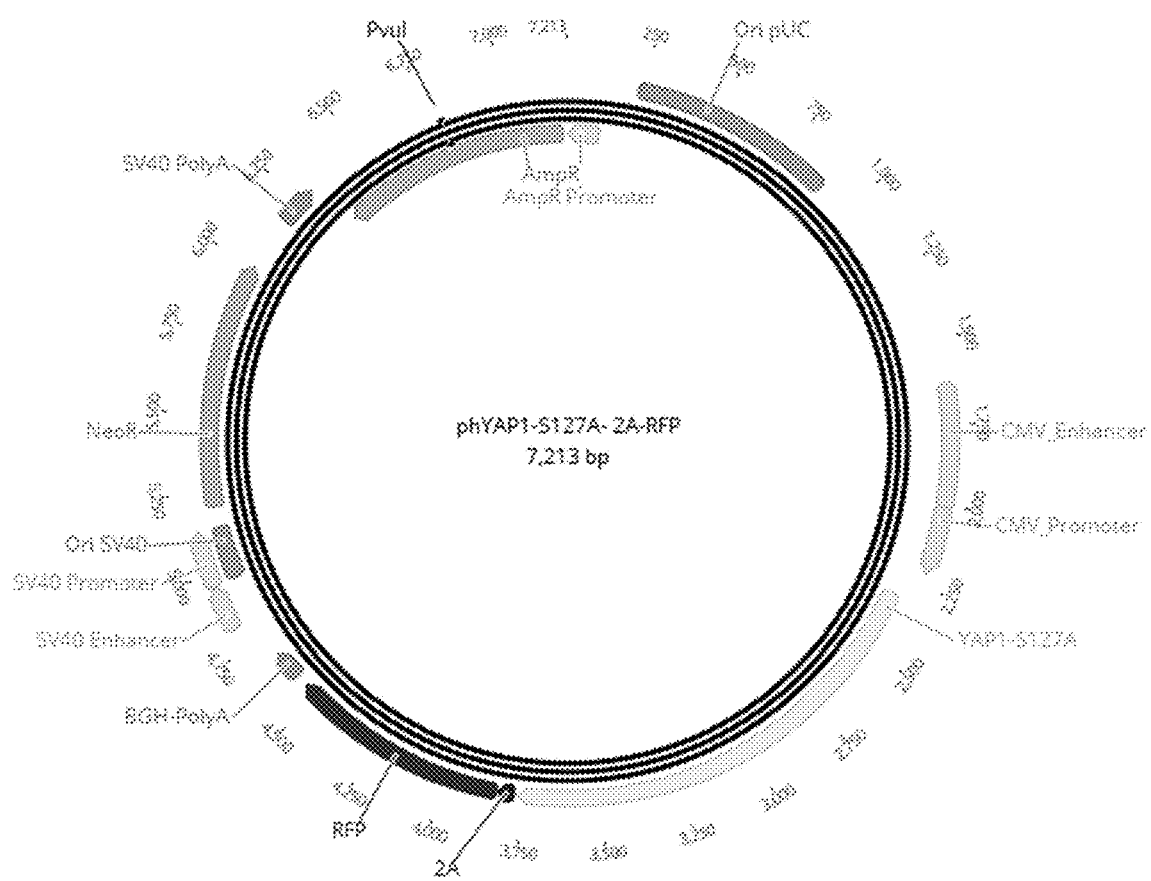
FIG. 17 shows a map of an exemplary plasmid containing a hYAP1 and RFP construct.
Figure 18:
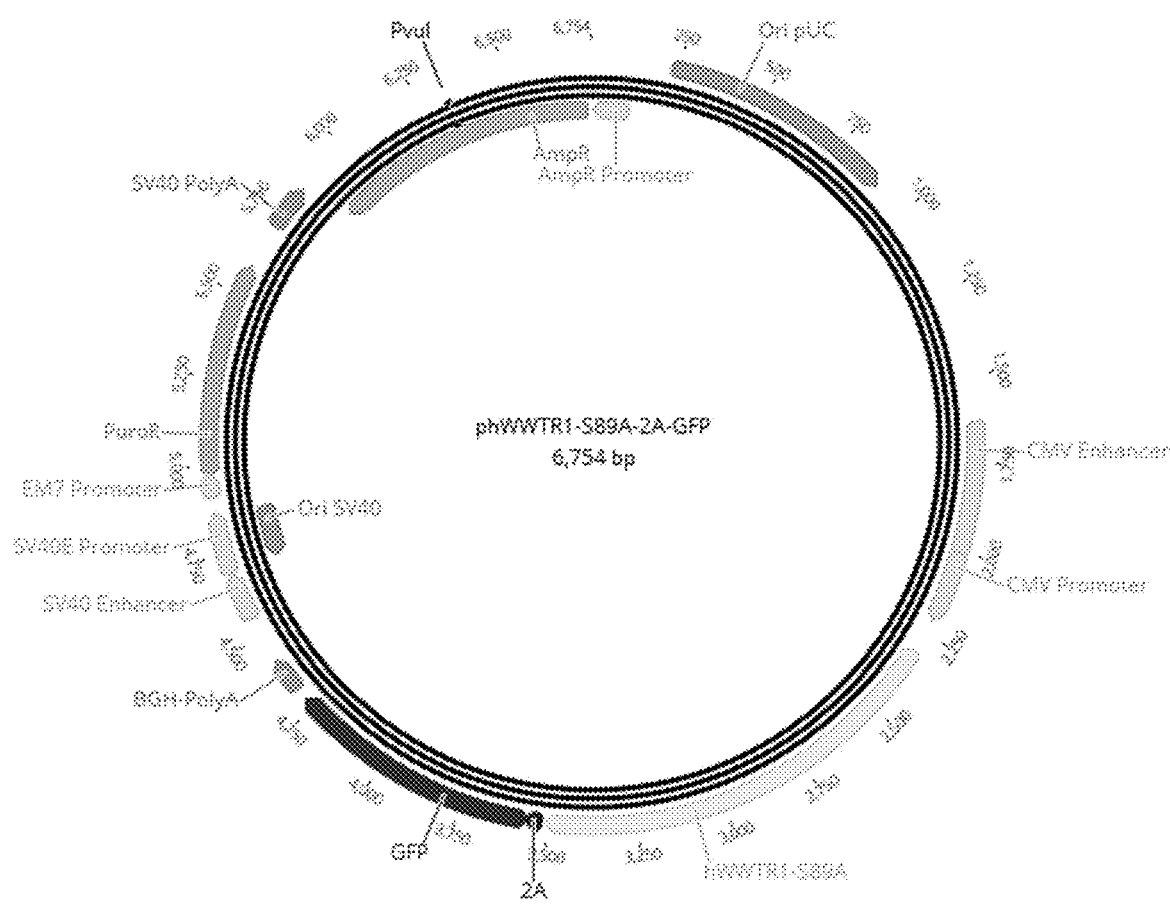
FIG. 18 shows a map of an exemplary plasmid containing a hWWTR1 and GFP construct.

In another experiment, the increase in the thickness of the cellular biomass was measured as follows. Isolated primary fibroblasts were transfected with a plasmid expressing hYAP1 and RFP. FIGS. 17 and 18 show maps of exemplary plasmids expressing (a) hYAP1 and RFP (FIG. 17) and (b) hWWTR1 (a gene encoding TAZ) and GFP (FIG. 18).

Figure 8:
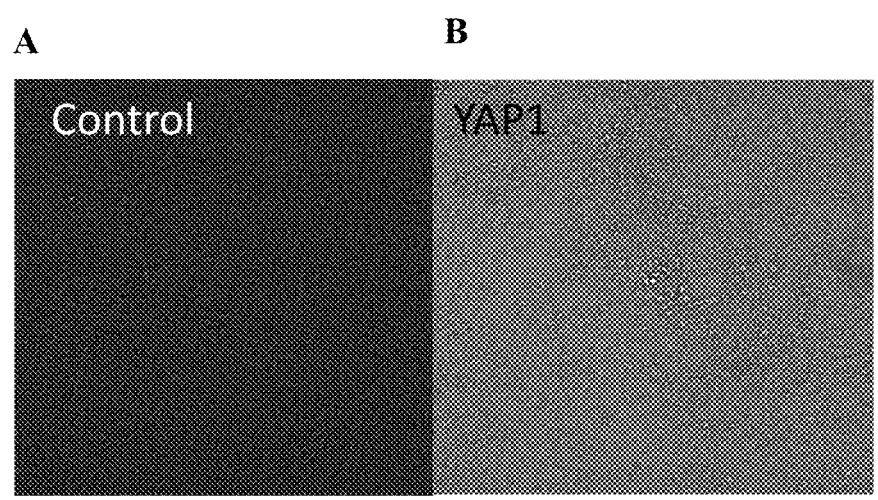
FIG. 8 shows the wild-type cell culture (A) and the culture of hYAP1 (human YAP1) expressing cells (B) on day 9.

Untransfected cells and hYAP1-RFP expressing cells were seeded at a density of $2.5 \times 10^5$ per well in a 6-well plate and allowed to grow for 9 days post-confluence. Colonies of varying thickness were observed in the well containing hYAP1-RFP expressing cells whereas the well containing untransfected, wild-type cells showed a monolayer growth. Images were captured using the ImageXpress Micro XLS Widefield High-Content analysis system. Z-stacks were obtained from the base of the cells to the top of the cells to include all the cells in the region of interest (ROI). The number of 2D images per z-stacks relies on the thickness of the cells being imaged and the step size. Previous studies have measured 3D cell thickness and volumes from single section information, from partial stacks or even from cell diameter. The hYAP1-RFP expressing cells formed colonies of cells that were thicker than a regular monolayer. This is indicative of a decrease in contact inhibition due to the overexpression of YAP1. FIG. 8 (panel A) shows the wild-type cell culture and panel B shows the culture of hYAP1 expressing cells. The thickness of wild-type and YAP1 expressing cellular biomass on day 9 of the culture was as follows:

TABLE 1

| Cell type | Thickness |
| --- | --- |
| Wild type | 6 μM |
| YAP1 expressing | 17 μM |

Example 8: Expression of Constitutively Active YAP1 Increases Cell Mass

Figure 9:
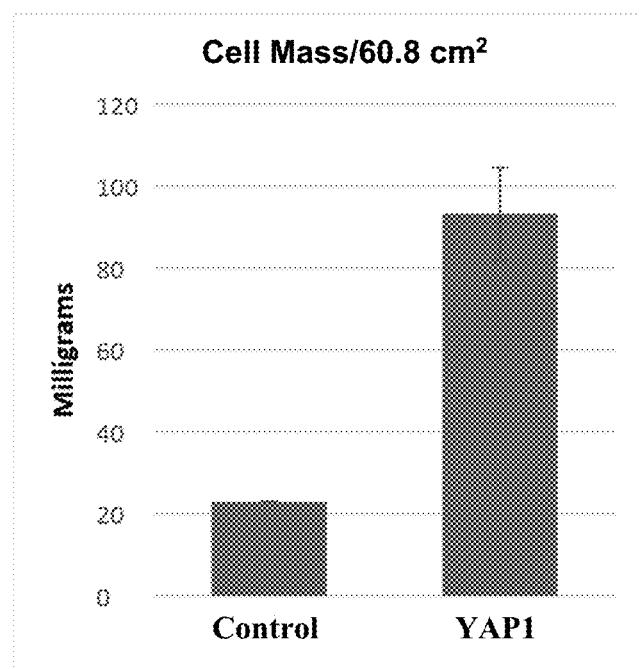
FIG. 9 shows the effect of constitutive expression of YAP1 on cell mass/60.8 $cm^2$ for wild-type cells vs. cells transduced hYAP1-RFP plasmid.

DF1 fibroblasts expressing hYAP1-RFP or wild type cells were plated at $5.5 \times 10^3$ cells per cm² in 10 cm tissue culture plates. After 11 days, the cultures were harvested using a cell scraper and a PBS rinse. The suspension was transferred into a 15 mL tube and centrifuged at 500 g for 5 minutes. The supernatant was aspirated and the wet cell mass was measured on an electronic scale. As shown in FIG. 9, wet cell mass/60.8 cm² of YAP1-expressing cells was significantly more (about 4.5 fold) than that of wild-type cells.

Example 9: YAP1 Expression in Cells Transfected with YAP1-dsRed Plasmid

Figure 10:
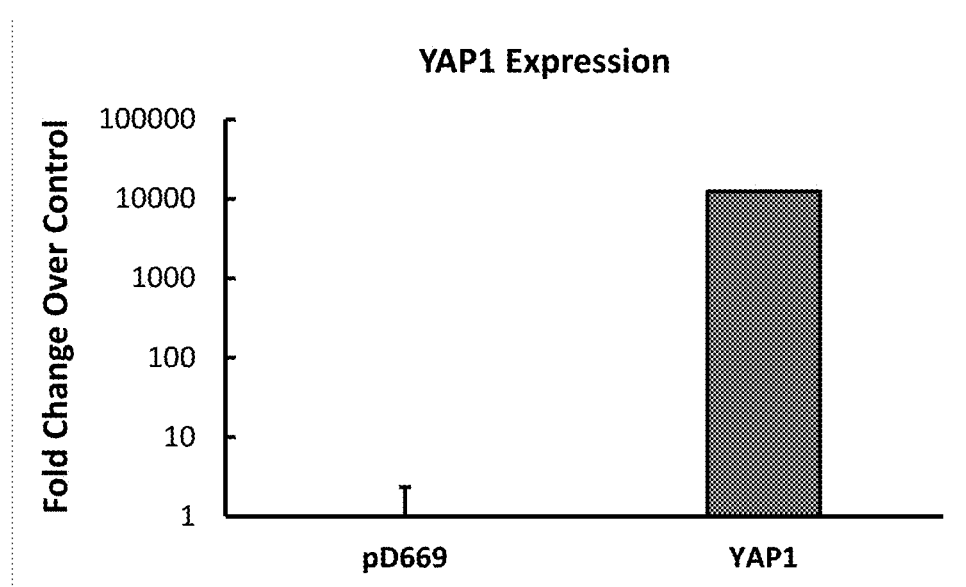
FIG. 10 shows the level of YAP1 mRNA in wild-type cells and cells transduced with hYAP1-dsRed plasmid and selected for dsRed.

Wild type and YAP1 transfected DF1 chicken fibroblast cells were cultured for 2 days and harvested using trypsin digestion. RNA was harvested using a commercially available RNA isolation kit Quick-RNA MiniPrep from Zymo Research). RNA was quantified using the NanoPhotometer (Implen). 250 ng of total RNA was used for a cDNA reaction using a commercially available reverse transcriptase kit (BioRad). 12.5 ng of cDNA was used for a qPCR reaction using the SsoAdvanced Universal Probes Supermix (Bio-Rad). Human YAP1 mRNA expression and chicken actin mRNA expression was quantified using a commercially available Taqman assay kits (ThermoFisher Scientific). The sequences for primers and probes used in this experiment are listed as SEQ ID NOs: 21-23. Relative gene expression analysis was carried out using the delta-delta Ct method. Cells transfected with hYAP1-dsRed plasmid show a high expression of hYAP1 mRNA (FIG. 10).

Figure 11:
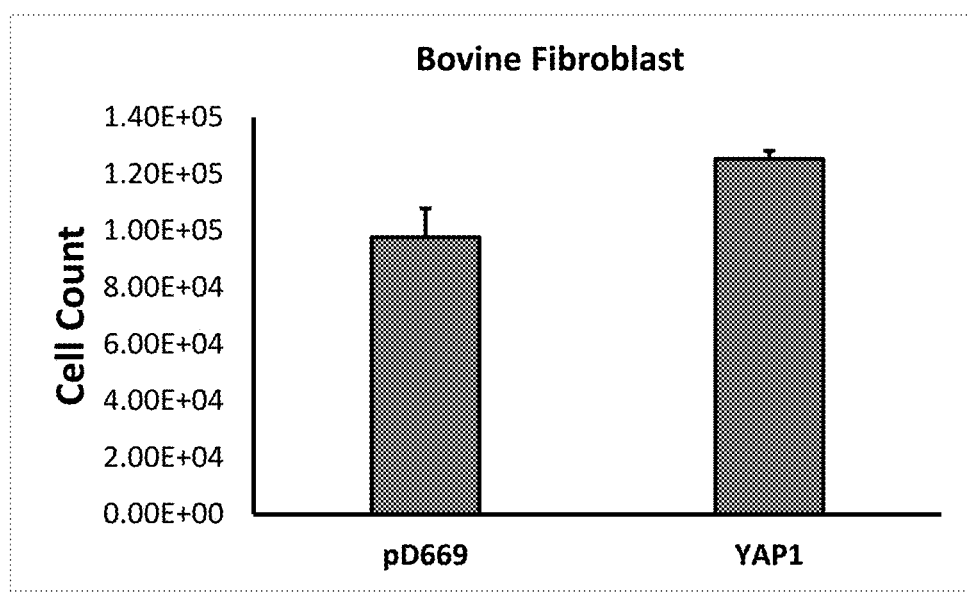
FIG. 11 shows that the expression of constitutively active YAP1 increases proliferation of primary bovine fibroblasts (A) and chicken fibroblasts (B).
Figure 11:
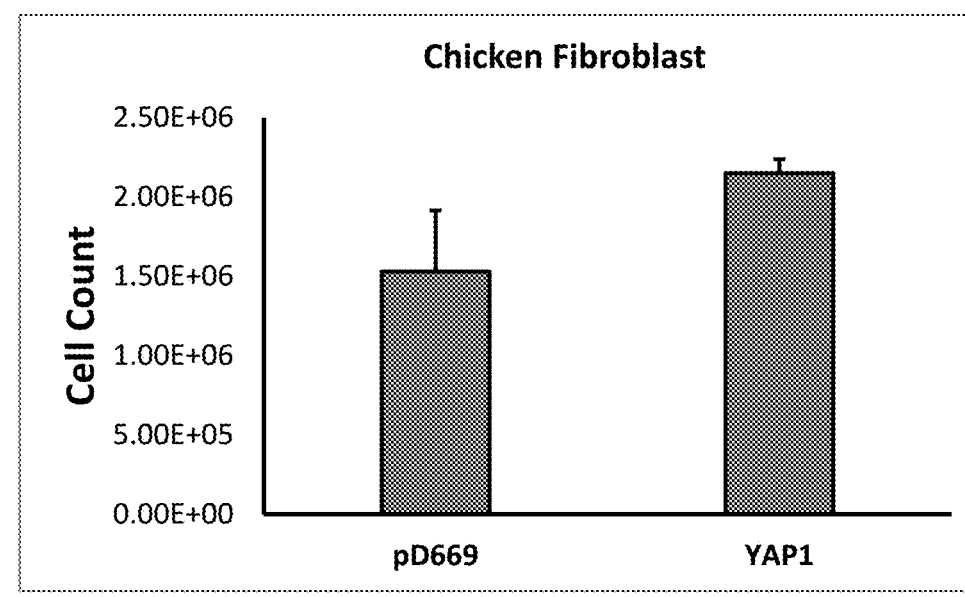

Example 10: Expression of Constitutively Active YAP1 Increases Cell Proliferation Primary bovine fibroblasts and chicken DF1 fibroblasts at a culture density of $1.5 \times 10^5$ per sample were transduced with a plasmid expressing hYAP1 and dsRed, with neomycin resistance gene. Cells were harvested after 72 hours and counted by the Trypan blue method on a hemacytometer. Cells transduced with YAP1 showed an increased growth rate (FIG. 11). Error bar indicates standard deviation. **=P=0.01 *=P<0.05

Example 11: Expression of YAP1 Increases the Rate of Cell Proliferation

Figure 12:
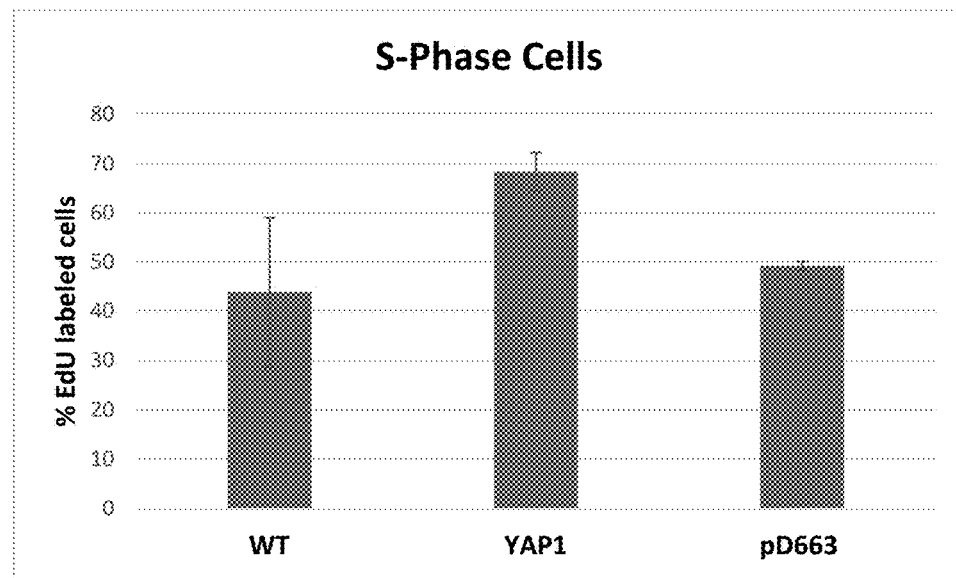
FIG. 12 shows that the expression of constitutively active YAP1 increases rate of cell proliferation. Panel A shows the rate of proliferation of wild-type DF1 cells (chicken fibroblast cell line); DF1 cells transfected with a hYAP1-RFP plasmid, and DF1 cells transfected with a control plasmid (pD663). Panel B shows a clear separation of proliferating cells that have incorporated EdU and non-proliferating cells that did not incorporate EdU.
Figure 12:
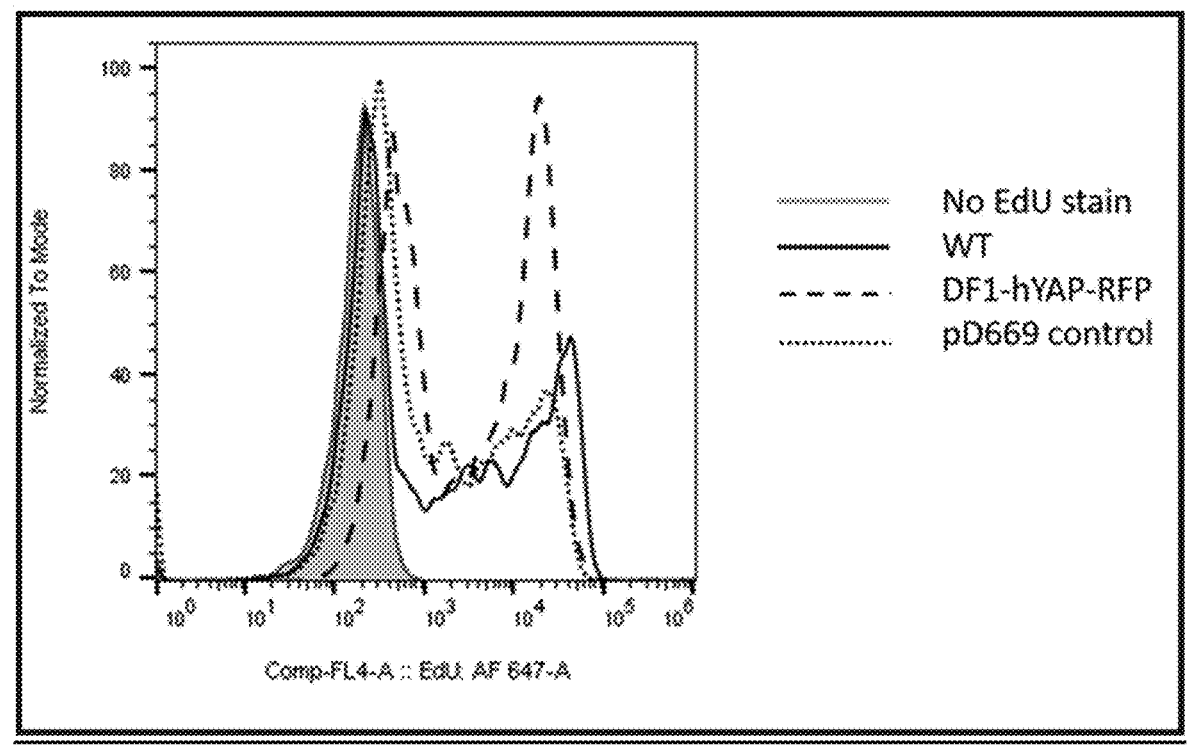

DF1 cells (chicken fibroblast cell line) were transduced with a hYAP1-RFP expressing plasmid or a control vector with dsRed (pD663). hYAP1-RFP expressing cells were selected by flow cytometric sorting based on the expression of dsRed from the hYAP1-RFP vector. Similarly, cells transduced with a control vector expressing dsRed, but no hYAP1 (pD663) were selected by flow cytometric sorting based on the expression of dsRed. The selected transduced cells were allowed to adhere for 24 hours, harvested, and seeded at a density of $1\times10^5$ cells per well in a 12 well plate. After 48 hours, the cells were treated with 3 μM EdU, incubated at room temperature for 6 hours and detected using the manufacturer's instructions. Cells were labeled with Alexa Fluor® 647 azide and analyzed by a FACS using 633 nm excitation and a 660/20 nm emission filter. YAP1-expressing cells have the highest number of cells in the S-phase, which is indicative of increased proliferation (FIG. 12A). The histogram in FIG. 12B shows a separation between cells which have incorporated EdU, indicative of proliferating cells vs. cells which did not incorporate EdU, indicative of non-proliferating cells.

Figure 13:
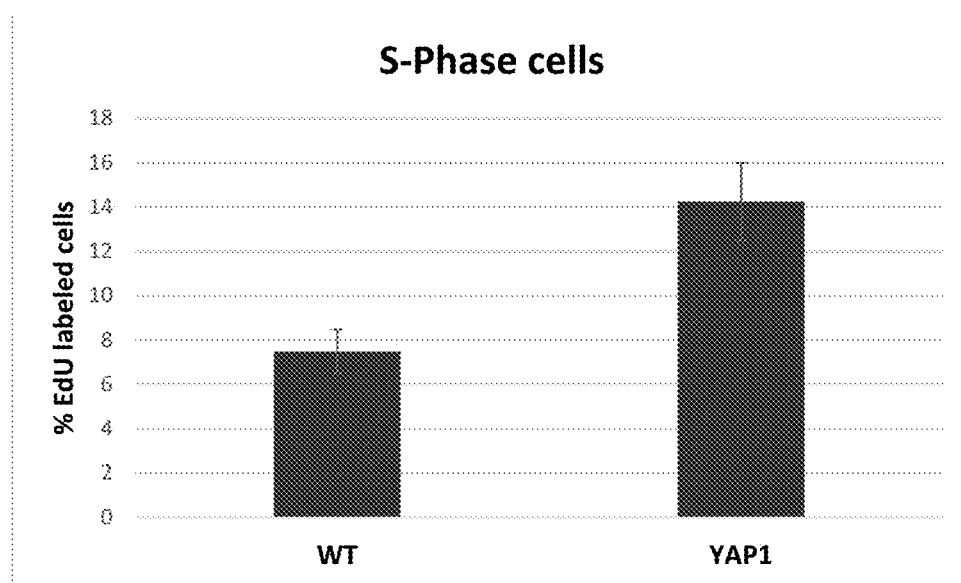
FIG. 13 shows that the ectopic expression of YAP1 in cells cultured in suspension induces cell proliferation.

Example 12: Expression of YAP1 Increases the Rate of Cell Proliferation in Suspension Cultures DF1 cells were transduced using the hYAP1-RFP plasmid and seeded at a density of $1\times10^4$ cells per well in a low binding plate (24-well). After 6 days, the cells were treated with 3 μM EdU, incubated at room temperature for 6 hours and detected according to the manufacturer's instructions. The cells were labeled with Alexa Fluor® 647 azide and analyzed using a FACS using 633 nm excitation and a 660/20 nm emission filter. Despite their native adherent characteristics, YAP1 expressing cells have a significantly higher number of cells in the S-phase (FIG. 13), which is indicative of increased proliferation and transition from anchorage-dependent to anchorage-independent growth in culture.

---

The invention claimed is:

1. A method of making edible metazoan cellular biomass by increasing the culture density of a metazoan cellular biomass, the method comprising:
   a) culturing a metazoan cellular biomass in a cultivation infrastructure in a culture medium;
   b) inhibiting the HIPPO signaling pathway in the cellular biomass;
   c) expanding the cellular biomass: and
   d) harvesting the cellular biomass to provide an edible cellular biomass, wherein the metazoan cellular biomass comprises myogenic cells or fibroblastic cells from a livestock, poultry, or game species, and wherein the method is carried out without adding fetal bovine serum to the culture medium, and wherein the HIPPO signaling pathway is carried out in the cultivation infrastructure to provide a culture density of about $10^5$ cell /mL to about $10^{10}$ cells/mL and to provide a culture density of about 1 g/L to about 1000 g/L.

2. The method of claim 1, wherein inhibiting the HIPPO signaling pathway comprises activating one or more of Yes-Associated Protein 1 (YAP1), Transcriptional co-Activator with PDZ-binding motif (TAZ), and homologs thereof.

3. The method of claim 1, wherein inhibiting the HIPPO signaling pathway comprises inhibiting one or more of Mps One Binder kinase activator 1 (MOB1), Large Tumor Suppressor 1 (LATS1) kinase, Large Tumor Suppressor 2 (LATS2) kinase, WW45, Macrophage Stimulating 1 (MST1) kinase, Macrophage Stimulating 2 (MST2) kinase, and homologs thereof.

4. The method of claim 2, wherein the activating comprises increasing cellular expression of one or more of YAP1, TAZ, and homologs thereof.

5. The method of claim 2, wherein the YAP1 comprises one or more mutations in the region targeted by LATS1 and/or LATS2 kinase activity.

6. The method of claim 5, wherein the YAP1 comprises one or more mutations at residues corresponding to S5, S61, S109, S127, S163, S164, and S318 in the human YAP1 protein.

7. The method of claim 6, wherein the YAP1 comprises one or more of S5A, S61A, S109A, S127A, S163A, S164A, and S318A mutations.

8. The method of claim 2, wherein the TAZ comprises a mutation in the region targeted by LATS1 and/or LATS2 kinase activity.

9. The method of claim 8, wherein the TAZ comprises a mutation at a residue corresponding to S89 in the human TAZ protein.

10. The method of claim 9, wherein the TAZ comprises a S89A mutation.

11. The method of claim 1, wherein inhibiting the HIPPO signaling pathway comprises contacting the cellular biomass with one or more of serum, lysophosphatidic acid, sphingosine-1-phosphate, and thrombin.

12. The method of claim 1, wherein the cellular biomass is adherent to a substrate.

13. The method of claim 12, wherein the substrate is impermeable.

14. The method of claim 12, wherein the substrate is permeable.

15. The method of claim 1, wherein the cellular biomass is a self-adherent aggregate.

16. The method of claim 1, wherein inhibiting the HIPPO signaling pathway comprises inhibiting one or more non-canonical HIPPO signaling agonists selected from aPKC, Tao1, Msn, PRP4k, and homologs thereof.

\* \* \* \* \*

SEQUENCE LISTING

```
<160> NUMBER OF SEQ ID NOS: 31

<210> SEQ ID NO 1
<211> LENGTH: 1464
<212> TYPE: DNA
<213> ORGANISM: Homo sapiens

<400> SEQUENCE: 1
atggatcccg ggcagcagcc gccgcctcaa ccggcccccc agggccaagg gcagccgcct      60
tcgcagcccc cgcaggggca gggcccgccg tccggacccg ggcaaccggc acccgcggcg     120
acccaggcgg cgccgcaggc accccccgcc gggcatcaga tcgtgcacgt ccgcggggac     180
tcggagaccg acctggaggc gctctttaac gccgtcatga accccaagac ggccaacgtg     240
ccccagaccg tgcccatgag gctccggaag ctgccccgact ccttcttcaa gccgccggag    300
cccaaatccc actcccgaca ggccagtact gatgcaggca ctgcaggagc cctgactcca     360
cagcatgttc gagctcatgc ctctccagct tctctgcagt tgggagctgt ttctcctggg     420
acactgaccc ccactggagt agtctctggc ccagcagcta cacccacagc tcagcatctt     480
cgacagtctt cttttgagat acctgatgat gtacctctgc cagcaggttg ggagatggca     540
aagacatctt ctggtcagag atacttctta aatcacatcg atcagacaac aacatggcag     600
gaccccagga aggccatgct gtcccagatg aacgtcacag cccccaccag tccaccagtg     660
cagcagaata tgatgaactc ggcttcaggt cctcttcctg atggatggga acaagccatg     720
actcaggatg gagaaattta ctatataaac cataagaaca gaccaccctc ttggctagac     780
ccaaggcttg accctcgttt tgccatgaac cagagaatca gtcagagtgc tccagtgaaa     840
cagccaccac ccctggctcc ccagagccca cagggaggcg tcatgggtgg cagcaactcc     900
aaccagcagc aacagatgcg actgcagcaa ctgcagatgg agaaggagag gctgcggctg     960
aaacagcaag aactgcttcg gcaggagtta gccctgcgta gccagttacc aacactggag    1020
caggatggtg ggactcaaaa tccagtgtct tctcccggga tgtctcagga attgagaaca    1080
atgacgacca atagctcaga tccttttcct aacagtggca cctatcactc tcgagatgag    1140
agtacagaca gtggactaag catgagcagc tacagtgtcc ctcgaacccc agatgacttc    1200
ctgaacagtg tggatgagat ggatacaggt gatactatca ccaaagcac cctgccctca    1260
```

```
cagcagaacc gtttcccaga ctaccttgaa gccattcctg ggacaaatgt ggaccttgga    1320
acactggaag gagatggaat gaacatagaa ggagaggagc tgatgccaag tctgcaggaa    1380
gctttgagtt ctgacatcct taatgacatg gagtctgttt tggctgccac caagctagat    1440
aaagaaagct ttcttacatg gtta                                           1464
```

<210> SEQ ID NO 2
<211> LENGTH: 1467
<212> TYPE: DNA
<213> ORGANISM: Homo sapiens
<300> PUBLICATION INFORMATION:
<308> DATABASE ACCESSION NUMBER: NCBI/NM_001195044.1
<309> DATABASE ENTRY DATE: 2018-03-29
<313> RELEVANT RESIDUES IN SEQ ID NO: (1)..(1467)

<400> SEQUENCE: 2

```
atggatcccg ggcagcagcc gccgcctcaa ccggcccccc agggccaagg gcagccgcct     60
tcgcagcccc cgcaggggca gggcccgccg tccggacccg gcaaccggc acccgcggcg    120 acccaggcgc cgccgcaggc accccccgcc gggcatcaga tcgtgcacgt ccgcggggac    180
tcggagaccg acctggaggc gctcttcaac gccgtcatga cccccaagac ggccaacgtg    240
ccccagaccc tgcccatgag gctccggaag ctgcccgact ccttcttcaa gccgccggag    300
cccaaatccc actcccgaca ggccagtact gatgcaggca ctgcaggagc cctgactcca    360
cagcatgttc gagctcattc ctctccagct tctctgcagt tgggagctgt ttctcctggg    420
acactgaccc ccactggagt agtctctggc ccagcagcta cacccacagc tcagcatctt    480
cgacagtctt cttttgagat acctgatgat gtacctctgc cagcaggttg ggagatggca    540
aagacatctt ctggtcagag atacttctta aatcacatcg atcagacaac aacatggcag    600
gaccccagga aggccatgct gtcccagatg aacgtcacag cccccaccag tccaccagtg    660
cagcagaata tgatgaactc ggcttcaggt cctcttcctg atggatggga caagccatg    720 actcaggatg gagaaattta ctatataaac cataagaaca agaccaccc ttggctagac    780 ccaaggcttg accctcgttt tgccatgaac cagagaatca gtcagagtgc tccagtgaaa    840
cagccaccac ccctggctcc ccagagccca caggaggcg tcatgggtgg cagcaactcc    900
aaccagcagc aacagatgcg actgcagcaa ctgcagatgg agaaggagag gctgcggctg    960
aaacagcaag aactgcttcg gcaggagtta gccctgcgta gccagttacc aacactggag   1020
caggatggtg ggactcaaaa tccagtgtct tctcccggga tgtctcagga attgagaaca   1080
atgacgacca atagctcaga tccttttcctt aacagtggca cctatcactc tcgagatgag   1140
agtacagaca gtggactaag catgagcagc tacagtgtcc ctcgaacccc agatgacttc   1200
ctgaacagtg tggatgagat ggatacaggt gatactatca ccaaagcac cctgccctca   1260 cagcagaacc gtttcccaga ctaccttgaa gccattcctg ggacaaatgt ggaccttgga   1320
acactggaag gagatggaat gaacatagaa ggagaggagc tgatgccaag tctgcaggaa   1380
gctttgagtt ctgacatcct taatgacatg gagtctgttt tggctgccac caagctagat   1440
aaagaaagct ttcttacatg gttatag                                      1467
```

<210> SEQ ID NO 3
<211> LENGTH: 1200
<212> TYPE: DNA
<213> ORGANISM: Homo sapiens

<400> SEQUENCE: 3

```
atgaatccgg cctcggcgcc ccctccgctc ccgccgcctg ggcagcaagt gatccacgtc     60
```

| | | |
|---|---|---|
| acgcaggacc tagacacaga cctcgaagcc ctcttcaact ctgtcatgaa tccgaagcct | 120 | |
| agctcgtggc ggaagaagat cctgccggag tctttcttta aggagcctga ttcgggctcg | 180 | |
| cactcgcgcc agtccagcac cgactcgtcg ggcggccacc cggggcctcg actggctggg | 240 | |
| ggtgcccagc atgtccgctc gcacgcgtcg cccgcgtccc tgcagctggg caccggcgcg | 300 | |
| ggtgctgcgg gtagccccgc gcagcagcac gcgcacctcc gccagcagtc ctacgacgtg | 360 | |
| accgacgagc tgccactgcc cccgggctgg gagatgacct tcacggccac tggccagagg | 420 | |
| tacttcctca atcacataga aaaaatcacc acatggcaag accctaggaa ggcgatgaat | 480 | |
| cagcctctga atcatatgaa cctccaccct gccgtcagtt ccacaccagt gcctcagagg | 540 | |
| tccatggcag tatcccagcc aaatctcgtg atgaatcacc aacaccagca gcagatggcc | 600 | |
| cccagtaccc tgagccagca gaaccacccc actcagaacc cacccgcagg gctcatgagt | 660 | |
| atgcccaatg cgctgaccac tcagcagcag cagcagcaga aactgcggct tcagagaatc | 720 | |
| cagatggaga gagaaaggat tcgaatgcgc caagaggagc tcatgaggca ggaagctgcc | 780 | |
| ctctgtcgac agctccccat ggaagctgag actcttgccc cagttcaggc tgctgtcaac | 840 | |
| ccacccacga tgaccccaga catgagatcc atcactaata atagctcaga tccttcctc | 900 | |
| aatggagggc catatcattc gagggagcag agcactgaca gtggcctggg gttagggtgc | 960 | |
| tacagtgtcc ccacaactcc ggaggacttc ctcagcaatg tggatgagat ggatacagga | 1020 | |
| gaaaacgcag acaaacacc catgaacatc aatccccaac agacccgttt ccctgatttc | 1080 | |
| cttgactgtc ttccaggaac aaacgttgac ttaggaactt tggaatctga agacctgatc | 1140 | |
| cccctcttca atgatgtaga gtctgctctg aacaaaagtg agccctttct aacctggctg | 1200 | |

<210> SEQ ID NO 4
<211> LENGTH: 1203
<212> TYPE: DNA
<213> ORGANISM: Homo sapiens
<300> PUBLICATION INFORMATION:
<308> DATABASE ACCESSION NUMBER: NCBI/ 25937
<309> DATABASE ENTRY DATE: 2018-04-16
<313> RELEVANT RESIDUES IN SEQ ID NO: (1)..(1203)

<400> SEQUENCE: 4

| | | |
|---|---|---|
| atgaatccgg cctcggcgcc ccctccgctc ccgccgcctg gcagcaagt gatccacgtc | 60 | |
| acgcaggacc tagacacaga cctcgaagcc ctcttcaact ctgtcatgaa tccgaagcct | 120 | |
| agctcgtggc ggaagaagat cctgccggag tctttcttta aggagcctga ttcgggctcg | 180 | |
| cactcgcgcc agtccagcac cgactcgtcg ggcggccacc cggggcctcg actggctggg | 240 | |
| ggtgcccagc atgtccgctc gcactcgtcg cccgcgtccc tgcagctggg caccggcgcg | 300 | |
| ggtgctgcgg gtagccccgc gcagcagcac gcgcacctcc gccagcagtc ctacgacgtg | 360 | |
| accgacgagc tgccactgcc cccgggctgg gagatgacct tcacggccac tggccagagg | 420 | |
| tacttcctca atcacataga aaaaatcacc acatggcaag accctaggaa ggcgatgaat | 480 | |
| cagcctctga atcatatgaa cctccaccct gccgtcagtt ccacaccagt gcctcagagg | 540 | |
| tccatggcag tatcccagcc aaatctcgtg atgaatcacc aacaccagca gcagatggcc | 600 | |
| cccagtaccc tgagccagca gaaccacccc actcagaacc cacccgcagg gctcatgagt | 660 | |
| atgcccaatg cgctgaccac tcagcagcag cagcagcaga aactgcggct tcagagaatc | 720 | |
| cagatggaga gagaaaggat tcgaatgcgc caagaggagc tcatgaggca ggaagctgcc | 780 | |
| ctctgtcgac agctccccat ggaagctgag actcttgccc cagttcaggc tgctgtcaac | 840 | |

```
ccacccacga tgaccccaga catgagatcc atcactaata atagctcaga tcctttcctc    900
aatggagggc catatcattc gagggagcag agcactgaca gtggcctggg gttagggtgc    960
tacagtgtcc ccacaactcc ggaggacttc ctcagcaatg tggatgagat ggatacagga   1020
gaaaacgcag acaaacacc catgaacatc aatccccaac agaccgtttt ccctgatttc    1080
cttgactgtc ttccaggaac aaacgttgac ttaggaactt tggaatctga agacctgatc   1140
cccctcttca atgatgtaga gtctgctctg aacaaaagtg agcccttcct aacctggctg   1200
taa                                                                 1203
```

<210> SEQ ID NO 5
<211> LENGTH: 488
<212> TYPE: PRT
<213> ORGANISM: Homo sapiens

<400> SEQUENCE: 5

```
Met Asp Pro Gly Gln Gln Pro Pro Gln Pro Ala Pro Gln Gly Gln
1               5                   10                  15

Gly Gln Pro Pro Ser Gln Pro Pro Gly Gln Gly Pro Pro Ser Gly
                20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
            50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ala Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Pro Leu Ala Pro Gln
        275                 280                 285

Ser Pro Gln Gly Gly Val Met Gly Gly Ser Asn Ser Asn Gln Gln Gln
    290                 295                 300
```

-continued

```
Gln Met Arg Leu Gln Gln Leu Gln Met Glu Lys Glu Arg Leu Arg Leu
305                 310                 315                 320

Lys Gln Gln Glu Leu Leu Arg Gln Glu Leu Ala Leu Arg Ser Gln Leu
            325                 330                 335

Pro Thr Leu Glu Gln Asp Gly Gly Thr Gln Asn Pro Val Ser Ser Pro
            340                 345                 350

Gly Met Ser Gln Glu Leu Arg Thr Met Thr Thr Asn Ser Ser Asp Pro
            355                 360                 365

Phe Leu Asn Ser Gly Thr Tyr His Ser Arg Asp Glu Ser Thr Asp Ser
    370                 375                 380

Gly Leu Ser Met Ser Ser Tyr Ser Val Pro Arg Thr Pro Asp Asp Phe
385                 390                 395                 400

Leu Asn Ser Val Asp Glu Met Asp Thr Gly Asp Thr Ile Asn Gln Ser
                405                 410                 415

Thr Leu Pro Ser Gln Gln Asn Arg Phe Pro Asp Tyr Leu Glu Ala Ile
            420                 425                 430

Pro Gly Thr Asn Val Asp Leu Gly Thr Leu Glu Gly Asp Gly Met Asn
            435                 440                 445

Ile Glu Gly Glu Glu Leu Met Pro Ser Leu Gln Glu Ala Leu Ser Ser
450                 455                 460

Asp Ile Leu Asn Asp Met Glu Ser Val Leu Ala Ala Thr Lys Leu Asp
465                 470                 475                 480

Lys Glu Ser Phe Leu Thr Trp Leu
                485
```

```
<210> SEQ ID NO 6
<211> LENGTH: 488
<212> TYPE: PRT
<213> ORGANISM: Homo sapiens
<300> PUBLICATION INFORMATION:
<308> DATABASE ACCESSION NUMBER: NCBI/ NP_001181973.1
<309> DATABASE ENTRY DATE: 2018-03-29
<313> RELEVANT RESIDUES IN SEQ ID NO: (1)..(488)

<400> SEQUENCE: 6

Met Asp Pro Gly Gln Gln Pro Pro Gln Pro Ala Pro Gln Gly Gln Gln
1               5                   10                  15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
```

```
                        165                 170                 175
Trp Glu Met Ala Lys Thr Ser Ser Gly Gln Arg Tyr Phe Leu Asn His
                180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Val Gln Gln Asn Met
        210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
                260                 265                 270

Ile Ser Gln Ser Ala Pro Val Lys Gln Pro Pro Leu Ala Pro Gln
            275                 280                 285

Ser Pro Gln Gly Gly Val Met Gly Gly Ser Asn Ser Asn Gln Gln Gln
            290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Glu Leu Ala Leu Arg Ser Gln Leu
                325                 330                 335

Pro Thr Leu Glu Gln Asp Gly Gly Thr Gln Asn Pro Val Ser Ser Pro
            340                 345                 350

Gly Met Ser Gln Glu Leu Arg Thr Met Thr Thr Asn Ser Ser Asp Pro
            355                 360                 365

Phe Leu Asn Ser Gly Thr Tyr His Ser Arg Asp Glu Ser Thr Asp Ser
        370                 375                 380

Gly Leu Ser Met Ser Ser Tyr Ser Val Pro Arg Thr Pro Asp Asp Phe
385                 390                 395                 400

Leu Asn Ser Val Asp Glu Met Asp Thr Gly Asp Thr Ile Asn Gln Ser
                405                 410                 415

Thr Leu Pro Ser Gln Gln Asn Arg Phe Pro Asp Tyr Leu Glu Ala Ile
            420                 425                 430

Pro Gly Thr Asn Val Asp Leu Gly Thr Leu Glu Gly Asp Gly Met Asn
            435                 440                 445

Ile Glu Gly Glu Glu Leu Met Pro Ser Leu Gln Glu Ala Leu Ser Ser
            450                 455                 460

Asp Ile Leu Asn Asp Met Glu Ser Val Leu Ala Ala Thr Lys Leu Asp
465                 470                 475                 480

Lys Glu Ser Phe Leu Thr Trp Leu
                485
```

<210> SEQ ID NO 7
<211> LENGTH: 472
<212> TYPE: PRT
<213> ORGANISM: Mus musculus
<300> PUBLICATION INFORMATION:
<308> DATABASE ACCESSION NUMBER: NCBI/NP_001164618.1
<309> DATABASE ENTRY DATE: 2018-04-08
<313> RELEVANT RESIDUES IN SEQ ID NO: (1)..(472)

<400> SEQUENCE: 7

```
Met Glu Pro Ala Gln Gln Pro Pro Gln Pro Ala Pro Gln Gly Pro
1               5                   10                  15

Ala Pro Pro Ser Val Ser Pro Ala Gly Thr Pro Ala Ala Pro Pro Ala
            20                  25                  30
```

```
Pro Pro Ala Gly His Gln Val His Val Arg Gly Asp Ser Glu Thr
        35                  40                  45

Asp Leu Glu Ala Leu Phe Asn Ala Val Met Asn Pro Lys Thr Ala Asn
50                      55                  60

Val Pro Gln Thr Val Pro Met Arg Leu Arg Lys Leu Pro Asp Ser Phe
65                  70                  75                  80

Phe Lys Pro Pro Glu Pro Lys Ser His Ser Arg Gln Ala Ser Thr Asp
                85                  90                  95

Ala Gly Thr Ala Gly Ala Leu Thr Pro Gln His Val Arg Ala His Ser
            100                 105                 110

Ser Pro Ala Ser Leu Gln Leu Gly Ala Val Ser Pro Gly Thr Leu Thr
        115                 120                 125

Ala Ser Gly Val Val Ser Gly Pro Ala Ala Pro Ala Ala Gln His
        130                 135                 140

Leu Arg Gln Ser Ser Phe Glu Ile Pro Asp Asp Val Pro Leu Pro Ala
145                 150                 155                 160

Gly Trp Glu Met Ala Lys Thr Ser Ser Gly Gln Arg Tyr Phe Leu Asn
                165                 170                 175

His Asn Asp Gln Thr Thr Thr Trp Gln Asp Pro Arg Lys Ala Met Leu
            180                 185                 190

Ser Gln Leu Asn Val Pro Ala Pro Ala Ser Pro Ala Val Pro Gln Thr
        195                 200                 205

Leu Met Asn Ser Ala Ser Gly Pro Leu Pro Asp Gly Trp Glu Gln Ala
210                 215                 220

Met Thr Gln Asp Gly Glu Val Tyr Tyr Ile Asn His Lys Asn Lys Thr
225                 230                 235                 240

Thr Ser Trp Leu Asp Pro Arg Leu Asp Pro Arg Phe Ala Met Asn Gln
                245                 250                 255

Arg Ile Thr Gln Ser Ala Pro Val Lys Gln Pro Pro Pro Leu Ala Pro
            260                 265                 270

Gln Ser Pro Gln Gly Gly Val Leu Gly Gly Ser Ser Asn Gln Gln
        275                 280                 285

Gln Gln Ile Gln Leu Gln Leu Gln Met Glu Lys Glu Arg Leu Arg
290                 295                 300

Leu Lys Gln Gln Glu Leu Phe Arg Gln Glu Leu Ala Leu Arg Ser Gln
305                 310                 315                 320

Leu Pro Thr Leu Glu Gln Asp Gly Gly Thr Pro Asn Ala Val Ser Ser
                325                 330                 335

Pro Gly Met Ser Gln Glu Leu Arg Thr Met Thr Thr Asn Ser Ser Asp
            340                 345                 350

Pro Phe Leu Asn Ser Gly Thr Tyr His Ser Arg Asp Glu Ser Thr Asp
        355                 360                 365

Ser Gly Leu Ser Met Ser Ser Tyr Ser Ile Pro Arg Thr Pro Asp Asp
370                 375                 380

Phe Leu Asn Ser Val Asp Glu Met Asp Thr Gly Asp Thr Ile Ser Gln
385                 390                 395                 400

Ser Thr Leu Pro Ser Gln Gln Ser Arg Phe Pro Asp Tyr Leu Glu Ala
                405                 410                 415

Leu Pro Gly Thr Asn Val Asp Leu Gly Thr Leu Glu Gly Asp Ala Met
            420                 425                 430

Asn Ile Glu Gly Glu Glu Leu Met Pro Ser Leu Gln Glu Ala Leu Ser
        435                 440                 445
```

-continued

```
Ser Glu Ile Leu Asp Val Glu Ser Val Leu Ala Ala Thr Lys Leu Asp
    450                 455                 460

Lys Glu Ser Phe Leu Thr Trp Leu
465                 470

<210> SEQ ID NO 8
<211> LENGTH: 448
<212> TYPE: PRT
<213> ORGANISM: Gallus gallus
<300> PUBLICATION INFORMATION:
<308> DATABASE ACCESSION NUMBER: NCBI/NP_990574.1
<309> DATABASE ENTRY DATE: 2017-11-01
<313> RELEVANT RESIDUES IN SEQ ID NO: (1)..(448)

<400> SEQUENCE: 8

Met Asp Pro Gly Gln Pro Gln Pro Gln Gln Pro Pro Gln Ala Ala Gln
1               5                   10                  15

Pro Pro Ala Pro Gln Gln Ala Ala Pro Gln Pro Pro Gly Ala Gly Ser
            20                  25                  30

Gly Ala Pro Gly Gly Ala Ala Gln Pro Pro Gly Ala Gly Pro Pro Pro
        35                  40                  45

Ala Gly His Gln Ile Val His Val Arg Gly Asp Ser Glu Thr Asp Leu
    50                  55                  60

Glu Ala Leu Phe Asn Ala Val Met Asn Pro Lys Gly Ala Asn Val Pro
65                  70                  75                  80

His Thr Leu Pro Met Arg Leu Arg Lys Leu Pro Asp Ser Phe Phe Lys
                85                  90                  95

Pro Pro Glu Pro Lys Ala His Ser Arg Gln Ala Ser Thr Asp Ala Gly
            100                 105                 110

Thr Ala Gly Ala Leu Thr Pro Gln His Val Arg Ala His Ser Ser Pro
        115                 120                 125

Ala Ser Leu Gln Leu Gly Ala Val Ser Pro Gly Thr Leu Thr Pro Ser
    130                 135                 140

Gly Val Val Thr Gly Pro Gly Ala Pro Ser Ser Gln His Leu Arg Gln
145                 150                 155                 160

Ser Ser Phe Glu Ile Pro Asp Asp Val Pro Leu Pro Pro Gly Trp Glu
                165                 170                 175

Met Ala Lys Thr Pro Ser Gly Gln Arg Tyr Phe Leu Asn His Ile Asp
            180                 185                 190

Gln Thr Thr Thr Trp Gln Asp Pro Arg Lys Ala Met Leu Ser Gln Met
        195                 200                 205

Asn Val Thr Ala Pro Thr Ser Pro Pro Val Gln Gln Asn Leu Met Asn
    210                 215                 220

Ser Ala Ser Ala Met Asn Gln Arg Ile Ser Gln Ser Ala Pro Val Lys
225                 230                 235                 240

Gln Pro Pro Pro Leu Ala Pro Gln Ser Pro Gln Gly Gly Val Met Gly
                245                 250                 255

Gly Ser Ser Ser Asn Gln Gln Gln Gln Met Arg Leu Gln Gln Leu Gln
            260                 265                 270

Met Glu Lys Glu Arg Leu Arg Leu Lys His Gln Glu Leu Leu Arg Gln
        275                 280                 285

Glu Leu Ala Leu Arg Ser Gln Leu Pro Thr Met Glu Gln Asp Gly Gly
    290                 295                 300

Ser Gln Asn Pro Val Ser Ser Pro Gly Met Ser Gln Glu Leu Arg Thr
305                 310                 315                 320

Met Thr Thr Asn Ser Ser Asp Pro Phe Leu Asn Ser Gly Thr Tyr His
```

-continued

```
                325                 330                 335
    Ser Arg Asp Glu Ser Thr Asp Ser Gly Leu Ser Met Ser Ser Tyr Ser
                340                 345                 350

Val Pro Arg Thr Pro Asp Asp Phe Leu Asn Ser Val Asp Glu Met Asp
                355                 360                 365

Thr Gly Asp Ser Ile Ser Gln Ser Asn Ile Pro Ser His Gln Asn Arg
                370                 375                 380

Phe Pro Asp Tyr Leu Glu Ala Ile Pro Gly Thr Asn Val Asp Leu Gly
    385                 390                 395                 400

Thr Leu Glu Gly Asp Gly Met Asn Ile Glu Gly Glu Leu Met Pro
                405                 410                 415

Ser Leu Gln Glu Ala Leu Ser Ser Asp Ile Leu Asn Asp Met Glu Ser
                420                 425                 430

Val Leu Ala Ala Thr Lys Pro Asp Lys Glu Ser Phe Leu Thr Trp Leu
                435                 440                 445
```

<210> SEQ ID NO 9
<211> LENGTH: 505
<212> TYPE: PRT
<213> ORGANISM: Sus scrofa
<220> FEATURE:
<221> NAME/KEY: misc_feature
<222> LOCATION: (48)..(48)
<223> OTHER INFORMATION: Xaa can be any naturally occurring amino acid
<300> PUBLICATION INFORMATION:
<308> DATABASE ACCESSION NUMBER: NCBI/XP_020918365.1
<309> DATABASE ENTRY DATE: 2017-05-13
<313> RELEVANT RESIDUES IN SEQ ID NO: (1)..(505)

<400> SEQUENCE: 9

```
Met Asp Pro Gly Gln Gln Pro Pro Gln Pro Ala Pro Gln Gly
1               5                   10                  15

Gln Gly Gln Pro Pro Ala Gln Pro Gln Gly Gln Gly Pro Pro Ser
            20                  25                  30

Gly Pro Gly Gln Pro Ala Pro Pro Gly Ser Gln Ala Ala Thr Gln Xaa
            35                  40                  45

Pro Pro Ala Gly His Gln Ile Val His Val Arg Gly Asp Ser Glu Thr
50                  55                  60

Asp Leu Glu Ala Leu Phe Asn Ala Val Met Asn Pro Lys Thr Ala Asn
65                  70                  75                  80

Val Pro Gln Thr Val Pro Met Arg Leu Arg Lys Leu Pro Asp Ser Phe
            85                  90                  95

Phe Lys Pro Pro Glu Pro Lys Ser His Ser Arg Gln Ala Ser Thr Asp
            100                 105                 110

Ala Gly Thr Ala Gly Ala Leu Thr Pro Gln His Val Arg Ala His Ser
            115                 120                 125

Ser Pro Ala Ser Leu Gln Leu Gly Ala Ile Ser Pro Gly Thr Leu Thr
            130                 135                 140

Pro Thr Gly Val Val Ser Gly Pro Ala Ala Thr Pro Thr Ala Gln His
145                 150                 155                 160

Leu Arg Gln Ser Ser Phe Glu Ile Pro Asp Asp Val Pro Leu Pro Ala
            165                 170                 175

Gly Trp Glu Met Ala Lys Thr Ser Ser Gly Gln Arg Tyr Phe Leu Asn
            180                 185                 190

His Ile Asp Gln Thr Thr Thr Trp Gln Asp Pro Arg Lys Ala Met Leu
            195                 200                 205

Ser Gln Met Asn Val Thr Ala Pro Thr Ser Pro Pro Val Gln Gln Asn
```

```
Met Met Asn Ser Ala Ser Gly Pro Leu Pro Asp Gly Trp Glu Gln Ala
225                 230                 235                 240

Met Thr Gln Asp Gly Glu Ile Tyr Tyr Ile Asn His Lys Asn Lys Thr
            245                 250                 255

Thr Ser Trp Leu Asp Pro Arg Leu Asp Pro Arg Phe Ala Met Asn Gln
        260                 265                 270

Arg Ile Ser Gln Ser Ala Pro Val Lys Gln Pro Pro Leu Ala Pro
    275                 280                 285

Gln Ser Pro Gln Gly Gly Val Met Gly Gly Ser Ser Asn Gln Gln
290                 295                 300

Gln Gln Met Arg Leu Gln Gln Leu Gln Met Glu Lys Glu Arg Leu Arg
305                 310                 315                 320

Leu Lys Gln Gln Glu Leu Leu Arg Gln Ala Met Arg Asn Ile Asn Pro
                325                 330                 335

Ser Thr Ala Asn Ser Pro Lys Cys Gln Glu Leu Ala Leu Arg Ser Gln
                340                 345                 350

Leu Pro Thr Leu Glu Gln Asp Gly Gly Thr Gln Asn Pro Val Ser Ser
            355                 360                 365

Pro Gly Met Ser Gln Glu Leu Arg Thr Met Thr Thr Asn Ser Ser Asp
    370                 375                 380

Pro Phe Leu Asn Ser Gly Thr Tyr His Ser Arg Asp Glu Ser Thr Asp
385                 390                 395                 400

Ser Gly Leu Ser Met Ser Ser Tyr Ser Val Pro Arg Thr Pro Asp Asp
                405                 410                 415

Phe Leu Asn Ser Val Asp Glu Met Asp Thr Gly Asp Thr Ile Asn Gln
            420                 425                 430

Ser Thr Leu Pro Ser Gln Asn Arg Phe Pro Asp Tyr Leu Glu Ala
        435                 440                 445

Ile Pro Gly Thr Asn Val Asp Leu Gly Thr Leu Glu Gly Asp Gly Met
    450                 455                 460

Asn Ile Glu Gly Glu Glu Leu Met Pro Ser Leu Gln Glu Ala Leu Ser
465                 470                 475                 480

Ser Asp Ile Leu Asn Asp Met Glu Ser Val Leu Ala Ala Thr Lys Leu
                485                 490                 495

Asp Lys Glu Ser Phe Leu Thr Trp Leu
            500                 505

<210> SEQ ID NO 10
<211> LENGTH: 432
<212> TYPE: PRT
<213> ORGANISM: Bos taurus
<300> PUBLICATION INFORMATION:
<308> DATABASE ACCESSION NUMBER: NCBI/XP_015321922.1
<309> DATABASE ENTRY DATE: 2016-01-26
<313> RELEVANT RESIDUES IN SEQ ID NO: (1)..(432)

<400> SEQUENCE: 10

Met Asn Pro Lys Thr Ala Asn Val Pro Gln Thr Val Pro Met Arg Leu
1               5                   10                  15

Arg Lys Leu Pro Asp Ser Phe Phe Lys Pro Pro Glu Pro Lys Ser His
            20                  25                  30

Ser Arg Gln Ala Ser Thr Asp Ala Gly Thr Ala Gly Ala Leu Thr Pro
        35                  40                  45

Gln His Val Arg Ala His Ser Ser Pro Ala Ser Leu Gln Leu Gly Ala
    50                  55                  60
```

Val Ser Pro Gly Thr Leu Thr Pro Thr Gly Val Ser Gly Pro Ala
65                  70                  75                  80

Ala Ala Pro Ala Ala Gln His Leu Arg Gln Ser Ser Phe Glu Ile Pro
            85                  90                  95

Asp Asp Val Pro Leu Pro Ala Gly Trp Glu Met Ala Lys Thr Ser Ser
            100                 105                 110

Gly Gln Arg Tyr Phe Leu Asn His Ile Asp Gln Thr Thr Thr Trp Gln
            115                 120                 125

Asp Pro Arg Lys Ala Met Leu Ser Gln Met Asn Val Thr Ala Pro Thr
            130                 135                 140

Ser Pro Pro Val Gln Gln Asn Met Met Asn Ser Ala Ser Gly Pro Leu
145                 150                 155                 160

Pro Asp Gly Trp Glu Gln Ala Met Thr Gln Asp Gly Glu Ile Tyr Tyr
                165                 170                 175

Ile Asn His Lys Asn Lys Thr Thr Ser Trp Leu Asp Pro Arg Leu Asp
                180                 185                 190

Pro Arg Phe Ala Met Asn Gln Arg Ile Ser Gln Ser Ala Pro Val Lys
            195                 200                 205

Gln Pro Pro Pro Leu Ala Pro Gln Ser Pro Gln Gly Gly Val Leu Gly
210                 215                 220

Gly Gly Ser Ser Asn Gln Gln Gln Met Arg Leu Gln Gln Leu Gln
225                 230                 235                 240

Met Glu Lys Glu Arg Leu Arg Leu Lys Gln Gln Glu Leu Leu Arg Gln
                245                 250                 255

Ala Met Arg Asn Ile Asn Pro Ser Thr Ala Asn Ser Pro Lys Cys Gln
            260                 265                 270

Glu Leu Ala Leu Arg Ser Gln Leu Pro Thr Leu Glu Gln Asp Gly Gly
            275                 280                 285

Thr Gln Asn Pro Val Ser Ser Pro Gly Met Ser Gln Glu Leu Arg Thr
290                 295                 300

Met Thr Thr Asn Ser Ser Asp Pro Phe Leu Asn Ser Gly Thr Tyr His
305                 310                 315                 320

Ser Arg Asp Glu Ser Thr Asp Ser Gly Leu Ser Met Ser Ser Tyr Ser
                325                 330                 335

Val Pro Arg Thr Pro Asp Asp Phe Leu Asn Ser Val Asp Glu Met Asp
            340                 345                 350

Thr Gly Asp Thr Ile Asn Gln Ser Thr Leu Pro Ser Gln Gln Asn Arg
            355                 360                 365

Phe Pro Asp Tyr Leu Glu Ala Ile Pro Gly Thr Asn Val Asp Leu Gly
            370                 375                 380

Thr Leu Glu Gly Asp Gly Met Asn Ile Glu Gly Glu Leu Met Pro
385                 390                 395                 400

Ser Leu Gln Glu Ala Leu Ser Ser Asp Ile Leu Asn Asp Met Glu Ser
                405                 410                 415

Val Leu Ala Ala Thr Lys Leu Asp Lys Glu Ser Phe Leu Thr Trp Leu
            420                 425                 430

<210> SEQ ID NO 11
<211> LENGTH: 437
<212> TYPE: PRT
<213> ORGANISM: Oreochromis niloticus
<300> PUBLICATION INFORMATION:
<308> DATABASE ACCESSION NUMBER: NCBI/XP_003450207.1
<309> DATABASE ENTRY DATE: 2016-12-05
<313> RELEVANT RESIDUES IN SEQ ID NO: (1)..(437)

<400> SEQUENCE: 11

Met Asp Pro Ser Gln His Asn Pro Pro Ala Gly His Gln Ile Val His
1               5                   10                  15

Val Arg Gly Asp Ser Glu Thr Asp Leu Glu Ala Leu Phe Asn Ala Val
            20                  25                  30

Met Asn Pro Lys Val Asn Thr Val Pro His Ser Val Pro Met Arg Met
        35                  40                  45

Arg Lys Leu Pro Asp Ser Phe Phe Lys Pro Pro Glu Pro Lys Ser His
    50                  55                  60

Ser Arg Gln Ala Ser Thr Asp Ala Gly Ser Gly Gly Val Leu Ile Pro
65                  70                  75                  80

His His Val Arg Ala His Ser Ser Pro Ala Ser Leu Gln Leu Gly Ala
                85                  90                  95

Val Ser Gly Gly Ser Leu Ser Gly Met Gly Ser Thr Gly Ala Ser Pro
            100                 105                 110

Gln His Leu Arg Gln Ser Ser Tyr Glu Ile Pro Asp Asp Met Pro Leu
        115                 120                 125

Pro Asp Gly Trp Glu Met Ala Lys Thr Ala Ser Gly Gln Arg Tyr Phe
    130                 135                 140

Leu Asn His Ile Asp Gln Thr Thr Thr Trp Gln Asp Pro Arg Lys Ala
145                 150                 155                 160

Met Leu Gln Met Asn Gln Pro Pro Pro Ser Ser Val Pro Val Gln
            165                 170                 175

Pro Gln Pro Ile Met Asn Pro Ala Ser Gly Pro Leu Pro Asp Gly Trp
    180                 185                 190

Glu Gln Ala Ile Thr Ala Glu Gly Glu Ile Tyr Tyr Ile Asn His Lys
        195                 200                 205

Asn Lys Thr Thr Ser Trp Leu Asp Pro Arg Leu Glu Pro Arg Tyr Ala
    210                 215                 220

Leu Asn Gln Gln Arg Ile Ser Gln Ser Ala Pro Val Lys Pro Pro Gly
225                 230                 235                 240

Gln Leu Pro Pro Ser Ile Ser Gly Val Met Gly Ser Asn Asn Gln Met
            245                 250                 255

Arg Leu Gln Gln Ile Glu Lys Glu Arg Leu Arg Leu Lys Gln Gln Glu
        260                 265                 270

Leu Leu Arg Gln Arg Pro Gln Glu Leu Ala Leu Arg Asn Gln Leu Pro
    275                 280                 285

Thr Ser Met Asp Gln Asp Gly Ser Thr Asn Pro Val Ser Ser Pro Met
290                 295                 300

Ala Gln Asp Ala Arg Thr Met Thr Ala Asn Ser Ser Asp Pro Phe Leu
305                 310                 315                 320

Asn Ser Gly Thr Tyr His Ser Arg Asp Glu Ser Thr Asp Ser Gly Leu
            325                 330                 335

Ser Met Ser Ser Tyr Ser Val Pro Arg Thr Pro Asp Asp Phe Leu Asn
        340                 345                 350

Ser Val Asp Glu Met Asp Thr Gly Asp Pro Leu Ala Pro Ser Met Ala
    355                 360                 365

Thr Gln Pro Ser Arg Phe Pro Asp Tyr Leu Asp Thr Ile Pro Gly Thr
        370                 375                 380

Asp Val Asp Leu Gly Thr Leu Glu Gly Glu Ser Met Ala Val Glu Gly
385                 390                 395                 400

Glu Glu Leu Met Pro Ser Leu Gln Glu Ala Leu Ser Ser Asp Ile Leu 405                 410                 415
Asn Asp Met Glu Ser Val Leu Ala Ala Thr Lys Leu Asp Lys Glu Ser
            420                 425                 430

Phe Leu Thr Trp Leu
        435

<210> SEQ ID NO 12
<211> LENGTH: 400
<212> TYPE: PRT
<213> ORGANISM: Homo sapiens

<400> SEQUENCE: 12

Met Asn Pro Ala Ser Ala Pro Pro Pro Leu Pro Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ala Ser Pro Ala Ser Leu Gln Leu
                85                  90                  95

Gly Thr Gly Ala Gly Ala Ala Gly Ser Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140

His Ile Glu Lys Ile Thr Thr Trp Gln Asp Pro Arg Lys Ala Met Asn
145                 150                 155                 160

Gln Pro Leu Asn His Met Asn Leu His Pro Ala Val Ser Ser Thr Pro
                165                 170                 175

Val Pro Gln Arg Ser Met Ala Val Ser Gln Pro Asn Leu Val Met Asn
            180                 185                 190

His Gln His Gln Gln Met Ala Pro Ser Thr Leu Ser Gln Gln Asn
        195                 200                 205

His Pro Thr Gln Asn Pro Pro Ala Gly Leu Met Ser Met Pro Asn Ala
    210                 215                 220

Leu Thr Thr Gln Gln Gln Gln Gln Lys Leu Arg Leu Gln Arg Ile
225                 230                 235                 240

Gln Met Glu Arg Glu Arg Ile Arg Met Arg Gln Glu Glu Leu Met Arg
                245                 250                 255

Gln Glu Ala Ala Leu Cys Arg Gln Leu Pro Met Glu Ala Glu Thr Leu
            260                 265                 270

Ala Pro Val Gln Ala Ala Val Asn Pro Pro Thr Met Thr Pro Asp Met
        275                 280                 285

Arg Ser Ile Thr Asn Asn Ser Ser Asp Pro Phe Leu Asn Gly Gly Pro
    290                 295                 300

Tyr His Ser Arg Glu Gln Ser Thr Asp Ser Gly Leu Gly Leu Gly Cys
305                 310                 315                 320

Tyr Ser Val Pro Thr Thr Pro Glu Asp Phe Leu Ser Asn Val Asp Glu
                325                 330                 335

```
Met Asp Thr Gly Glu Asn Ala Gly Gln Thr Pro Met Asn Ile Asn Pro
                340                 345                 350

Gln Gln Thr Arg Phe Pro Asp Phe Leu Asp Cys Leu Pro Gly Thr Asn
            355                 360                 365

Val Asp Leu Gly Thr Leu Glu Ser Glu Asp Leu Ile Pro Leu Phe Asn
    370                 375                 380

Asp Val Glu Ser Ala Leu Asn Lys Ser Glu Pro Phe Leu Thr Trp Leu
385                 390                 395                 400
```

<210> SEQ ID NO 13
<211> LENGTH: 400
<212> TYPE: PRT
<213> ORGANISM: Homo sapiens
<300> PUBLICATION INFORMATION:
<308> DATABASE ACCESSION NUMBER: NCBI/25937
<309> DATABASE ENTRY DATE: 2018-04-16
<313> RELEVANT RESIDUES IN SEQ ID NO: (1)..(400)

<400> SEQUENCE: 13

```
Met Asn Pro Ala Ser Ala Pro Pro Pro Leu Pro Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Ser Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140

His Ile Glu Lys Ile Thr Thr Trp Gln Asp Pro Arg Lys Ala Met Asn
145                 150                 155                 160

Gln Pro Leu Asn His Met Asn Leu His Pro Ala Val Ser Ser Thr Pro
                165                 170                 175

Val Pro Gln Arg Ser Met Ala Val Ser Gln Pro Asn Leu Val Met Asn
            180                 185                 190

His Gln His Gln Gln Met Ala Pro Ser Thr Leu Ser Gln Gln Asn
        195                 200                 205

His Pro Thr Gln Asn Pro Pro Ala Gly Leu Met Ser Met Pro Asn Ala
    210                 215                 220

Leu Thr Thr Gln Gln Gln Gln Lys Leu Arg Leu Gln Arg Ile
225                 230                 235                 240

Gln Met Glu Arg Glu Arg Ile Arg Met Arg Gln Glu Glu Leu Met Arg
                245                 250                 255

Gln Glu Ala Ala Leu Cys Arg Gln Leu Pro Met Glu Ala Glu Thr Leu
            260                 265                 270

Ala Pro Val Gln Ala Ala Val Asn Pro Pro Thr Met Thr Pro Asp Met
        275                 280                 285

Arg Ser Ile Thr Asn Asn Ser Ser Asp Pro Phe Leu Asn Gly Gly Pro
```

```
                290                 295                 300
Tyr His Ser Arg Glu Gln Ser Thr Asp Ser Gly Leu Gly Leu Gly Cys
305                 310                 315                 320

Tyr Ser Val Pro Thr Thr Pro Glu Asp Phe Leu Ser Asn Val Asp Glu
                325                 330                 335

Met Asp Thr Gly Glu Asn Ala Gly Gln Thr Pro Met Asn Ile Asn Pro
                340                 345                 350

Gln Gln Thr Arg Phe Pro Asp Phe Leu Asp Cys Leu Pro Gly Thr Asn
                355                 360                 365

Val Asp Leu Gly Thr Leu Glu Ser Glu Asp Leu Ile Pro Leu Phe Asn
                370                 375                 380

Asp Val Glu Ser Ala Leu Asn Lys Ser Glu Pro Phe Leu Thr Trp Leu
385                 390                 395                 400
```

<210> SEQ ID NO 14
<211> LENGTH: 395
<212> TYPE: PRT
<213> ORGANISM: Mus musculus
<300> PUBLICATION INFORMATION:
<308> DATABASE ACCESSION NUMBER: NCBI/NP_033560.1
<309> DATABASE ENTRY DATE: 2016-04-26
<313> RELEVANT RESIDUES IN SEQ ID NO: (1)..(395)

<400> SEQUENCE: 14

```
Met Asn Pro Ser Ser Val Pro His Pro Leu Pro Pro Gly Gln Gln
1               5                   10                  15

Val Ile His Val Thr Gln Asp Leu Asp Thr Asp Leu Glu Ala Leu Phe
                20                  25                  30

Asn Ser Val Met Asn Pro Lys Pro Ser Ser Trp Arg Lys Lys Ile Leu
                35                  40                  45

Pro Glu Ser Phe Phe Lys Glu Pro Asp Ser Gly Ser His Ser Arg Gln
        50                  55                  60

Ser Ser Thr Asp Ser Ser Gly Gly His Pro Gly Pro Arg Leu Ala Gly
65              70                  75                  80

Gly Ala Gln His Val Arg Ser His Ser Ser Pro Ala Ser Leu Gln Leu
                85                  90                  95

Gly Thr Gly Ala Gly Ala Ala Gly Gly Pro Ala Gln Gln His Ala His
                100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
        130                 135                 140

His Ile Glu Lys Ile Thr Thr Trp Gln Asp Pro Arg Lys Val Met Asn
145                 150                 155                 160

Gln Pro Leu Asn His Val Asn Leu His Pro Ser Ile Thr Ser Thr Ser
                165                 170                 175

Val Pro Gln Arg Ser Met Ala Val Ser Gln Pro Asn Leu Ala Met Asn
                180                 185                 190

His Gln His Gln Gln Val Val Ala Thr Ser Leu Ser Pro Gln Asn His
        195                 200                 205

Pro Thr Gln Asn Gln Pro Thr Gly Leu Met Ser Val Pro Asn Ala Leu
        210                 215                 220

Thr Thr Gln Gln Gln Gln Gln Lys Leu Arg Leu Gln Arg Ile Gln
225                 230                 235                 240

Met Glu Arg Glu Arg Ile Arg Met Arg Gln Glu Glu Leu Met Arg Gln
                245                 250                 255
```

-continued

```
Glu Ala Ala Leu Cys Arg Gln Leu Pro Met Glu Thr Glu Thr Met Ala
            260                 265                 270

Pro Val Asn Thr Pro Ala Met Ser Thr Asp Met Arg Ser Val Thr Asn
        275                 280                 285

Ser Ser Ser Asp Pro Phe Leu Asn Gly Gly Pro Tyr His Ser Arg Glu
    290                 295                 300

Gln Ser Thr Asp Ser Gly Leu Gly Leu Gly Cys Tyr Ser Val Pro Thr
305                 310                 315                 320

Thr Pro Glu Asp Phe Leu Ser Asn Met Asp Glu Met Asp Thr Gly Glu
                325                 330                 335

Asn Ser Gly Gln Thr Pro Met Thr Val Asn Pro Gln Gln Thr Arg Phe
            340                 345                 350

Pro Asp Phe Leu Asp Cys Leu Pro Gly Thr Asn Val Asp Leu Gly Thr
        355                 360                 365

Leu Glu Ser Glu Asp Leu Ile Pro Leu Phe Asn Asp Val Glu Ser Ala
    370                 375                 380

Leu Asn Lys Ser Glu Pro Phe Leu Thr Trp Leu
385                 390                 395

<210> SEQ ID NO 15
<211> LENGTH: 386
<212> TYPE: PRT
<213> ORGANISM: Gallus gallus
<300> PUBLICATION INFORMATION:
<308> DATABASE ACCESSION NUMBER: NCBI/XP_003641834.1
<309> DATABASE ENTRY DATE: 2018-01-04
<313> RELEVANT RESIDUES IN SEQ ID NO: (1)..(386)

<400> SEQUENCE: 15

Met Asn Pro Ser Pro Ala Ala Pro Pro Gly Gln Gln Val Ile His
1               5                   10                  15

Ile Thr Gln Asp Leu Asp Thr Glu Leu Glu Ala Leu Phe Asn Ala Val
            20                  25                  30

Met Asn Pro Arg Pro Ser Ser Trp Arg Lys Lys Ile Leu Pro Glu Ser
        35                  40                  45

Phe Phe Lys Glu Pro Asp Ser Gly Ser His Ser Arg Gln Ser Ser Thr
    50                  55                  60

Asp Ser Gly Gly Pro Pro Arg Pro Val Ala Ala Gln His Val Arg
65                  70                  75                  80

Ser His Ser Ser Pro Ala Ser Leu Val Gly Ser Ala Ala Pro Gln
                85                  90                  95

His Gly His Leu Arg Gln Arg Ser Tyr Asp Val Thr Asp Glu Leu Pro
            100                 105                 110

Leu Pro Pro Gly Trp Glu Met Ala Leu Thr His Thr Gly Gln Arg Tyr
        115                 120                 125

Phe Leu Asn His Ile Glu Lys Ile Thr Thr Trp Gln Asp Pro Arg Lys
    130                 135                 140

Thr Met Asn Gln Pro Leu Asn His Met Ser His Pro Ala Ala Thr
145                 150                 155                 160

Ser Thr Pro Val Pro Gln Arg Ser Met Ala Met Ser Gln Pro Asn Leu
                165                 170                 175

Val Met Asn His Gln His Gln Ile Thr Gly Asn Thr Ser Ile Ser Gln
            180                 185                 190

Gln Ser Cys Pro Ser Gln Thr Pro Gln Pro Gly Leu Leu Asn Met Pro
        195                 200                 205
```

```
Ser Ala Leu Thr Ala Gln Gln Gln Gln Gln Lys Leu Arg Leu Gln
    210                 215                 220

Arg Ile Gln Met Glu Arg Glu Arg Ile Arg Met Arg Gln Glu Glu Leu
225                 230                 235                 240

Leu Arg Gln Glu Ala Ala Leu Cys Arg Gln Leu Pro Met Asp Ser Glu
                245                 250                 255

Asn Met Thr Ala Val Gln Thr Ala Val Ser Thr Ala Ala Met Thr Gln
                260                 265                 270

Asp Met Arg Ser Ile Thr Asn Asn Gly Ser Asp Pro Phe Leu Asn Ser
            275                 280                 285

Gly Pro Tyr His Ser Arg Glu Gln Ser Thr Asp Ser Gly Leu Gly Leu
        290                 295                 300

Gly Cys Tyr Ser Ile Pro Thr Thr Pro Glu Asp Phe Leu Ser Asn Val
305                 310                 315                 320

Asp Glu Met Asp Thr Gly Glu Thr Val Ala Gln Thr Thr Val Asn Ile
                325                 330                 335

Asn Ala Gln Gln Thr Arg Phe Pro Asp Phe Leu Asp Cys Leu Pro Gly
            340                 345                 350

Thr Asn Val Asp Leu Gly Thr Leu Glu Ser Glu Asp Leu Ile Pro Ile
        355                 360                 365

Leu Asn Asp Val Glu Ser Val Leu Ser Lys Asn Glu Pro Phe Leu Thr
370                 375                 380

Trp Leu
385

<210> SEQ ID NO 16
<211> LENGTH: 399
<212> TYPE: PRT
<213> ORGANISM: Sus scrofa
<220> FEATURE:
<221> NAME/KEY: misc_feature
<222> LOCATION: (129)..(129)
<223> OTHER INFORMATION: Xaa can be any naturally occurring amino acid
<300> PUBLICATION INFORMATION:
<308> DATABASE ACCESSION NUMBER: NCBI/XP_013847805.2
<309> DATABASE ENTRY DATE: 2017-05-13
<313> RELEVANT RESIDUES IN SEQ ID NO: (1)..(399)

<400> SEQUENCE: 16

Met Asn Pro Ala Ser Ala Pro Pro Leu Pro Pro Gly Gln Gln
1               5                   10                  15

Val Ile His Val Thr Gln Asp Leu Asp Thr Asp Leu Glu Ala Leu Phe
                20                  25                  30

Asn Ser Val Met Asn Pro Lys Pro Ser Ser Trp Arg Lys Lys Ile Leu
            35                  40                  45

Pro Glu Ser Phe Phe Lys Glu Pro Asp Ser Gly Ser His Ser Arg Gln
        50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Asn Pro Ala Gln Gln His Ala His
                100                 105                 110

Leu Arg Gln Gln Ser Tyr Asp Val Thr Asp Glu Leu Pro Leu Pro Pro
            115                 120                 125

Xaa Trp Glu Met Thr Phe Thr Ala Thr Gly Gln Arg Tyr Phe Leu Asn
130                 135                 140
```

His Ile Glu Lys Ile Thr Thr Trp Gln Asp Pro Arg Lys Ala Met Asn
145                 150                 155                 160

Gln Pro Leu Asn His Met Asn Leu His Pro Ala Ala Thr Ser Thr Pro
            165                 170                 175

Ala Pro Gln Arg Ser Met Ala Val Ser Gln Pro Asn Leu Val Met Asn
        180                 185                 190

His His Gln Gln Gln Met Ala Pro Ser Ser Leu Ser Gln Gln Ser His
    195                 200                 205

Pro Pro Gln Asn Pro Pro Ala Gly Leu Met Asn Met Pro Asn Ala Leu
210                 215                 220

Thr Thr Gln Gln Gln Gln Gln Lys Leu Arg Leu Gln Arg Ile Gln
225                 230                 235                 240

Met Glu Arg Glu Arg Ile Arg Met Arg Gln Glu Leu Met Arg Gln
                245                 250                 255

Glu Ala Ala Leu Cys Arg Gln Leu Pro Met Glu Ala Glu Thr Leu Pro
            260                 265                 270

Thr Val Gln Ala Ala Val Asn Pro Pro Ala Met Thr Pro Asp Met Arg
    275                 280                 285

Ser Ile Thr Asn Asn Ser Ser Asp Pro Phe Leu Asn Gly Gly Pro Tyr
290                 295                 300

His Ser Arg Glu Gln Ser Thr Asp Ser Gly Leu Gly Leu Gly Cys Tyr
305                 310                 315                 320

Ser Val Pro Thr Thr Pro Glu Asp Phe Leu Ser Asn Val Asp Glu Met
                325                 330                 335

Asp Thr Gly Glu Asn Ala Gly Pro Thr Pro Met Asn Ile Asn Pro Gln
            340                 345                 350

Gln Thr Arg Phe Pro Asp Phe Leu Asp Cys Leu Pro Gly Thr Asn Val
        355                 360                 365

Asp Leu Gly Thr Leu Glu Ser Glu Asp Leu Ile Pro Leu Phe Asn Asp
    370                 375                 380

Val Glu Ser Ala Leu Asn Lys Ser Glu Pro Phe Leu Thr Trp Leu
385                 390                 395

<210> SEQ ID NO 17
<211> LENGTH: 400
<212> TYPE: PRT
<213> ORGANISM: Bos taurus
<300> PUBLICATION INFORMATION:
<308> DATABASE ACCESSION NUMBER: NCBI/NP_001179976.1
<309> DATABASE ENTRY DATE: 2015-01-04
<313> RELEVANT RESIDUES IN SEQ ID NO: (1)..(400)

<400> SEQUENCE: 17

Met Asn Pro Ala Ser Ala Pro Pro Leu Pro Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Val Ser Pro Ala Gln Gln His Ala His

```
            100                 105                 110
Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
130                 135                 140

His Ile Glu Lys Ile Thr Thr Trp Gln Asp Pro Arg Lys Ala Met Asn
145                 150                 155                 160

Gln Pro Leu Asn His Met Asn Leu His Pro Ala Ala Thr Ser Thr Pro
                165                 170                 175

Ala Pro Gln Arg Ser Met Ala Val Ser Gln Pro Asn Leu Val Met Asn
            180                 185                 190

His Gln His Gln Gln Met Ala Pro Ser Ser Leu Ser Gln Gln Asn
        195                 200                 205

His Pro Pro Gln Asn Pro Ser Ala Gly Leu Met Ser Met Pro Asn Ala
    210                 215                 220

Leu Thr Thr Gln Gln Gln Gln Lys Leu Arg Leu Gln Arg Ile
225                 230                 235                 240

Gln Met Glu Arg Glu Arg Ile Arg Met Arg Gln Glu Glu Leu Met Arg
                245                 250                 255

Gln Glu Ala Ala Leu Cys Arg Gln Leu Pro Met Glu Ala Glu Thr Leu
            260                 265                 270

Ala Thr Val Gln Ala Ala Val Asn Pro Pro Ala Met Thr Pro Asp Met
        275                 280                 285

Arg Ser Ile Thr Asn Asn Ser Ser Asp Pro Phe Leu Asn Gly Gly Pro
    290                 295                 300

Tyr His Ser Arg Glu Gln Ser Thr Asp Ser Gly Leu Gly Leu Gly Cys
305                 310                 315                 320

Tyr Ser Val Pro Thr Thr Pro Glu Asp Phe Leu Ser Asn Val Asp Glu
                325                 330                 335

Met Asp Thr Gly Glu Asn Thr Gly Gln Thr Pro Met Asn Ile Asn Pro
            340                 345                 350

Gln Gln Thr Arg Phe Pro Asp Phe Leu Asp Cys Leu Pro Gly Thr Asn
        355                 360                 365

Val Asp Leu Gly Thr Leu Glu Ser Glu Asp Leu Ile Pro Leu Phe Asn
    370                 375                 380

Asp Val Glu Ser Ala Leu Asn Lys Ser Glu Pro Phe Leu Thr Trp Leu
385                 390                 395                 400

<210> SEQ ID NO 18
<211> LENGTH: 391
<212> TYPE: PRT
<213> ORGANISM: Danio rerio
<300> PUBLICATION INFORMATION:
<308> DATABASE ACCESSION NUMBER: NCBI/NP_001032785.1
<309> DATABASE ENTRY DATE: 2017-08-06
<313> RELEVANT RESIDUES IN SEQ ID NO: (1)..(391)

<400> SEQUENCE: 18

Met Ser Gly Asn Pro Leu Gln Pro Ile Pro Gly His Gln Val Ile His
1               5                   10                  15

Val Ala Lys Asp Leu Asp Thr Asp Leu Glu Ala Leu Phe Asn Ser Val
            20                  25                  30

Met Asn Pro Lys Pro Ser Ser Trp Arg Asn Lys Asp Met Pro Gln Ser
        35                  40                  45

Phe Phe Gln Glu Pro Asp Ser Gly Ser His Ser Arg Gln Ser Ser Ala
    50                  55                  60
```

```
Asp Ser Gly Ser Leu Pro Pro Arg Val His Phe Arg Ser Arg Ser Ser
 65                  70                  75                  80

Pro Ala Ser Leu Gln Leu Pro Ala Gly Ser Val Ser Gly Pro Ser Pro
                 85                  90                  95

Gly Arg Leu His Ser His Thr Arg His Gln Ser Cys Asp Val Ala Glu
            100                 105                 110

Glu Leu Pro Leu Pro Pro Gly Trp Glu Met Ala Phe Thr Pro Asn Gly
        115                 120                 125

Gln Lys Tyr Phe Leu Asn His Ile Glu Lys Ile Thr Thr Trp His Asp
    130                 135                 140

Pro Arg Lys Ser Met Thr Pro Ser Val Ala Gln Leu Ser Leu His Asn
145                 150                 155                 160

Gln Val Ser Asn Thr Ala Ser Ile Gln Gln Arg Ser Met Ala Leu Ser
                165                 170                 175

Gln Pro Asn Leu Val Leu Asn Gln Gln Ala His Gln Gln Gln Gln Gln
            180                 185                 190

His Leu Gln Gln Gln Gln Gln Val Pro Val Gln Val Pro Val Gln
        195                 200                 205

Ala Pro Gln Gln Gln Ser Ser Gln Pro Met Met Asn Leu Ser Ala Gln
    210                 215                 220

Gln His Gln Gln Lys Met Arg Leu Gln Arg Ile Gln Met Glu Arg Glu
225                 230                 235                 240

Arg Ile Gln Arg Arg Gln Glu Glu Leu Met Arg Gln Glu Val Ala Leu
                245                 250                 255

Arg Gln Leu Pro Met Asp Ser Asp Asn Leu Pro Pro Val Ala Pro Ala
            260                 265                 270

Ile Gly Ser Pro Ala Met Ser Ala Gly Asn Met Pro Asn Asn Ser Ala
        275                 280                 285

Asp Pro Phe Leu Asn Ser Gly Pro Tyr His Ser Arg Glu Gln Ser Thr
    290                 295                 300

Asp Ser Gly Leu Gly Leu Gly Cys Tyr Ser Ile Pro Thr Thr Pro Glu
305                 310                 315                 320

Asp Phe Leu Asn Asn Met Glu Asp Met Asp Thr Gly Glu Asn Met Val
                325                 330                 335

Pro Val Ser Met Asn Val Pro Pro Gln Ser Arg Phe Pro Asp Phe Leu
            340                 345                 350

Asp Ser Met Pro Gly Thr Asn Val Asp Leu Gly Thr Leu Glu Gly Thr
        355                 360                 365

Asp Leu Met Pro Ile Leu Asn Asp Val Glu Ser Val Leu Asn Lys Ser
    370                 375                 380

Glu Pro Phe Leu Thr Trp Leu
385                 390
```

<210> SEQ ID NO 19
<211> LENGTH: 395
<212> TYPE: PRT
<213> ORGANISM: Drosophila melanogaster
<300> PUBLICATION INFORMATION:
<308> DATABASE ACCESSION NUMBER: NCBI/NP_726414.3
<309> DATABASE ENTRY DATE: 2017-08-06
<313> RELEVANT RESIDUES IN SEQ ID NO: (1)..(395)

<400> SEQUENCE: 19

```
Met Leu Thr Thr Met Ser Ala Ser Ser Asn Thr Asn Ser Leu Ile Glu
 1               5                  10                  15
```

```
Lys Glu Ile Asp Asp Glu Asp Met Leu Ser Pro Ile Lys Ser Asn Asn
                 20                  25                  30

Leu Val Val Arg Val Asn Gln Asp Thr Asp Asn Leu Gln Ala Leu
             35                  40                  45

Phe Asp Ser Val Leu Asn Pro Gly Asp Ala Lys Arg Pro Leu Gln Leu
 50                  55                  60

Pro Leu Arg Met Arg Lys Leu Pro Asn Ser Phe Phe Thr Pro Pro Ala
 65                  70                  75                  80

Pro Ser His Ser Arg Ala Asn Ser Ala Asp Ser Thr Tyr Asp Ala Gly
                 85                  90                  95

Ser Gln Ser Ser Ile Asn Ile Gly Asn Lys Ala Ser Ile Val Gln Gln
                100                 105                 110

Pro Asp Gly Gln Ser Pro Ile Ala Ala Ile Pro Gln Leu Gln Ile Gln
                115                 120                 125

Pro Ser Pro Gln His Ser Arg Leu Ala Ile His His Ser Arg Ala Arg
130                 135                 140

Ser Ser Pro Ala Ser Leu Gln Gln Asn Tyr Asn Val Arg Ala Arg Ser
145                 150                 155                 160

Asp Ala Ala Ala Asn Asn Pro Asn Ala Asn Pro Ser Ser Gln Gln
                165                 170                 175

Gln Pro Ala Gly Pro Thr Phe Pro Glu Asn Ser Ala Gln Glu Phe Pro
                180                 185                 190

Ser Gly Ala Pro Ala Ser Ser Ala Ile Asp Leu Asp Ala Met Asn Thr
                195                 200                 205

Cys Met Ser Gln Asp Ile Pro Met Ser Met Gln Thr Val His Lys Lys
210                 215                 220

Gln Arg Ser Tyr Asp Val Ile Ser Pro Ile Gln Leu Asn Arg Gln Leu
225                 230                 235                 240

Gly Ala Leu Pro Pro Gly Trp Glu Gln Ala Lys Thr Asn Asp Gly Gln
                245                 250                 255

Ile Tyr Tyr Leu Asn His Thr Thr Lys Ser Thr Gln Trp Glu Asp Pro
                260                 265                 270

Arg Ile Gln Tyr Arg Gln Gln Gln Ile Leu Met Ala Glu Arg Ile
                275                 280                 285

Lys Gln Asn Asp Val Leu Gln Thr Thr Lys Gln Thr Thr Ser Thr
290                 295                 300

Ile Ala Asn Asn Leu Gly Pro Leu Pro Asp Gly Trp Glu Gln Ala Val
305                 310                 315                 320

Thr Glu Ser Gly Asp Leu Tyr Phe Ile Asn His Ile Asp Arg Thr Thr
                325                 330                 335

Ser Trp Asn Asp Pro Arg Met Gln Ser Gly Leu Ser Val Leu Asp Cys
                340                 345                 350

Pro Asp Asn Leu Val Ser Ser Leu Gln Ile Glu Asp Asn Leu Cys Ser
                355                 360                 365

Asn Leu Phe Asn Asp Ala Gln Ala Ile Val Asn Pro Pro Ser Ser His
                370                 375                 380

Lys Pro Asp Asp Leu Glu Trp Tyr Lys Ile Asn
385                 390                 395
```

<210> SEQ ID NO 20
<211> LENGTH: 19
<212> TYPE: DNA
<213> ORGANISM: Homo sapiens

<400> SEQUENCE: 20

```
cagcagcaac agatgcgac                                                19
```

```
<210> SEQ ID NO 21
<211> LENGTH: 25
<212> TYPE: DNA
<213> ORGANISM: Homo sapiens

<400> SEQUENCE: 21
cagccaaaac agactccatg tcatt                                         25

<210> SEQ ID NO 22
<211> LENGTH: 20
<212> TYPE: DNA
<213> ORGANISM: Homo sapiens

<400> SEQUENCE: 22
agctcagcat cttcgacagt                                               20

<210> SEQ ID NO 23
<211> LENGTH: 22
<212> TYPE: DNA
<213> ORGANISM: Homo sapiens

<400> SEQUENCE: 23
tcaggaagtc atctggggtt cg                                            22

<210> SEQ ID NO 24
<211> LENGTH: 31
<212> TYPE: DNA
<213> ORGANISM: Artificial Sequence
<220> FEATURE:
<223> OTHER INFORMATION: Synthetically constructed primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 24
thacatnrrn cccatgcgca ttaaggtggt c                                  31

<210> SEQ ID NO 25
<211> LENGTH: 20
<212> TYPE: DNA
<213> ORGANISM: Artificial Sequence
<220> FEATURE:
<223> OTHER INFORMATION: Synthetically constructed primer

<400> SEQUENCE: 25
tcgaccggta cgtagtcaca                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetically constructed primer

<400> SEQUENCE: 26
acctacgaag atggaggcgt                                               20

<210> SEQ ID NO 27
```

```
<211> LENGTH: 19
<212> TYPE: DNA
<213> ORGANISM: Artificial Sequence
<220> FEATURE:
<223> OTHER INFORMATION: Synthetically constructed primer

<400> SEQUENCE: 27
gcgtgttccc tctgaacga                                              19

<210> SEQ ID NO 28
<211> LENGTH: 22
<212> TYPE: DNA
<213> ORGANISM: Artificial Sequence
<220> FEATURE:
<223> OTHER INFORMATION: Synthetically constructed primer

<400> SEQUENCE: 28
tccgcgttac ataacttacg gt                                          22

<210> SEQ ID NO 29
<211> LENGTH: 20
<212> TYPE: DNA
<213> ORGANISM: Artificial Sequence
<220> FEATURE:
<223> OTHER INFORMATION: Synthetically constructed primer

<400> SEQUENCE: 29
cccgtgagtc aaaccgctat                                             20

<210> SEQ ID NO 30
<211> LENGTH: 20
<212> TYPE: DNA
<213> ORGANISM: Artificial Sequence
<220> FEATURE:
<223> OTHER INFORMATION: Synthetically constructed primer

<400> SEQUENCE: 30
aagtacgccc cctattgacg                                             20

<210> SEQ ID NO 31
<211> LENGTH: 20
<212> TYPE: DNA
<213> ORGANISM: Artificial Sequence
<220> FEATURE:
<223> OTHER INFORMATION: Synthetically constructed primer

<400> SEQUENCE: 31
tacacgccta ccgcccattt                                             20
```